US 6,586,581 B1
Jul. 1, 2003

(12) United States Patent
Bancroft et al.

(10) Patent No.: US 6,586,581 B1
(45) Date of Patent: Jul. 1, 2003

(54) PROLACTIN REGULATORY ELEMENT BINDING PROTEIN AND USES THEREOF

(75) Inventors: F. Carter Bancroft, Huntington, NY (US); Maikiko Fliss, Columbia, MD (US); Catherine L. Clelland, New York, NY (US)

(73) Assignee: The Mt. Sinai School of Medicine of New York University, New York, NY (US)

( * ) Notice: Subject to any disclaimer, the term of this patent is extended or adjusted under 35 U.S.C. 154(b) by 0 days.

(21) Appl. No.: 09/533,494

(22) Filed: Mar. 23, 2000

Related U.S. Application Data
(60) Provisional application No. 60/125,728, filed on Mar. 23, 1999.

(51) Int. Cl.$^7$ .......................... C07H 21/04; C07H 21/02; C12Q 1/68; C12P 19/34; C12N 15/63
(52) U.S. Cl. .......................... 536/23.5; 435/6; 435/91.1; 435/325; 435/455; 536/23.1
(58) Field of Search .......................... 435/6, 69.1, 70.1, 435/91.1, 455, 456, 375; 514/44; 536/23.1, 24.1, 24.31, 24.5

(56) References Cited

U.S. PATENT DOCUMENTS
6,096,308 A * 8/2000 Lal et al. .................. 424/94.5

OTHER PUBLICATIONS

Karen Pihl–Carey, Isis To Restructure As Crohn's Disease Drug Fails In Phase III; Bio World Today, The Daily Biotechnology Newspaper, vol. 10, No. 239, Dec. 16, 1999 pp. 2 of 5.*
Andrea D. Branch, A good antisense molecule is hard to find; TIBS 23, Feb. 1998 pp. 45–50.*
Giorgio Palu' et al., In pursuit of new developments for gene therapy of human diseases; Journal of Biotechnology 68 (1999) pp. 1–13.*
Stanley T. Crooke, Antisense Research and Application; pp. 1–50.*
Taylor Clelland et al., 2000, "Cloning and characterization of human PREB; a gene that maps to a genomic region associated with trisomy 2p syndrome", *Mammalian Genome*, 11:675–681.
Taylor Clelland et al., 2000, "Mapping and developmental expression analysis of the WD– repeat gene Preb", *Genomics* 63:391–399.
Al–Saffar et al., 1999, Phenotype of patient with pure partial trisomy 2p (p23→pter), *Am. J. Hum. Genet.* 65S(4):850.
Niu et al., 1999, "A genome–wide scan for loci linked to forearm bone mineral density", *Hum. Genet.* 104:226–233.
Fliss et al., 1999, "Expression cloning and characterization of PREB (prolactin regulatory element binding), a novel WD motif DNA–binding Protein with a capacity to regulate prolactin promoter activity", *Mol. Endocrinol.* 13:644.

Hahm et al., 1999, "Trisomy 2p syndrome: a fetus with anecephaly and postaxial polydactylyl", *Am. J. Med. Genet.* 87:45–48.
Taylor Clelland et al., Oct. 19–23, 1999, "Cloning and genomic characterization of the human PREB gene: a conserved WD–repeat protein expressed in the mature adult and during human development", American Society of Human Genetics Meeting, Abstract 1009.
Adler et al., 1998, "Relative effects of prolactin excess and estrogen deficiency on bone in rats", *Metabolism*, 47:425–428.
Bole–Feysot et al., 1998, "Prolactin (PRL) and its receptor: actions, signal transduction pathways and phenotypes observed in PRL receptor knockout mice", *Endocr. Rev.* 19(3): 225–268.
De Petrocellis et al., 1998, "The endogenous cannabinoid anandamide inhibits human breast cancer cell proliferation", *Proc Natl. Acad. Sci. USA* 95(14):8375–8380.
Devoto et al., 1998, "First–stage autosomal genome screen in extended pedigrees suggest genes predisposing to low bone mineral density on chromosome 1p, 2p and 4q", *Eur. J. Hum. Genet.* 6:151–157.
Neidhart, 1998 "Prolactin in autoimmune diseases (44251)", *Proc. Soc. Exp. Biol. Med.* 217:408–419.
Richards et al., 1998, "Prolactin Is an antagonist of TGF–β activity and promotes proliferation of murine B cell hybridomas", *Cell. Immunol.* 184:85–9.
Yu–Lee et al., 1998, "Lactogenic hormone signal transduction", *Biology of Reproduction* 58:295–301.
Bellone et al., 1997, "Bone marrow stroma–derived prolactin is involved in basal and platelet–activating factor–stimulated in vitro erythropoiesis", *Blood* 90(1):21–27.
Berczi, 1997, "Pituitary hormones and immune function", *Acta Paediatr Suppl.* 423:70–75.
Chen et al., 1997, "Linkage mapping of Sax2 to mouse Chromosome 5", *Mamm. Genome* 8:697–698.
Das et al., 1997, "Tamoxifen inhibits prolactin signal transduction in ER—NOG–8 mammary epithelial cells", *Cancer Letters* 116:41–46.

(List continued on next page.)

*Primary Examiner*—Sean McGarry
*Assistant Examiner*—Jane Zara
(74) *Attorney, Agent, or Firm*—Baker Botts LLP

(57) ABSTRACT

The present invention relates to isolated nucleic acid molecules encoding Prolactin Regulatory Element Binding protein (PREB) and recombinant proteins encoded thereby. The nucleic acid sequences are useful in the production of recombinant PREB, as probes, and in the control of gene expression, and in particular, in the control of prolactin gene expression. In particular embodiments of the invention, PREB nucleic acid sequences are used to detect transcripts of the gene in astrocytomas, to detect trisomy and to detect a propensity of a subject to develop osteoporosis. In other embodiments of the invention, the PREB nucleic acid sequences, or the products thereof, are used for preventing or controlling osteoporosis in a subject.

6 Claims, 19 Drawing Sheets

OTHER PUBLICATIONS

Figure 3:
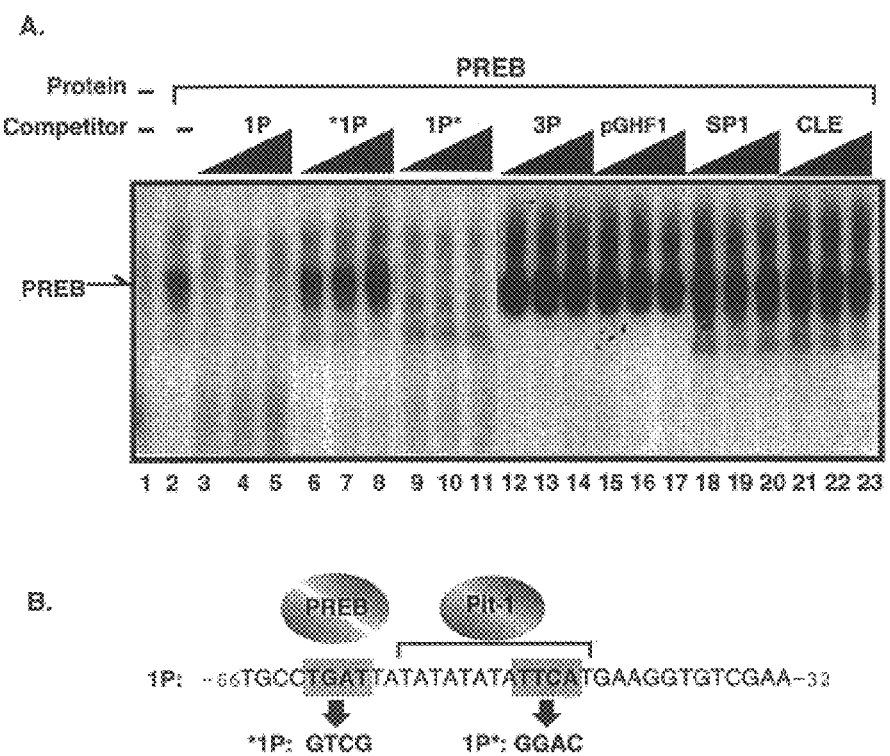

Ferrag et al., 1997, "Immune function of prolactin (PRL) and signal transduction by PRL/GH/cytokine receptors: Specificity, redundancy and lessons from chimaeras", *Cytokines Cell Mol Ther.* 3:197–213.

Lloyd et al., 1997, "Transcription factors in normal and neoplastic pituitary tissues", *Microsc. Res. Tech.* 39:168–181.

Mégarbané et al., 1997, "Interstitial duplication of the short arm of chromosome 2: report of a new case and review", *J. Med. Genet.* 34:783–786.

Patel et al., 1997, "Germline duplication of chromosome 2p and neuroblastoma", *J. Med. Genet.* 34:949–951.

Phimister, 1997, "Inside out, boy you turn me?", *Nat. Genet.* 16:11.

Sándor et al., 1997, "A plazma prolactinszint vizsgálatok jelentösége a postmenopausalis osteoporosis diagnosztikájában", *Orv. Hetil.* 138:71–73 (English abstract only).

Schwärzler et al., 1997, "Prolactin gene expression and prolactin protein in premenopausal and postmenopausal human ovaries", *Fertil. Steril.* 68(4):696–701.

Shaw–Bruha et al., 1997, "Expression of the prolactin gene in normal and neoplastic human breast tissues and human mammary cell lines: Promoter usage and alternative mRNA splicing", *Breast Cancer Res. Treat.* 44:243–253.

Small et al., 1997, "Emerin deletion reveals a common X–chromosome inversion mediated by inverted repeats", *Nat. Genet.* 16:96–99.

Strungs et al., 1997, "Two case reports of breast carcinoma associated with prolactinoma", *Pathology* 29:320–323.

Wennbo et al., 1997, "Transgenic mice overexpressing the prolactin gene develop dramatic enlargement of the prostate gland", *Endocrinology* 138:4410–4415.

Wennbo et al., 1997, "Activation of the prolactin receptor but not the growth hormone receptor is important for induction of mammary tumors in transgenic mice", *J. Clin. Invest.* 100:2744–2751.

Winsor et al., 1997, "A report of recurrent anecephaly with trisomy 2p23–2pter: additional evidence for the involvement of 2p24 in neural tube development and evaluation of the role for cytogenetic analysis", *Prenatal Diagnosis* 17:665–669.

Yu–Lee, 1997, "Molecular actions of prolactin in the immune system (44111)", *Proc. Soc. Exp. Biol. Med.* 215:35–52.

Arenzana–Seisdedos et al., 1996, "HIV blocked by chemokine antagonist", *Nature* 383:400.

Coleman et al., 1996, "Pituitary adenylate cyclase–activating polypeptide regulates prolactin promoter activity via a protein kinase A–mediated pathway that is independent of the transcriptional pathway employed by thyrotropin–releasing hormone", *Endocrinology* 137:1276–1285.

Klijn et al., 1996, "Novel endocrine therapies in breast cancer", *Acta–Oncol.* 35(Suppl. 5):30–37.

Tanaka et al., 1996, "Regional comparison of prolactin gene expression in the human decidualized endometrium in early and term pregnancy", *Eur. J. Endocrinol.* 135:177–183.

Wu et al., 1996, "Expression and localization of prolactin messenger ribonucleic acid in the human immune system", *Endocrinology* 137:349–353.

Clevenger et al., 1995, "Expression of prolactin and prolactin receptor in human breast carcinoma: evidence for an autorcine/paracrine loop", *Am. J. Pathol.* 146(3):695–705.

Cooke, et al., 1995, "Molecular biology of the growth hormone–prolactin gene system", *Vitamins and Hormones* 50:385–459.

De Zegher et al., 1995, "A prismatic case: the prenatal role of thyroid hormone evidenced by fetomaternal Pit–1 deficiency", *J. Clin. Endocrinol. Metab.* 80:3127–3130.

Heldin, 1995, "Dimerization of cell surface receptors in signal transduction", *Cell* 80:213–223.

Lurie et al., 1995, "Trisomy 2p: analysis of unusual phenotypic findings", *Am. J. Med. Genet.* 55:229–236.

Marshall, 1995, "Specificity of receptor tyrosine kinase signaling: transient versus sustained extracellular signal––regulated kinase activation", *Cell* 80:179–185.

Mershon et al., 1995, "Prolactin Is a local growth factor in rat mammary tumors", *Endocrinology* 136:3619–3623.

Rajnarayan et al., 1995, "Reconstitution of protein kinase a regulation of the rat prolactin promoter in HeLa nonpituitary cells: identification of both GHF–1/Pit–1–dependent and – independent mechanisms", *Mol. Endocrinol.* 9:502–512.

Clapp et al., 1994, "The prolactin gene is expressed in the hypothalamic–neurohypophyseal system and the protein is processed into a 14–kDA fragment with activity like 16–kDa prolactin", *Proc. Natl. Acad. Sci. USA* 91:10384–10388.

Fischberg et al., 1994, "A Pit–1 phosphorylation mutant can mediate both basal and induced prolactin and growth hormone promoter activity", *Mol. Endocrinol.* 8:1566–1573.

Gutierrez–Hartmann, 1994, "Insight: Pit–1/GHF–1: A pituitary–specific transcription factor linking general signaling pathways to cell–specific gene expression", *Mol. Endocrinol.* 8(11):1447–1449.

Hinterberger–Fischer et al., 1994, "Prolactin: a possible mediator of graft–versus–host disease following allogeneic bone marrow transplantation in humans", *Bone Marrow Transplant.* 14:403–406.

Howard et al., 1994, "Thyrotropin releasing hormone stimulates transient phosphorylation of the tissue–specific transcription factor, Pit–1", *J. Biol. Chem.* 269(46):28662–28669.

Okimura et al., 1994, "Pit–1 binding sites mediate transcriptional responses to cyclic adenosine, 5'–monophosphate through a mechanism that does not require inducible phosphorylaton of Pit–1", *Mol. Endocrinol.* 8(11):1559–1565.

Yan et al., 1994, "A constitutively active form of CREB can activate expression of the rat prolactin promoter in non–pituitary cells", *Mol. Cell. Endocrinology.* 101:R25–R30.

Halford et al., 1993, "Low–copy–number repeat sequences flank the DiGeorge/velo–cardio–facial syndrome loci at 22q 11", *Hum. Mol. Genet.* 2:191–196.

Chao, 1992, "Growth factor signaling: where is the specificity?", *Cell.* 68:995–997.

Jara et al., 1992, "Hyperprolactinemia in systemic lupus erythematosus: association with disease activity", *Am. J. Med. Sci.* 303(4):222–226.

Keech et al., 1992, "Cyclic adenosine 3',5'–monophosphate activation of the rat prolactin promoter is restricted to the pituitary–specific cell type", *Mol. Endocrinol.* 6(12):2059–2070.

Radovick et al., 1992, "A mutation in the POU–homeodomain of Pit–1 responsible for combined pituitary hormone deficiency", *Science* 257:1115–1118.

Rozhinskaia et al., 1992, "Bone tissue in patients with hyperprolactinemic hypogonadotropism", *Probl. Endokrinol.* 38:17–19 (English abstract only).

Tatsumi et al., 1992, "Cretinism with combined hormone deficiency caused by a mutation in the P1T1 gene", *Natl. Genet.* 1:56–58.

Drolet et al., 1991, "TEF, a transcription factor expressed specifically in the in the anterior pituitary during embryogenesis, defines a new class of leucine zipper proteins", *Genes Dev.* 5:1739–1753.

Segil et al., 1991, "Mitotic phosphorylation of of Oct–1 homeodomain and regulation of Oct–1 DNA binding activity", *Science* 254:1814–1816.

Voss et al., 1991, "POU–domain proteins Pit–1 and Oct–1 interact to form a heteromeric complex and can cooperate to induce expression of the prolactin promoter", *Genes Dev.* 5:1309–1320.

Yan et al., 1991, "Thyrotropin– releasing hormone action on the prolactin promoter is mediated by the POU protein Pit–1", *Mol. Endocrinol.* 5:535–541.

Fox et al., 1990, "The homeodomain protein, Pit–1/GHF–1, is capable of binding to and activating cell–specific elements of both the growth hormone and prolactin gene promoters", *Mol. Endocrinol.* 4(7):1069–1080.

Iverson et al., 1990, "clustered point mutation analysis of the rat prolactin promoter", *Mol. Endocrinol.* 4:1564–1571.

Li et al., 1990, "Dwarf locus mutants lacking three pituitary cell types results from mutations in the POU–domain gene pit–1", *Nature* 347:528–533.

Williams et al., 1990, "Characterization of TUPI, a mediator of glucose repression in *Saccharomyces cerevisiae*", *Mol. Cell. Biol.* 10(12):6500–6511.

Crenshaw et al., 1989, "Cell–specific expression of the protein gene in transgenic mice is controlled by synergistic interactions between promoter and enhancer elements", *Genes Dev.* 3:959–972.

Mangalam et al., 1989, "A pituitary POU domain protein, Pit–1, activates both growth hormone and prolactin promoters transcriptionally" *Genes Dev.* 3:946–958.

Mitchell et al., 1989, "Transcriptional regulation in mammalian cells by sequence–specific DNA binding proteins" *Science* 245:371–378.

Nagy et al., 1989, "Pituitary dependence of bone marrow function", *Br. J. Haematol.* 71:457–462.

Ciccarelli et al., 1988, "Vertebral bone density in non–amenorrhoeic hyperprolactinaemic women" *Clin. Enndocrinol.* 28:1–6.

Jackson et al., 1988, "Proximal upstream flanking sequences direct calcium regulation of the rat prolactin gene", *Mol. Endocrinol.* 2:1139–1144.

Nelson et al., 1988, "Activation of cell–specific expression of rat growth hormone and prolactin genes by a common transcription factor" *Science* 239:1400–1405.

Lufkin et al., 1987, "Identification by cell fusion of gene sequences that interact with positive trans acting factors", *Science* 237:283–286.

Jackson et al., 1986, "Symptomatic osteoporosis in a man with hyperprolactinaemic hypogonodism", *Ann Intern. Med.* 105:543–545.

Clements, 1983, "Expression of the Prolactin Gene in Human Decidua–Chorion", *Endocrinology* 112(3):1133–1134.

Nagy et al., 1983, "Regulation of immunity in rats by lactogenic and growth hormones", *Acta. Endocrinol.* 102:351–357.

Nicoll, 1982, "Prolactin and Growth hormone: specialists on one hand and mutual mimics on the other", *Perspect. Biol. Med.* 25(3):369–38.

Scola et al., 1979, "2p partial trisomy", *Am. J. Human. Genet.* 31(110A):371.

Hammond et al., 1977, "Serum FSH, LH and prolactin in normal males and patients with prostatic diseases", *Clin. Endocrinol.* 7:129–135.

\* cited by examiner

A

```
    1      86  134   160 182  223    279 306  328           417
    ┌──────┬───┬─────┬──┬────┬──────┬───┬────┬──────────────┐
    │      │P/Q│     │WD│ WD │  P/Q │   │ WD │              │
    └──────┴───┴─────┴──┴────┴──────┴───┴────┴──────────────┘
```

```
     -114 ccgagacccctcggcagtcttccggaaaactctagcgccaagttcctgagc
          tttcggaggcgaggcgcggcatgtcgtgggttccgcggggttggcggtgaacgtgcgggcggg
```

B

```
   1    atgggtcggcgccggggtgtggagctgtaccgggccccgttccgttgtacgcgcttcgg
   1     M  G  R  R  R  G  V  E  L  Y  R  A  P  F  P  L  Y  A  L  R
  61    atagaccccaagactgggctgctcatcgctgcgggcggaggaggagctgccaagaccggc
  21     I  D  P  K  T  G  L  L  I  A  A  G  G  G  A  A  K  T  G
 121    ataaagaatggcgtgcatttctgcagctagagctgatcaacgggtgcctgagcgcttcc
  41     I  K  N  G  V  H  F  L  Q  L  E  L  I  N  G  C  L  S  A  S
 181    ttgctgcactctcatgacacggagacacgggccaccatgaatttggcgcttgctggtgac
  61     L  L  H  S  H  D  T  E  T  R  A  T  M  N  L  A  L  A  G  D
 241    attcttgctgccggacaggatgcccagtgtcagcttcttcgtttccaggtccatcaacag
  81     I  L  A  A  G (Q) D  A (Q) C (Q) L  L  R  F (Q) V  H (Q)(Q)
 301    aagggcagtaaagcggagaagtcaggttccaaggagcacccaggtcgacagagaaagggg
 101     K  G  S  K  A  E  K  S  G  S  K  E  H (P) G  R (Q) R  K  G
 361    gctcctccagcagagaagaaatcggagcacaagttcaccgcggaagggggttgaactcaaa
 121     A (P)(P) A  E  K  K  S  G  A (Q) V  H (P) E  G  V  E  L  K
 421    gtaaagaatttggaggcagtacagacagacttcagcaatgaaccgctgcagaaagttgtg
 141     V  K  N  L  E  A  V  Q  T  D  F  S  N  E  P  L  Q  K  V  V
 481    tgcttcaaccatgataacacccctgcttgccaccggaggaactgatggtcatgttcgtgtc
 161     C  F  N  H  D  N  T  L  L  A  T  G  G  T  D  G  H  V  R  V
 541    tggaaggtacctagcctagagaaagttctggagtttaaagcccacgaaggggagattgga
 181     W  K  V  P  S  L  E  K  V  L  E  F  K  A  H  E  G  E  I  G
 601    gatttggctttgggtcctgatggcaagttggttactgtgggctgggactttaaggcctcc
 201     D  L  A  L  G  P  D  G  K  L  V  T  V  G  W  D  F  K  A  S
 661    gtgtggcagaaggatcaactggtgacacagctacagtggcaagagaatggacccacctct
 221     V  W (Q) K  D (Q) L  V  T (Q) L (Q) W (Q) E  N  G (P) T  S
 721    tctaacacaccgtaccgctaccaggcctgcaggtttgggcaggttccagatcagcctggt
 241     S  N  T (P) Y  R  Y (Q) A  C  R  F  G (Q) V (P) D (Q)(P) G
 781    gggctgcgactcttcacagtgcagatacccacaagcgcctacgacagccccacccctgc
 261     G  L  R  L  F  T  V (Q) I (P) H  K  R  L  R (Q)(P)(P)(P) C
 841    tacctcacagcctgggacagttccaccttcttgcctcttcggaccaggtcctgtggccat
 281     Y  L  T  A  W  D  S  S  T  F  L  P  L  R  T  R  S  C  G  H
 901    gaagtcatttcctgcctcactgtcagtgaatcgggtaccttcctaggcctaggcacggtc
 301     E  V  I  S  C  L  T  V  S  E  S  G  T  F  L  G  L  G  T  V
 961    actggctctgtcgccatctacatagctttctctctccagcgcctgtattatgtgaaggag
 321     T  G  S  V  A  I  Y  I  A  F  S  L  Q  R  L  Y  Y  V  K  E
1021    gcccatggcattgtggtgacagatgtgacctttctacctgagaaggggttgcggtccaaag
 341     A  H  G  I  V  V  T  D  V  T  F  L  P  E  K  G  C  G  P  K
1081    ctccttgggccccatgaaacggccctgttctctgtggctgtggatagtcgttgccagttg
 361     L  L  G  P  H  E  T  A  L  F  S  V  A  V  D  S  R  C  Q  L
1141    cacctgctgccctcacggcggagtgttcccgtatggctcctgctcctgctatgtgttggc
 381     H  L  L  P  S  R  R  S  V  P  V  W  L  L  L  L  C  V  G
1201    cttattatcgtgaccatcctgctgctccagagtgccttcccggggtttctttaacatcct
 401     L  I  I  V  T  I  L  L  Q  S  A  F  P  G  F  L  *
1261    gaccaatggagtcatccttggacagtactaccttctggagcagagtcattgaggcccat
1321    gactgaagctgcatctgatgaaatggatgggtactgccggtccctgctaaacgctgcgcc
1381    agtggcctccctatcactctgggtcttgggagccctgctttcacctgtggatccatttaa
1441    gacagtgtggtctgaagctcaggccacactgcctgcctcgtttcctctgcctccagggc
1501    tccagagccgagctcttcctaggaacatgtgaagatgccaaagagcccagaggcattgcc
1561    atccttctcgcagagactgttttcctcctccccttccagtctgcgcacaaggtcctcag
1621    ctttgtcgagacaaagtctgtggaagaggcaaaaggaagacccaggtagcggtgatctgt
1681    aggtagcacccagccagtcaggccagacgcacagggagttcctgggtgacctactgcagc
1741    ctgaggaaagggaaagtgaacctcagtttattaggcaggaagagttgatatttAATAAAg
1801    aaaga
```

Figure 1

1 agatggctac gtccgtgtct ggaaggtgcc cagcctgtag aaggttctgg agttcaaagc 61 ccacgaaggg aggattgaag acctggcttt agggcctgat ggcaagttgg taaccgtggg 121 ccgggacctt aaggcctctg tgtggcagaa ggatcagctg gtgacacagc tgcactggca 181 agaaaatgga cccaccttt ccagcacacc ttaccgctac cagggcctgc aggttttggc 241 aggttccaga ccagnctgct ggccttgcga cttttacag tgcaaatttt cccacaagc

Figure 2.

```
                        A    A
Consensus:              TA   TCA
                        T    T
```

| | | | |
|---|---|---|---|
| 1P | TGC | CTGATTATATATATATTCATGAAGG | TGTCGAA |
| *1P | TGC | CgtcgTATATATATATTCATGAAGG | TGTCGAA |
| 1P* | TGC | CTGATTATATATAggacTGAAGG | TGTCGAA |
| *1P* | TGC | CgtcgTATATATAggacTGAAGG | TGTCGAA |
| 3P | | tgtcTTCCTGAATATGAATAAGA | AATAA |

Figure 3C

```
  1 TGGCAACTCCCCGGTGTGAGAGGGGTAGGGAGTGCTCCCGGCGGCCACGGGGCCGAGTTC
    ACCAGCCGCCGGGGCAGTAGTCGAAGGCCCGGCGCGGCATGTCCTGGGTGCCGCGGTGCG
    GGCAGTGAACGCGCGCCGGGCGGGATGGGCCGGCGCCGGGCGCCAGAGCTGTACCGGGCT
                          M  G  R  R  A  P  E  L  Y  R  A      12
    CCGTTCCCGTTGTACGCGCTTCAGGTCGACCCAGCACTGGGCTGCTCATCGCTGCGGGC
     P  F  F  L  Y  A  L  Q  V  D  P  S  T  G  L  L  I  A  A  G   32
    GGAGGAGGCGCCGCCAAGACAGGCATAAAGAATGGCGTGACTTTCTGCAGCTAGAGCTG
     G  G  A  A  K  T  G  I  K  N  G  V  H  F  L  Q  L  E  L      52
    ATTAATGGGCGCTTGAGTGCCTCCTTGCTGCACTCCCATGACACAGAGACACGGGCCACC
     I  N  G  R  L  S  A  S  L  L  H  S  H  D  T  E  T  R  A  Y   72
    ATGAACTTGGCACTGGCTGGTGACATCCTTGCTGCAGGGCAGGATGCCCACTGTCAGCTC
     M  N  L  A  L  A  G  D  I  L  A  A  G  Q  D  A  H  C  Q  L   92
    CTGCGCTTCCAGGCACATCAACAGCAGGGCAACAAGGCAGAGAAGGCCGGTTCCAAGGAG
     L  R  F  Q  A  H  Q  Q  Q  G  N  K  A  E  K  A  G  S  K  E  112
    CAGGGGCCTCGACAAAGGAAGGGAGCAGCCCCAGCAGAGAAGAAATGTGGAGCGGAAACC
     Q  G  P  R  Q  R  K  G  A  A  P  A  E  K  K  C  G  A  E  T  132
    CAGCACGAGGGGCTAGAACTCAGGGTAGAGAATTTGCAGGCGGTGCAGACAGACTTTAGC
     Q  H  E  G  L  E  L  R  V  E  N  L  Q  A  V  Q  T  D  F  S  152
    TCCGATCCACTGCAGAAAGTTGTGTGCTTCAACCACGATAATACCCTGCTTGCCACTGGA
     S  D  P  L  Q  K  V  V  C  F  N  H  D  N  T  L  L  A  T  G  172
    GGAACAGATGGCTACGTCCGTGTCTGGAAGTGCCCAGCCTGGAGAAGGTTCTGGAGTTC
     G  T  D  G  Y  V  R  V  W  K  V  P  S  L  E  K  V  L  E  F  192
    AAAGCCCACGAAGGGGAGATTGAAGACCTGGCTTTAGGGCCTGATGGCAAGTGGTAACC
     K  A  H  E  G  E  I  E  D  L  A  L  G  P  D  G  K  L  V  T  212
    GTGGGCCGGGACCTTAAGGCCTCTGTGTGGCAGAAGGATCAGCTGGTGACACAGCTGCAC
     V  G  R  D  L  K  A  S  V  W  Q  K  D  Q  L  V  T  Q  L  H  232
    TGGCAAGAAAATGGACCCACCTTTTCCAGCACACCTTACCGCTACCAGGCCTGCAGGTTT
     W  Q  E  N  G  P  T  F  S  S  T  P  Y  R  Y  Q  A  C  R  F  252
    GGGCAGGTTCCAGACCAGCCTGCTGGCCTGCGACTCTTCACAGTGCAAATTCCCCACAAG
     G  Q  V  P  D  Q  P  A  G  L  R  L  F  T  V  Q  I  P  H  K  272
    CGCCTGCGCCAGCCCCCTCCCTGCTACCTCACAGCCTGGGATGGCTCCAACTTCTTGCCC
     R  L  R  Q  P  P  P  C  Y  L  T  A  W  D  G  S  N  F  L  P  292
    CTTCGGACCAAGTCCTGTGGCCATGAAGTGGTCTCCTGCCTCGATGTCAGTGAATCCGGC
     L  R  T  K  S  C  G  H  E  V  V  S  C  L  D  V  S  E  S  G  312
    ACCTTCCTAGGCCTGGGCACAGTCACTGGCTCTGTTGCCATCTACATAGCTTTCTCTCTC
     T  F  L  G  L  G  T  V  T  G  S  V  A  I  Y  I  A  F  S  L  332
    CAGTGCCTCTACTACGTGAGGGAGGCCCATGGCATTGTGGTGACGGATGTGGCCTTTCTA
     Q  C  L  Y  Y  V  R  E  A  H  G  I  V  V  T  D  V  A  F  L  352
    CCTGAGAAGGGTCGTGGTCCAGAGCTCCTTGGGTCCCATGAAACTGCCCTGTTCTCTGTG
     P  E  K  G  R  G  P  E  L  L  G  S  H  E  T  A  L  F  S  V  372
    GCTGTGGACAGTCGTTGCCAGCTGCATCTGTTGCCCTCACGGAGAGTGTTCCTGTGTGG
     A  V  D  S  R  C  Q  L  H  L  L  P  S  R  R  S  V  P  V  W  392
    CTCCTGCTCCTGCTGTGTGTCGGGCTTATTATTGTGACCATCCTGCTGCTCCAGAGTGCC
     L  L  L  L  C  V  G  L  I  I  V  T  I  L  L  Q  S  A       412
    TTTCCAGGTTTCCTTTAGCTTCCCTGCTTCCTGGGAATCAGGAGCCTGGACACTGCCATC
     F  P  G  F  L  *                                              417
    TCTAGAGCAGAGTGGAGGCCTGGACTCCCTTTGCTCACTCCATTCGGGTCCACAGCTGAG
    GTTGCCTCTGACAAGATGAATGGGCACTGCCTGCCCCTTCTAGTGAAAAGGCTTGGCTATG
    GCCCTGTGTGACTCCAGGTCCCAGGAACCCTTGCCTTCGTCATCTGTGGATCCATCCAGAA
    CAGCGGTATCTGAAGCCCAGGCCATACTCCCTGCCTCCTTTCTTCTGCCTACCAGAGGCT
    CCAGAGTTGAGCTTGTCCTTATCTAGAAACATGTGAAGATGCCCAAGAGCCTGGAGGCAC
    TGCTGTCCTTCCTGCAGAAACAGTTTCTCCTCCTCCCCTCAGCCTTGTGGCCAGTTCCTC
    TTCACATGAAGCCCCTGGCATTTGCTGGGAAGGGACTGGCCTGGTACTTGCTGTTAGGG
    CAGGAAGGGGCAAAAGGAAGACTTGGGTAGTAATCTGGGGGTTCAGATGGGTAGCACTAA
    GCCAGCTGGCCTAAAGATGCAATAAGTTCCTAGGTAGTCTACCCTTACCTTGAGGAATGG
    GAAAATGAACCTCAGCCCATTAGGCAGGAAAAGTTGATATTTAATAAACAAGGAAAGAGT
    GAACTTGAGACCCCAAAAAAAAAAAAAAAAAAA                         2072
```

Figure 11

```
HUMAN PREB 1   S    Q V                    Y    K
  RAT PREB 1   N    Q V                    H    K
MURINE PREB 1  N    Q V                    H    K
 YEAST TUP1 2  S    T G                    L

HUMAN PREB 2        D                 V  KAS   Q
  RAT PREB 2        D                 V  KAS   Q
MURINE PREB 2       D                 V  KAS   Q
 YEAST TUP1 3

HUMAN PREB 3   -              GL T T    AI  I
  RAT PREB 3   -              GL T T    AI  I
MURINE PREB 3  -              GL T T    AI  I
```

```
WD CONSENSUS  GHxxxVxSVxFxPDGxxLASGSxDxTIKVWD
              A        I  AL W DND   IVTAG     SVRLFN
              S           CI L SSN   VL         R   Y
                             I  TS    I
                             V
                             Y
```

Figure 12

```
   1 TGGCAACTCC CCGGTGTGAG AGGGGTAGGG AGTGCTCCCG GCGGCGACGG
  51 GGCCGAGTTC ACCAGCCGCC GGGGCAGTAG TCGAAGGCCC GGCGCGGCAT
 101 GTCCTGGGTG CCGCGGTGCG GGCAGTGAAC GCGCGCCGGG CGGGATGGGC
 151 CGGCGCCGGG CGCCAGAGCT GTACCGGGCT CCGTTCCCGT TGTACGCGCT
 201 TCAGGTCGAC CCCAGCACTG GGCTGCTCAT CGCTGCGGGC GGAGGAGGCG
 251 CCGCCAAGAC AGGCATAAAG AATGGCGTGC ACTTTCTGCA GCTAGAGCTG
 301 ATTAATGGGC GCTTGAGTGC CTCCTTGCTG CACTCCCATG ACACAGAGAC
 351 ACGGGCCACC ATGAACTTGG CACTGGCTGG TGACATCCTT GCTGCAGGGC
 401 AGGATGCCCA CTGTCAGCTC CTGCGCTTCC AGGCACATCA ACAGCAGGGC
 451 AACAAGGCAG AGAAGGCCGG TTCCAAGGAG CAGGGGCCTC GACAAAGGAA
 501 GGGAGCAGCC CCAGCAGAGA AGAAATGTGG AGCGGAAACC CAGCACGAGG
 551 GGCTAGAACT CAGGGTAGAG AATTTGCAGG CGGTGCAGAC AGACTTTAGC
 601 TCCGATCCAC TGCAGAAAGT TGTGTGCTTC AACCACGATA ATACCCTGCT
 651 TGCCACTGGA GGAACAGATG GCTACGTCCG TGTCTGGAAG GTGCCCAGCC
 701 TGGAGAAGGT TCTGGAGTTC AAAGCCCACG AAGGGGAGAT TGAAGACCTG
 751 GCTTTAGGGC CTGATGGCAA GTTGGTAACC GTGGGCCGGG ACCTTAAGGC
 801 CTCTGTGTGG CAGAAGGATC AGCTGGTGAC ACAGCTGCAC TGGCAAGAAA
 851 ATGGACCCAC CTTTTCCAGC ACACCTTACC GCTACCAGGC CTGCAGGTTT
 901 GGGCAGGTTC CAGACCAGCC TGCTGGCCTG CGACTCTTCA CAGTGCAAAT
 951 TCCCCACAAG CGCCTGCGCC AGCCCCTCC CTGCTACCTC ACAGCCTGGG
1001 ATGGCTCCAA CTTCTTGCCC CTTCGGACCA AGTCCTGTGG CCATGAAGTC
1051 GTCTCCTGCC TCGATGTCAG TGAATCCGGC ACCTTCCTAG GCCTGGGCAC
1101 AGTCACTGGC TCTGTTGCCA TCTACATAGC TTTCTCTCTC CAGGGAGTGT
1151 TCCTGTGTGG CTCCTGCTCC TGCTGTGTGT CGGGCTTATT ATTGTGACCA
1201 TCCTGCTGCT CCAGAGTGCC TTTCCAGGTT CCTTTAGCT TCCCTGCTTC
1251 CTGGGAATCA GGAGCCTGGA CACTGCCATC TCTAGAGCAG AGTGGAGGCC
1301 TGGACTCCCT TTGCTCACTC CATTCGGGTC ACACAGCTGAG GTTGCCTCTG
1351 ACAAGATGAA TGGGCACTGC CTGCCCTTCT AGTGAAAAGG CTTGGCTATG
1401 GCCCTGTGTG ACTCCAGGTC CCAGGAACCT TGCCTTCGTC ATCTGTGGAT
1451 CCATCCAGAA CAGCGGTATC TGAAGCCCAG GCCATACTCC CTGCCTCCTT
1501 TCTTCTGCCT ACCAGAGGCT CCAGAGTTGA GCTTGTCCTT ATCTAGAAAC
1551 ATGTGAAGAT GCCCAAGAGC CTGGAGGCAC TGCTGTCCTT CCTGCAGAAA
1601 CAGTTTCTCC TCCTCCCCTC AGCCTTGTGG CCAGTTCCTC TTCACATGAA
1651 GCCCCTGGCA TTTGCTGGGG AAGGGACTGG CCTGGTACTT GCTGTTAGGG
1701 CAGGAAGGGG CAAAAGGAAG ACTTGGGTAG TAATCTGGGG GTTCAGATGG
1751 GTAGCACTAA GCCAGCTGGC CTAAAGATGC AATAAGTTCC TAGGTAGTCT
1801 ACCCTTACCT TGAGGAATGG GAAAATGAAC CTCAGCCCAT TAGGCAGGAA
1851 AAGTTGATAT TTAATAAACA AGGAAAGAGT GAACTTGAGA CCCCAAAAAA
1901 AAAAAAAAA AA
```

Figure 15A

```
  1  MGRRRAPELY  RAPFPLYALQ  VDPSTGLLIA  AGGGGAAKTG  IKNGVHFLQL

51  ELINGRLSAS  LLHSHDTETR  ATMNLALAGD  ILAAGQDAHC  QLLRFQAHQQ

101  QGNKAEKAGS  KEQGPRQRKG  AAPAEKKCGA  ETQHEGLELR  VENLQAVQTD

151  FSSDPLQKVV  CFNHDNTLLA  TGGTDGYVRV  WKVPSLEKVL  EFKAHEGEIE

201  DLALGPDGKL  VTVGRDLKAS  VWQKDQLVTQ  LHWQENGPTF  SSTPYRYQAC

251  RFGQVPDQPA  GLRLFTVQIP  HKRLRQPPPC  YLTAWDGSNF  LPLRTKSCGH

301  EVVSCLDVSE  SGTFLGLGTV  TGSVAIYIAF  SLQGVFLCGS  CSCCVSGLLL
```

Figure 15B

```
GGATCCCCATGTTGCCCAGGCTGTCTCGAAAGCCTGGGCTCAAGCCATCCTCCTCTCTCGGACTTTCCGAAAGTGTTGGGATTACAGGAGGATTACA
GGCATGAACCACCGTGCCTGGCAGAGGATTTTTTTTTTTTGAGACGGAGTTTCACTCTTGTTGCTTGTTGCCCAGGCTGAAGAGCAATGGCAATG
GCGCGATCTCGGCTCACTGCAACCTCTACTTCCCAGGTTCAAGTGATTCTCCTGCCTCAGGCTCCCGAGTAGCTGGGATTACAGGCGCACGCCACCA
CGCCCTTTGTATTTTTGGTAGAGACGGGGTTTCTCCATGTTGGTCAGGCTGGTCTCGAACTCCTGATCCGCCCGCCTAGGACTCACAAAGTGCTGGG
ATTACAGGCGCGAGTCGGATTTCTTTATTAAAGGTTGACCTTCATCAACCTCCATTGGGTCCACCTCCTCCGCCCGCGCCCCGCGCCCCGCACAAAA
ATGGCGAAGTCGGTGCTGGGCGACTCTGCCTCCGCGCCAGGGGTGGAGAACCGAAGCCCCGCCCCGGGAAACGCCGCCCCGCGGCCGGCTAGTGCTG
ACGCGTGTCGGCGCTCCTGCGCCTGCGCGGAGGGAGCCGCGAGACAGGTGCGCATGCGCAATGCGCGTCTGCGAGAACGACTTGGACGGGAGCCGAC
CTGAGGCTCCGCTTCCTGCTGATGGTCAAGGGTTT
TGGCAACTCCCCGGTGTGAGAGGGGTAGGGAGTGCTCCCGGCGGCGACGGGGCCGAGTTCACCAGCCGCCGGGGCAGTAG
TCGAAGGCCCGGCGCGGCATGTCCTGGGTGCCGCGGTGCGGGCAGTGAACGCGCGCCGGG
CGGGATGGGCCGGCGCCGGGCGCCAGAGCTGTACCGGGCTCCGTTCCCGTTGTACGCGCTTCAGGTCGACCCCAGCACTG
GGCTGCTCATCGCTGCGGGCGGAGGAGGCGCCGCCAAGACAGGCATAAAGAATGGCGTG
GTGAGAGCGCAGGGCCACTGGGGCTGGGTCTTGCTGCGGGCTGGCGGCGATTCCAAGGTGGCCGGGGGGTCGCGGGGCGGGCCACACTCCAGCTTCG
GGCCCTGCCCACTTCTGTTGGGAAGACCCCGCTTGCCTGACGCCCAGGGGCGAATTTCAGTCGAGAACTCAGGCGGGCGGAGGAGAGGCTTTTAAGGT
AAAGTGAAAACTGCACACAGCTGCAGAGTCGCGAGGAACGCTTCAGCTCCGCCTCAGAACAGCTCCAGGGGTCTTATACTGGCCTTTTCCGGGAGGT
CTTGCCTGCCCTCTAGCAGCGGCGAGAGTGGTGCATTTGGGTTTAAGCTAAGTTCCTTCCCTCTCCTGAGCTTAACCTGTTCTGTAAAATAAAGGTA
ATAATCCCAATCCTGCTCACTGTGTATATTTGTGAGGCCCAAATGAGAAAAAAAAGACTCGAGAAAACCTTGTGAACTAAAACGTGCAAAAAACAAA
AGGGGTAAAACATCAGACTCTTCCCTAAACGTGCTCTCTGGGGCACCCCTGAAATTGCTCATCCGGGTTCCCCCTCCCACAG
CACTTTCTGCAGCTAGAGCTGATTAATGGGCGCTTGAGTGCCTCCTTGCTGCACTCCCATGACACAGAGAC
ACGGGCCACCATGAACTTGGCACTGGCTGGTGACATCCTTGCTGCAGGGCAGGATGCCCACTGTCAGCTCCTGCGCTTCC
AGGCACATCAACAGCAGGGCAACAAGGCAGAGAAGGCCG
GTTGAGGACTCCCTTTTTACCCCCTTTGGGAAAGGGTTGAACGAGNAAGTCACTCTTTGTGT
CTCTAAAGAAGTTGGTCTTGAAGTAGGTTTTGTAGCAAGCTAGAAGTTGTTTGGGCACCTGCCATTGGAGAGGAGGGGCC
AGTACTCCTTACTGTAGAAGCTTGAACCTGGCCAAGTGTTTGTGTTACAG
GTTCCAAGGAGCAGGGCCTCGACAAAGGAAGGGAGCAGCCCCAGCAGAGAAGAAATGTGGAGCGGAAACC
CAGCACGAGGGGCTAGAACTCAGGGTAGAGAATTTGCAGGCGGTGCAGACAGACTTTAGCTCCGATCCACTGCAGAAAGTTGTGTGCTTCAACCACG
ATAATACCCTGCTTGCCACTGGAGGAACAGATGGCTACGTCCGTGTCTGGAAG
GTGTGGGTTTGCAGGGTTAGGGAGGGTGAATGTCAGTAGCAACAGGATCAAAATTGTGAGAAGTTGAACGTGGCATCTG
GGAAACTTGTGAATGAAGCTTGCATTGAGGGGCCATTAGAAGGGGTGGCGTGGGCATCAGTCACAGTGTACTTGCTGGACACCTGAGTTAACCATGG
TGGTTGTTTGGCTACAG
GTGCCCAGCCTGGAAAGGTTCTGGAGTTCAAAGCCCACGAAGGGGAGATTGAAGACCTGGCTTTAGGGCCTGATGGCAAG
GTGAGGGGCTGGGGGTGGGAGGAGGATGGAGAAAGGAGAGAGGAGGTGCTTATGCTGCTTGCCCAGTAAGTGGAT
CCCCTAACTGTCCATCCTTGGAATCTTTATTCCTAACTAG
TTGGTAACCGTGGGCCGGGACCTTAAGGCCTCTGTGTGTGGCAGAAGGATCAGCTGGTGACACAGCTGCACTGGCAAGAAA
ATGGACCCACCTTTTCCAGCACACCTTACCGCTACCAGGCCTGCAG
GTGTGAAGACTTTGGGGGGTGCTGAAAGAGGCATAGCCCAGCTGTGGTGGGGGAGAGGGAAAAGACTGGGGATG
GGAGAGCTGGGGAGGAACTTGTTGAGTGTTACCCCAGGTCTGACCAGGGTGCAGGTGGTGCACAAACCTCTGAGGAGGGT
TGGGCAGGCCCTANGAGCTGAATAACCCCTCATCCGGCCCCAG
GTTTGGGCAGGTTCCAGACCAGCCTGCTGGCCTGCGACTCTTCACAGTGCAAATTCCCCACAAGCGCCTGCGCC
AGCCCCCTCCCTGCTACCTCACAGCCTGGGATGGCTCCAACTTCTTGCCCCTTCGGACCAAGTCCTGTGGCCATGAAGTCGTCTCCTGCCTCGATGTCAG
GTGTTAGACATTGCTGCCTTGGGCTAGGTAGGGGGTCCCTGAGGGAGCTTGGAAAGGAGTCCTGCCTGGGT
CCCTACGGACCGGTATTGGGGTATGAGGGTTGCTGCACAAGCCTCCAGGACAATGAGCTCTTTATTGTTTGTTGCAG
TGAATCCGGCACCTTCCTAGGCCTGGGCACAGTCACTGGCTCACTGGCATCTACATAGCTTTCTCTCTCCAG
GTAATGGGTGGAGGTTGGCATGGCCCTGTGGGTGGACTGTAGGCCTGTCTCTACCCTGAGTTTGCAGGAAGGAGTCTGGC
CCATCCTATCGAGGGAAATCCTGGGGGTGGGGAACATGCTTTCCAGAAAGAGAGTTCCCAGCTAGGCCTTTCCTCACTGG TATTCCTTCTGCCCACAG
TGCCTCTACTACGTGAGGGAGGCCCATGGCATTGTGGTGACGGATGTGGCCTTTCTACCTGAGAAGGGTCGTGGTCC
AGAGCTCCTTGGGTCCCATGAAACTGCCCTGTTCTCTGTGGCTGTGGACAGTCGTTGCCAGCTGCATCTGTTGCCCTCACGGC
GTGAGTCATTGGGGCAGGGCAGGCAGGCACCACCCCACGTTTAATGACCAGAAACGTGCCCCCCGGAGGCTGG
GCTCTTTGTGCCACTCCTCCTTTGAAGGGTTCTGGTTTTCAGGCTGGGAAGCCCTTTTGCCCGCTGACCTCCTCCCTTTCCCTCCTGCAG
GGAGTGTTCCTGTGTGGCTCCTGCTCCTGCTGTGTCGGGCTTATTATTGTGACCATCCTGCTGCTCCAGAGTGCCTTTCCAGGTTTCCTTTAGCT
TCCCTGCTTCCTGGGAATCAGGAGCCTGGACACTGCCATCTCTAGAGCAGAGTGGAGGCCTGGACTCCCTTTGCTCACTCCATTCGGGTCCACAGCT
GAGGTTGCCTCTGACAAGATGAATGGGCACTGCCTGCCCTTCTAGTGAAAAGGCTTGGCTATGGCCCTGTGTGACTCCAGGTCCCAGGAACCTTGCC
TTCGTCATCTGTGGATCCATCCAGAACAGCGGTATCTGAAGCCCAGGCCATACTCCCTGCCTCCTTTCTTCTGCCTACCAGAGGCTCCAGAGTTGAG
CTTGTCCTTATCTAGAAACATGTGAAGATGCCCAAGAGCCTGGAGGCACTGCTGTCCTTCCTGCAGAAACAGTTTCTCCTCCTCCCCTCAGCCTTGT
GGCCAGTTCCTCTTCACATGAGCCCCTGGCATTTGCTGGGGAAGGGACTGGCCTGGTACTTGCTGTTAGGGCAGGAAGGGGCAAAAGGAAGACTTG
GGTAGTAATCTGGGGGTTCAGATGGGTAGCACTAAGCCAGCTGGCCTAAAGATGCAATAAGTTCCTAGGTAGTCTACCCTTACCTTGAGGAATGGGA
AAATGAACCTCAGCCCATTAGGCAGGAAAAGTTGATATTTAATAAACAAGGAAAGAGTGAACTTGAGACC
```

Figure 16

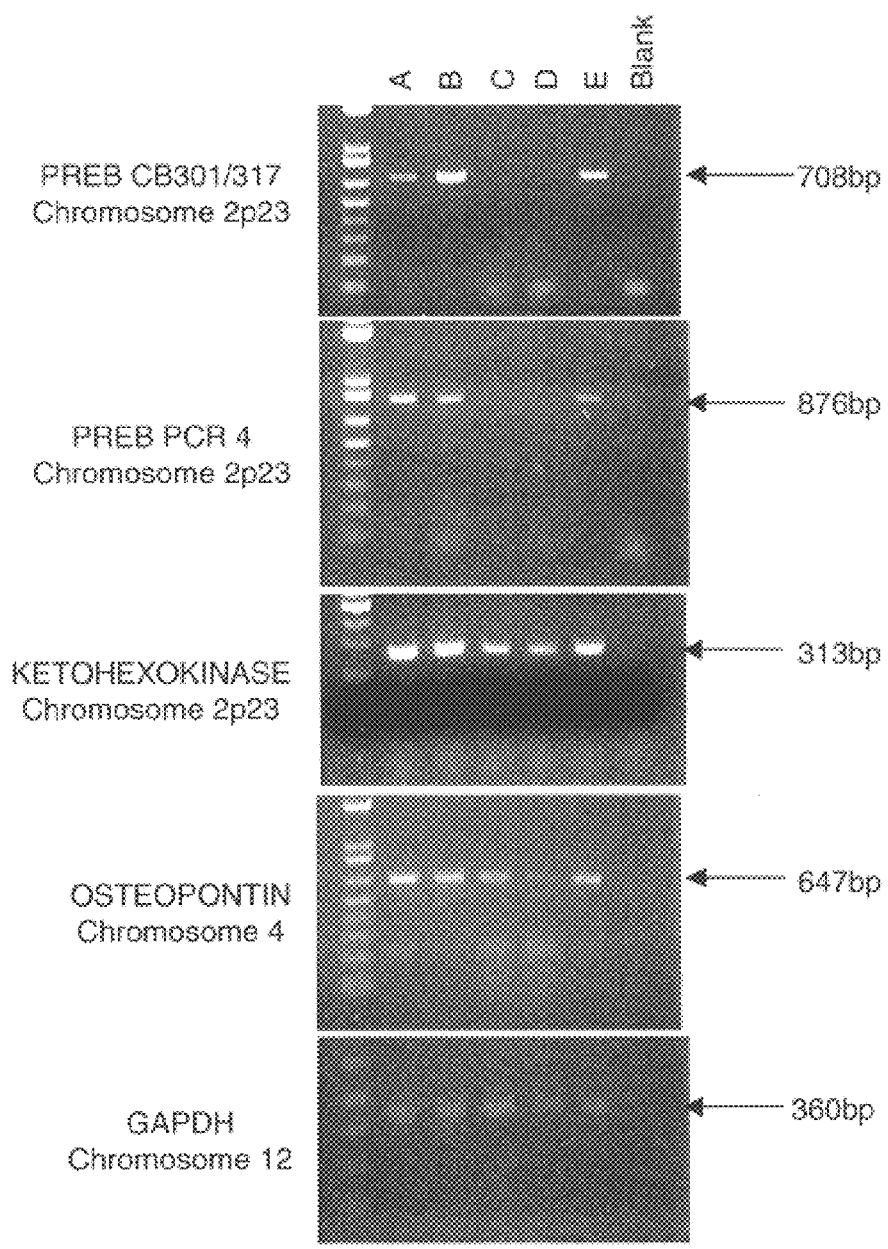

Figure 17. Gene PCR Amplification from a nuclear family with low BMD Linkage to 2p23-24. Ethidium bromide stained agarose gel of PCR amplified products using gene specific primers for PREB (CB301/317; PREB PCR 4), ketohexokinase, osteopontin, and GAPDH. Arrows indicate PCR amplified products of the correct size, determined by a 1kb+ DNA ladder. A= Affected mother, B= Unaffected father, C=Affected offspring, D= affected offspring, E= control DNA sample.

SEQUENCE LISTING

```
<160> NUMBER OF SEQ ID NOS:  30

<210> SEQ ID NO 1
<211> LENGTH: 1924
<212> TYPE: DNA
<213> ORGANISM: Rat
<220> FEATURE:
<221> NAME/KEY: CDS
```

```
<222> LOCATION: (120)...(1373)
<223> OTHER INFORMATION: PREB coding region

<400> SEQUENCE: 1
```

| | | |
|---|---|---|
| gaattccgag accctcggc agtcttccgg aaaactctag cgccaagttc ctgagctttc | 60 |
| ggaggcgagg cgcggcatgt cgtgggttcc gcggggttgg cggtgaacgt gcgggcggg | 119 |

| | | |
|---|---|---|
| atg ggt cgg cgc cgg ggt gtg gag ctg tac cgg gcc ccg ttc ccg ttg<br>Met Gly Arg Arg Arg Gly Val Glu Leu Tyr Arg Ala Pro Phe Pro Leu<br>1               5                   10                  15 | 167 |
| tac gcg ctt cgg ata gac ccc aag act ggg ctg ctc atc gct gcg ggc<br>Tyr Ala Leu Arg Ile Asp Pro Lys Thr Gly Leu Leu Ile Ala Ala Gly<br>            20                  25                  30 | 215 |
| gga gga gga gct gcc aag acc ggc ata aag aat ggc gtg cat ttt ctg<br>Gly Gly Gly Ala Ala Lys Thr Gly Ile Lys Asn Gly Val His Phe Leu<br>        35                  40                  45 | 263 |
| cag cta gag ctg atc aac ggg tgc ctg agc gct tcc ttg ctg cac tct<br>Gln Leu Glu Leu Ile Asn Gly Cys Leu Ser Ala Ser Leu Leu His Ser<br>    50                  55                  60 | 311 |
| cat gac acg gag aca cgg gcc acc atg aat ttg gcg ctt gct ggt gac<br>His Asp Thr Glu Thr Arg Ala Thr Met Asn Leu Ala Leu Ala Gly Asp<br>65                  70                  75                  80 | 359 |
| att ctt gct gcc gga cag gat gcc cag tgt cag ctt ctt cgt ttc cag<br>Ile Leu Ala Ala Gly Gln Asp Ala Gln Cys Gln Leu Leu Arg Phe Gln<br>                85                  90                  95 | 407 |
| gtc cat caa cag aag ggc agt aaa gcg gag aag tca ggt tcc aag gag<br>Val His Gln Gln Lys Gly Ser Lys Ala Glu Lys Ser Gly Ser Lys Glu<br>            100                 105                 110 | 455 |
| cag gga cct cga cag aga aag ggg gct cct cca gca gag aag aaa tcg<br>Gln Gly Pro Arg Gln Arg Lys Gly Ala Pro Pro Ala Glu Lys Lys Ser<br>        115                 120                 125 | 503 |
| gga gca caa gtt cac ccg gaa ggg gtt gaa ctc aaa gta aag aat ttg<br>Gly Ala Gln Val His Pro Glu Gly Val Glu Leu Lys Val Lys Asn Leu<br>    130                 135                 140 | 551 |
| gag gca gta cag aca gac ttc agc aat gaa ccg ctg cag aaa gtt gtg<br>Glu Ala Val Gln Thr Asp Phe Ser Asn Glu Pro Leu Gln Lys Val Val<br>145                 150                 155                 160 | 599 |
| tgc ttc aac cat gat aac acc ctg ctt gcc acc gga gga act gat ggt<br>Cys Phe Asn His Asp Asn Thr Leu Leu Ala Thr Gly Gly Thr Asp Gly<br>                165                 170                 175 | 647 |
| cat gtt cgt gtc tgg aag gta cct agc cta gag aaa gtt ctg gag ttt<br>His Val Arg Val Trp Lys Val Pro Ser Leu Glu Lys Val Leu Glu Phe<br>            180                 185                 190 | 695 |
| aaa gcc cac gaa ggg gag att gga gat ttg gct ttg ggt cct gat ggc<br>Lys Ala His Glu Gly Glu Ile Gly Asp Leu Ala Leu Gly Pro Asp Gly<br>        195                 200                 205 | 743 |
| aag ttg gtt act gtg ggc tgg gac ttt aag gcc tcc gtg tgg cag aag<br>Lys Leu Val Thr Val Gly Trp Asp Phe Lys Ala Ser Val Trp Gln Lys<br>    210                 215                 220 | 791 |
| gat caa ctg gtg aca cag cta cag tgg caa gag aat gga ccc acc tct<br>Asp Gln Leu Val Thr Gln Leu Gln Trp Gln Glu Asn Gly Pro Thr Ser<br>225                 230                 235                 240 | 839 |
| tct aac aca ccg tac cgc tac cag gcc tgc agg ttt ggg cag gtt cca<br>Ser Asn Thr Pro Tyr Arg Tyr Gln Ala Cys Arg Phe Gly Gln Val Pro<br>                245                 250                 255 | 887 |
| gat cag cct ggt ggg ctg cga ctc ttc aca gtg cag ata ccc cac aag<br>Asp Gln Pro Gly Gly Leu Arg Leu Phe Thr Val Gln Ile Pro His Lys<br>            260                 265                 270 | 935 |
| cgc cta cga cag ccc cca ccc tgc tac ctc aca gcc tgg gac agt tcc<br>Arg Leu Arg Gln Pro Pro Pro Cys Tyr Leu Thr Ala Trp Asp Ser Ser | 983 |

-continued

```
                  275                 280                   285
acc ttc ttg cct ctt cgg acc agg tcc tgt ggc cat gaa gtc att tcc    1031
Thr Phe Leu Pro Leu Arg Thr Arg Ser Cys Gly His Glu Val Ile Ser
    290                 295                 300 tgc ctc act gtc agt gaa tcg ggt acc ttc cta ggc cta ggc acg gtc    1079
Cys Leu Thr Val Ser Glu Ser Gly Thr Phe Leu Gly Leu Gly Thr Val
305                 310                 315                 320 act ggc tct gtc gcc atc tac ata gct ttc tct ctc cag cgc ctg tat    1127
Thr Gly Ser Val Ala Ile Tyr Ile Ala Phe Ser Leu Gln Arg Leu Tyr
                325                 330                 335 tat gtg aag gag gcc cat ggc att gtg gtg aca gat gtg acc ttt cta    1175
Tyr Val Lys Glu Ala His Gly Ile Val Val Thr Asp Val Thr Phe Leu
            340                 345                 350 cct gag aag ggt tgc ggt cca aag ctc ctt ggg ccc cat gaa acg gcc    1223
Pro Glu Lys Gly Cys Gly Pro Lys Leu Leu Gly Pro His Glu Thr Ala
        355                 360                 365 ctg ttc tct gtg gct gtg gat agt cgt tgc cag ttg cac ctg ctg ccc    1271
Leu Phe Ser Val Ala Val Asp Ser Arg Cys Gln Leu His Leu Leu Pro
    370                 375                 380 tca cgg cgg agt gtt ccc gta tgg ctc ctg ctc ctg cta tgt gtt ggc    1319
Ser Arg Arg Ser Val Pro Val Trp Leu Leu Leu Leu Leu Cys Val Gly
385                 390                 395                 400 ctt att atc gtg acc atc ctg ctg ctc cag agt gcc ttc ccg ggg ttt    1367
Leu Ile Ile Val Thr Ile Leu Leu Leu Gln Ser Ala Phe Pro Gly Phe
                405                 410                 415 ctt taa catcctgacc aatgggagtc atccttggac agtactacct tctggagcag    1423
Leu * agtcattgag gcccatgact gaagctgcat ctgatgaaat ggatgggtac tgccggtccc    1483
tgctaaacgc tgcgccagtg gcctccctat cactctgggt cttgggagcc ctgctttcac    1543
ctgtggatcc atttaagaca gtgtggtctg aagctcaggc cacactgcct gcctcgtttc    1603
ctctgcctcc cagggctcca gagccgagct cttcctagga acatgtgaag atgccaaaga    1663
gcccagaggc attgccatcc ttctcgcaga gactgttttt cctcctcccc ttccagtctg    1723
cgcacaaggt cctcagcttt gtcgagacaa agtctgtgga agaggcaaaa ggaagaccca    1783
ggtagcggtg atctgtaggt agcacccagc cagtcaggcc agacgcacag ggagttcctg    1843
ggtgacctac tgcagcctga ggaaagggaa agtgaacctc agtttattag gcaggaagag    1903
ttgatattta ataaagaaag a                                              1924
```

<210> SEQ ID NO 2
<211> LENGTH: 417
<212> TYPE: PRT
<213> ORGANISM: Rat

<400> SEQUENCE: 2

```
Met Gly Arg Arg Arg Gly Val Glu Leu Tyr Arg Ala Pro Phe Pro Leu
1               5                  10                  15

Tyr Ala Leu Arg Ile Asp Pro Lys Thr Gly Leu Leu Ile Ala Ala Gly
            20                  25                  30

Gly Gly Gly Ala Ala Lys Thr Gly Ile Lys Asn Gly Val His Phe Leu
        35                  40                  45

Gln Leu Glu Leu Ile Asn Gly Cys Leu Ser Ala Ser Leu Leu His Ser
    50                  55                  60

His Asp Thr Glu Thr Arg Ala Thr Met Asn Leu Ala Leu Ala Gly Asp
65                  70                  75                  80

Ile Leu Ala Ala Gly Gln Asp Ala Gln Cys Gln Leu Leu Arg Phe Gln
```

-continued

```
                    85                  90                  95
Val His Gln Gln Lys Gly Ser Lys Ala Glu Lys Ser Gly Ser Lys Glu
                100                 105                 110

Gln Gly Pro Arg Gln Arg Lys Gly Ala Pro Pro Ala Glu Lys Lys Ser
            115                 120                 125

Gly Ala Gln Val His Pro Glu Gly Val Glu Leu Lys Val Lys Asn Leu
130                 135                 140

Glu Ala Val Gln Thr Asp Phe Ser Asn Glu Pro Leu Gln Lys Val Val
145                 150                 155                 160

Cys Phe Asn His Asp Asn Thr Leu Leu Ala Thr Gly Gly Thr Asp Gly
                165                 170                 175

His Val Arg Val Trp Lys Val Pro Ser Leu Glu Lys Val Leu Glu Phe
            180                 185                 190

Lys Ala His Glu Gly Glu Ile Gly Asp Leu Ala Leu Gly Pro Asp Gly
            195                 200                 205

Lys Leu Val Thr Val Gly Trp Asp Phe Lys Ala Ser Val Trp Gln Lys
210                 215                 220

Asp Gln Leu Val Thr Gln Leu Gln Trp Gln Glu Asn Gly Pro Thr Ser
225                 230                 235                 240

Ser Asn Thr Pro Tyr Arg Tyr Gln Ala Cys Arg Phe Gly Gln Val Pro
                245                 250                 255

Asp Gln Pro Gly Gly Leu Arg Leu Phe Thr Val Gln Ile Pro His Lys
            260                 265                 270

Arg Leu Arg Gln Pro Pro Cys Tyr Leu Thr Ala Trp Asp Ser Ser
            275                 280                 285

Thr Phe Leu Pro Leu Arg Thr Arg Ser Cys Gly His Glu Val Ile Ser
            290                 295                 300

Cys Leu Thr Val Ser Glu Ser Gly Thr Phe Leu Gly Leu Gly Thr Val
305                 310                 315                 320

Thr Gly Ser Val Ala Ile Tyr Ile Ala Phe Ser Leu Gln Arg Leu Tyr
                325                 330                 335

Tyr Val Lys Glu Ala His Gly Ile Val Val Thr Asp Val Thr Phe Leu
            340                 345                 350

Pro Glu Lys Gly Cys Gly Pro Lys Leu Leu Gly Pro His Glu Thr Ala
            355                 360                 365

Leu Phe Ser Val Ala Val Asp Ser Arg Cys Gln Leu His Leu Leu Pro
370                 375                 380

Ser Arg Arg Ser Val Pro Val Trp Leu Leu Leu Leu Cys Val Gly
385                 390                 395                 400

Leu Ile Ile Val Thr Ile Leu Leu Gln Ser Ala Phe Pro Gly Phe
                405                 410                 415

Leu
```

<210> SEQ ID NO 3
<211> LENGTH: 299
<212> TYPE: DNA
<213> ORGANISM: Human
<220> FEATURE:
<221> NAME/KEY: unsure
<222> LOCATION: (255)...(255)

<400> SEQUENCE: 3

```
agatggctac gtccgtgtct ggaaggtgcc cagcctgtag aaggttctgg agttcaaagc    60
ccacgaaggg aggattgaag acctggcttt agggcctgat ggcaagttgg taaccgtggg   120
```

-continued

```
ccgggacctt aaggcctctg tgtggcagaa ggatcagctg gtgacacagc tgcactggca      180
agaaaatgga cccaccttttt ccagcacacc ttaccgctac cagggcctgc aggttttggc    240
aggttccaga ccagnctgct ggccttgcga cttttttacag tgcaaatttt cccacaagc    299
```

<210> SEQ ID NO 4
<211> LENGTH: 17
<212> TYPE: DNA
<213> ORGANISM: Human

<400> SEQUENCE: 4

```
ctccttgggc cccatga                                                     17
```

<210> SEQ ID NO 5
<211> LENGTH: 11
<212> TYPE: DNA
<213> ORGANISM: Human

<400> SEQUENCE: 5

```
ataaactgag g                                                           11
```

<210> SEQ ID NO 6
<211> LENGTH: 20
<212> TYPE: DNA
<213> ORGANISM: Human

<400> SEQUENCE: 6

```
agcagagtca ttgaggccca                                                  20
```

<210> SEQ ID NO 7
<211> LENGTH: 19
<212> TYPE: DNA
<213> ORGANISM: Human

<400> SEQUENCE: 7

```
ttttgcctct tccacagac                                                   19
```

<210> SEQ ID NO 8
<211> LENGTH: 7
<212> TYPE: RNA
<213> ORGANISM: Artificial Sequence
<220> FEATURE:
<223> OTHER INFORMATION: KOZAK consensus sequence

<400> SEQUENCE: 8

```
accaugg                                                                 7
```

<210> SEQ ID NO 9
<211> LENGTH: 7
<212> TYPE: RNA
<213> ORGANISM: Human

<400> SEQUENCE: 9

```
gggaugg                                                                 7
```

<210> SEQ ID NO 10
<211> LENGTH: 16
<212> TYPE: DNA
<213> ORGANISM: Human

<400> SEQUENCE: 10

```
tcgacggggc ggggcc                                                      16
```

```
<210> SEQ ID NO 11
<211> LENGTH: 38
<212> TYPE: DNA
<213> ORGANISM: Human

<400> SEQUENCE: 11
tcgactggct ccagccatga ataaatgtat agggaaag                              38

<210> SEQ ID NO 12
<211> LENGTH: 2072
<212> TYPE: DNA
<213> ORGANISM: Human
<220> FEATURE:
<221> NAME/KEY: CDS
<222> LOCATION: (145)...(1398)
<223> OTHER INFORMATION: deduced coding sequence

<400> SEQUENCE: 12 tgcaactcc  ccggtgtgag  agggtaggg   agtgctcccg  gcggcgacgg  ggccgagttc     60
accagccgcc gggcagtag   tcgaaggccc  ggcgcggcat  gtcctgggtg  ccgcggtgcg    120
ggcagtgaac gcgcgccggg cgggatgggc  cggcgccggg  cgccagagct  gtaccgggct    180
                                  Met Gly Arg Arg Arg Ala Pro Glu Leu
                                    1               5 ccgttcccgt tgtacgcgct tcaggtcgac  cccagcactg  gctgctcat   cgctgcgggc    240
Tyr Arg Ala Pro Phe Pro Leu Tyr  Ala Leu Gln Val Asp Pro Ser Thr
 10              15              20                  25 ggaggaggcg ccgccaagac aggcataaag  aatggcgtgc  actttctgca  gctagagctg    300
Gly Leu Leu Ile Ala Ala Gly Gly  Gly Ala Ala Lys Thr Gly Ile
         30              35                  40 attaatgggc gcttgagtgc ctccttgctg cactcccatg  acacagagac  acgggccacc    360
Lys Asn Gly Val His Phe Leu Gln  Leu Glu Leu Ile Asn Gly Arg Leu
             45              50                  55 atgaacttgg cactggctgg tgacatcctt gctgcagggc aggatgccca ctgtcagctc       420
Ser Ala Ser Leu Leu His Ser His  Asp Thr Glu Thr Arg Ala Thr Met
     60              65                  70 ctgcgcttcc aggcacatca acagcagggc aacaaggcag agaaggccgg ttccaaggag       480
Asn Leu Ala Leu Ala Gly Asp Ile  Leu Ala Ala Gly Gln Asp Ala His
 75              80                  85 cagggcctc  gacaaaggaa gggagcagcc ccagcagaga agaaatgtgg agcggaaacc       540
Cys Gln Leu Leu Arg Phe Gln Ala  His Gln Gln Gly Asn Lys Ala
 90              95                  100                 105 cagcacgagg ggctagaact cagggtagag aatttgcagg cggtgcagac agactttagc       600
Glu Lys Ala Gly Ser Lys Glu Gln  Gly Pro Arg Gln Arg Lys Gly Ala
         110             115                 120 tccgatccac tgcagaaagt tgtgtgcttc aaccacgata taccctgct  tgccactgga       660
Ala Pro Ala Glu Lys Lys Cys Gly  Ala Glu Thr Gln His Glu Gly Leu
 125             130                 135 ggaacagatg gctacgtccg tgtctggaag gtgcccagcc tggagaaggt tctggagttc       720
Glu Leu Arg Val Glu Asn Leu Gln  Ala Val Gln Thr Asp Phe Ser Ser
 140             145                 150 aaagcccacg aagggagat  tgaagacctg gctttagggc ctgatggcaa gttggtaacc       780
Asp Pro Leu Gln Lys Val Val Cys  Phe Asn His Asp Asn Thr Leu Leu
     155             160                 165 gtgggccggg accttaaggc ctctgtgtgg cagaaggatc agctggtgac acagctgcac       840
Ala Thr Gly Gly Thr Asp Gly Tyr  Val Arg Val Trp Lys Val Pro Ser
170              175             180                 185 tgcaagaaa  atggacccac cttttccagc acaccttacc gctaccaggc ctgcaggttt       900
Leu Glu Lys Val Leu Glu Phe Lys  Ala His Glu Gly Glu Ile Glu Asp
             190             195                 200 gggcaggttc cagaccagcc tgctggcctg cgactcttca cagtgcaaat tccccacaag       960
Leu Ala Leu Gly Pro Asp Gly Lys  Leu Val Thr Val Gly Arg Asp Leu
```

| | |
|---|---|
| cgcctgcgcc agcccctcc ctgctacctc acagctgggg atggctccaa cttcttgccc<br>Lys Ala Ser Val Trp Gln Lys Asp Gln Leu Val Thr Gln Leu His Trp<br>    220                        225                        230 | 1020 |
| cttcggacca agtcctgtgg ccatgaagtc gtctcctgcc tcgatgtcag tgaatccggc<br>Gln Glu Asn Gly Pro Thr Phe Ser Ser Thr Pro Tyr Arg Tyr Gln Ala<br>    235                        240                        245 | 1080 |
| accttcctag gcctgggcac agtcactggc tctgttgcca tctacatagc tttctctctc<br>Cys Arg Phe Gly Gln Val Pro Asp Gln Pro Ala Gly Leu Arg Leu Phe<br>250                  255                        260                        265 | 1140 |
| cagtgcctct actacgtgag ggaggcccat ggcattgtgg tgacggatgt ggcctttcta<br>Thr Val Gln Ile Pro His Lys Arg Leu Arg Gln Pro Pro Pro Cys Tyr<br>    270                        275                        280 | 1200 |
| cctgagaagg gtcgtggtcc agagctcctt gggtcccatg aaactgccct gttctctgtg<br>Leu Thr Ala Trp Asp Gly Ser Asn Phe Leu Pro Leu Arg Thr Lys Ser<br>    285                        290                        295 | 1260 |
| gctgtggaca gtcgttgcca gctgcatctg ttgccctcac ggcggagtgt tcctgtgtgg<br>Cys Gly His Glu Val Val Ser Cys Leu Asp Val Ser Glu Ser Gly Thr<br>    300                        305                        310 | 1320 |
| ctcctgctcc tgctgtgtgt cgggcttatt attgtgacca tcctgctgct ccagagtgcc<br>Phe Leu Gly Leu Gly Thr Thr Gly Ser Val Ala Ile Tyr Ile Ala<br>    315                        320                        325 | 1380 |
| tttccaggtt tcctttagct tccctgcttc ctgggaatca ggagcctgga cactgccatc<br>Phe Ser Leu Gln Cys Leu Tyr Tyr Val Arg Glu Ala His Gly Ile Val<br>330                  335                        340                        345 | 1440 |
| tctagagcag agtggaggcc tggactccct ttgctcactc cattcgggtc cacagctgag<br>Val Thr Asp Val Ala Phe Leu Pro Glu Lys Gly Arg Gly Pro Glu Leu<br>    350                        355                        360 | 1500 |
| gttgcctctg acaagatgaa tgggcactgc ctgcccttct agtgaaaagg cttggctatg<br>Leu Gly Ser His Glu Thr Ala Leu Phe Ser Val Ala Val Asp Ser Arg<br>    365                        370                        375 | 1560 |
| gccctgtgtg actccaggtc ccaggaacct tgccttcgtc atctgtggat ccatccagaa<br>Cys Gln Leu His Leu Leu Pro Ser Arg Arg Ser Val Pro Val Trp Leu<br>    380                        385                        390 | 1620 |
| cagcggtatc tgaagcccag gccatactcc ctgcctcctt tcttctgcct accagaggct<br>Leu Leu Leu Leu Cys Val Gly Leu Ile Ile Val Thr Ile Leu Leu Leu<br>    395                        400                        405 | 1680 |
| ccagagttga gcttgtcctt atctagaaac atgtgaagat gcccaagagc ctggaggcac<br>Gln Ser Ala Phe Pro Gly Phe Leu  *<br>410                415 | 1740 |
| tgctgtcctt cctgcagaaa cagtttctcc tcctcccctc agccttgtgg ccagttcctc | 1800 |
| ttcacatgaa gcccctggca tttgctgggg aagggactgg cctggtactt gctgttaggg | 1860 |
| caggaagggg caaaggaag acttgggtag taatctgggg gttcagatgg gtagcactaa | 1920 |
| gccagctggc ctaaagatgc aataagttcc taggtagtct acccttacct tgaggaatgg | 1980 |
| gaaaatgaac ctcagcccat taggcaggaa aagttgatat ttaataaaca aggaaagagt | 2040 |
| gaacttgaga ccccaaaaaa aaaaaaaaaa aa | 2072 |

<210> SEQ ID NO 13
<211> LENGTH: 417
<212> TYPE: PRT
<213> ORGANISM: Human

<400> SEQUENCE: 13

Met Gly Arg Arg Arg Ala Pro Glu Leu Tyr Arg Ala Pro Phe Pro Leu
1               5                    10                   15

Tyr Ala Leu Gln Val Asp Pro Ser Thr Gly Leu Leu Ile Ala Ala Gly
                 20                    25                   30

Gly Gly Gly Ala Ala Lys Thr Gly Ile Lys Asn Gly Val His Phe Leu
            35                  40                  45

Gln Leu Glu Leu Ile Asn Gly Arg Leu Ser Ala Ser Leu Leu His Ser
 50                  55                  60

His Asp Thr Glu Thr Arg Ala Thr Met Asn Leu Ala Leu Ala Gly Asp
 65                  70                  75                  80

Ile Leu Ala Ala Gly Gln Asp Ala His Cys Gln Leu Leu Arg Phe Gln
                85                  90                  95

Ala His Gln Gln Gln Gly Asn Lys Ala Glu Lys Ala Gly Ser Lys Glu
                100                 105                 110

Gln Gly Pro Arg Gln Arg Lys Gly Ala Pro Ala Glu Lys Lys Cys
                115                 120                 125

Gly Ala Glu Thr Gln His Glu Gly Leu Glu Leu Arg Val Glu Asn Leu
            130                 135                 140

Gln Ala Val Gln Thr Asp Phe Ser Ser Asp Pro Leu Gln Lys Val Val
145                 150                 155                 160

Cys Phe Asn His Asp Asn Thr Leu Leu Ala Thr Gly Gly Thr Asp Gly
                165                 170                 175

Tyr Val Arg Val Trp Lys Val Pro Ser Leu Glu Lys Val Leu Glu Phe
                180                 185                 190

Lys Ala His Glu Gly Glu Ile Glu Asp Leu Ala Leu Gly Pro Asp Gly
            195                 200                 205

Lys Leu Val Thr Val Gly Arg Asp Leu Lys Ala Ser Val Trp Gln Lys
            210                 215                 220

Asp Gln Leu Val Thr Gln Leu His Trp Gln Glu Asn Gly Pro Thr Phe
225                 230                 235                 240

Ser Ser Thr Pro Tyr Arg Tyr Gln Ala Cys Arg Phe Gly Gln Val Pro
                245                 250                 255

Asp Gln Pro Ala Gly Leu Arg Leu Phe Thr Val Gln Ile Pro His Lys
                260                 265                 270

Arg Leu Arg Gln Pro Pro Cys Tyr Leu Thr Ala Trp Asp Gly Ser
            275                 280                 285

Asn Phe Leu Pro Leu Arg Thr Lys Ser Cys Gly His Glu Val Val Ser
 290                 295                 300

Cys Leu Asp Val Ser Glu Ser Gly Thr Phe Leu Gly Leu Gly Thr Val
305                 310                 315                 320

Thr Gly Ser Val Ala Ile Tyr Ile Ala Phe Ser Leu Gln Cys Leu Tyr
                325                 330                 335

Tyr Val Arg Glu Ala His Gly Ile Val Val Thr Asp Val Ala Phe Leu
                340                 345                 350

Pro Glu Lys Gly Arg Gly Pro Glu Leu Leu Gly Ser His Glu Thr Ala
            355                 360                 365

Leu Phe Ser Val Ala Val Asp Ser Arg Cys Gln Leu His Leu Leu Pro
 370                 375                 380

Ser Arg Arg Ser Val Pro Val Trp Leu Leu Leu Leu Cys Val Gly
385                 390                 395                 400

Leu Ile Ile Val Thr Ile Leu Leu Gln Ser Ala Phe Pro Gly Phe
                405                 410                 415

Leu

<210> SEQ ID NO 14
<211> LENGTH: 18
<212> TYPE: DNA

-continued

```
<213> ORGANISM: Human

<400> SEQUENCE: 14
atgtcctggg tgccgcgg                                                         18

<210> SEQ ID NO 15
<211> LENGTH: 19
<212> TYPE: DNA
<213> ORGANISM: Human

<400> SEQUENCE: 15
tgaaacgagt acaacggga                                                        19

<210> SEQ ID NO 16
<211> LENGTH: 1912
<212> TYPE: DNA
<213> ORGANISM: Human
<220> FEATURE:
<221> NAME/KEY: CDS
<222> LOCATION: (145)...(1197)
<223> OTHER INFORMATION: deduced coding sequence

<400> SEQUENCE: 16
tggcaactcc ccggtgtgag aggggtaggg agtgctcccg gcggcgacgg ggccgagttc           60
accagccgcc ggggcagtag tcgaaggccc ggcgcggcat gtcctgggtg ccgcggtgcg          120
ggcagtgaac gcgcgccggg cggg atg ggc cgg cgc cgg gcg cca gag ctg             171
                          Met Gly Arg Arg Arg Ala Pro Glu Leu
                            1               5 tac cgg gct ccg ttc ccg ttg tac gcg ctt cag gtc gac ccc agc act            219
Tyr Arg Ala Pro Phe Pro Leu Tyr Ala Leu Gln Val Asp Pro Ser Thr
 10                  15                  20                  25 ggg ctg ctc atc gct gcg ggc gga ggc gcc gcc aag aca ggc ata                267
Gly Leu Leu Ile Ala Ala Gly Gly Gly Ala Ala Lys Thr Gly Ile
             30                  35                  40 aag aat ggc gtg cac ttt ctg cag cta gag ctg att aat ggg cgc ttg            315
Lys Asn Gly Val His Phe Leu Gln Leu Glu Leu Ile Asn Gly Arg Leu
         45                  50                  55 agt gcc tcc ttg ctg cac tcc cat gac aca gag aca cgg gcc acc atg            363
Ser Ala Ser Leu Leu His Ser His Asp Thr Glu Thr Arg Ala Thr Met
     60                  65                  70 aac ttg gca ctg gct ggt gac atc ctt gct gca ggg cag gat gcc cac            411
Asn Leu Ala Leu Ala Gly Asp Ile Leu Ala Ala Gly Gln Asp Ala His
 75                  80                  85 tgt cag ctc ctg cgc ttc cag gca cat caa cag cag ggc aac aag gca            459
Cys Gln Leu Leu Arg Phe Gln Ala His Gln Gln Gln Gly Asn Lys Ala
 90                  95                 100                 105 gag aag gcc ggt tcc aag gag cag ggg cct cga caa agg aag gga gca            507
Glu Lys Ala Gly Ser Lys Glu Gln Gly Pro Arg Gln Arg Lys Gly Ala
             110                 115                 120 gcc cca gca gag aag aaa tgt gga gcg gaa acc cag cac gag ggg cta            555
Ala Pro Ala Glu Lys Lys Cys Gly Ala Glu Thr Gln His Glu Gly Leu
         125                 130                 135 gaa ctc agg gta gag aat ttg cag gcg gtg cag aca gac ttt agc tcc            603
Glu Leu Arg Val Glu Asn Leu Gln Ala Val Gln Thr Asp Phe Ser Ser
     140                 145                 150 gat cca ctg cag aaa gtt gtg tgc ttc aac cac gat aat acc ctg ctt            651
Asp Pro Leu Gln Lys Val Val Cys Phe Asn His Asp Asn Thr Leu Leu
 155                 160                 165 gcc act gga gga aca gat ggc tac gtc cgt gtc tgg aag gtg ccc agc            699
Ala Thr Gly Gly Thr Asp Gly Tyr Val Arg Val Trp Lys Val Pro Ser
 170                 175                 180                 185
```

```
ctg gag aag gtt ctg gag ttc aaa gcc cac gaa ggg gag att gaa gac      747
Leu Glu Lys Val Leu Glu Phe Lys Ala His Glu Gly Glu Ile Glu Asp
            190                 195                 200 ctg gct tta ggg cct gat ggc aag ttg gta acc gtg ggc cgg gac ctt      795
Leu Ala Leu Gly Pro Asp Gly Lys Leu Val Thr Val Gly Arg Asp Leu
        205                 210                 215 aag gcc tct gtg tgg cag aag gat cag ctg gtg aca cag ctg cac tgg      843
Lys Ala Ser Val Trp Gln Lys Asp Gln Leu Val Thr Gln Leu His Trp
    220                 225                 230 caa gaa aat gga ccc acc ttt tcc agc aca cct tac cgc tac cag gcc      891
Gln Glu Asn Gly Pro Thr Phe Ser Ser Thr Pro Tyr Arg Tyr Gln Ala
235                 240                 245 tgc agg ttt ggg cag gtt cca gac cag cct gct ggc ctg cga ctc ttc      939
Cys Arg Phe Gly Gln Val Pro Asp Gln Pro Ala Gly Leu Arg Leu Phe
250                 255                 260                 265 aca gtg caa att ccc cac aag cgc ctg cgc cag ccc cct ccc tgc tac      987
Thr Val Gln Ile Pro His Lys Arg Leu Arg Gln Pro Pro Pro Cys Tyr
        270                 275                 280 ctc aca gcc tgg gat ggc tcc aac ttc ttg ccc ctt cgg acc aag tcc     1035
Leu Thr Ala Trp Asp Gly Ser Asn Phe Leu Pro Leu Arg Thr Lys Ser
    285                 290                 295 tgt ggc cat gaa gtc gtc tcc tgc ctc gat gtc agt gaa tcc ggc acc     1083
Cys Gly His Glu Val Val Ser Cys Leu Asp Val Ser Glu Ser Gly Thr
300                 305                 310 ttc cta ggc ctg ggc aca gtc act ggc tct gtt gcc atc tac ata gct     1131
Phe Leu Gly Leu Gly Thr Val Thr Gly Ser Val Ala Ile Tyr Ile Ala
        315                 320                 325 ttc tct ctc cag gga gtg ttc ctg tgt ggc tcc tgc tcc tgc tgt gtg     1179
Phe Ser Leu Gln Gly Val Phe Leu Cys Gly Ser Cys Ser Cys Cys Val
330                 335                 340                 345 tcg ggc tta tta ttg tga ccatcctgct gctccagagt gcctttccag            1227
Ser Gly Leu Leu Leu *
            350 gtttccttta gcttccctgc ttcctgggaa tcaggagcct ggacactgcc atctctagag   1287 cagagtggag gcctggactc cctttgctca ctccattcgg gtccacagct gaggttgcct   1347 ctgacaagat gaatgggcac tgcctgccct tctagtgaaa aggcttggct atggccctgt   1407 gtgactccag gtcccaggaa ccttgccttc gtcatctgtg gatccatcca gaacagcggt   1467 atctgaagcc caggccatac tccctgcctc ctttcttctg cctaccagag gctccagagt   1527 tgagcttgtc cttatctaga aacatgtgaa gatgcccaag agcctggagg cactgctgtc   1587 cttcctgcag aaacagtttc tcctcctccc ctcagccttg tggccagttc ctcttcacat   1647 gaagcccctg gcatttgctg gggaagggac tggcctggta cttgctgtta gggcaggaag   1707 gggcaaaagg aagacttggg tagtaatctg ggggttcaga tgggtagcac taagccagct   1767 ggcctaaaga tgcaataagt tcctaggtag tctacccttg ccttgaggaa tgggaaaatg   1827 aacctcagcc cattaggcag gaaaagttga tatttaataa acaaggaaag agtgaacttg   1887 agaccccaaa aaaaaaaaaa aaaaa                                         1912

<210> SEQ ID NO 17
<211> LENGTH: 350
<212> TYPE: PRT
<213> ORGANISM: Human

<400> SEQUENCE: 17

Met Gly Arg Arg Arg Ala Pro Glu Leu Tyr Arg Ala Pro Phe Pro Leu
 1               5                  10                  15
```

```
Tyr Ala Leu Gln Val Asp Pro Ser Thr Gly Leu Leu Ile Ala Ala Gly
             20                  25                  30
Gly Gly Gly Ala Ala Lys Thr Gly Ile Lys Asn Gly Val His Phe Leu
         35                  40                  45
Gln Leu Glu Leu Ile Asn Gly Arg Leu Ser Ala Ser Leu Leu His Ser
     50                  55                  60
His Asp Thr Glu Thr Arg Ala Thr Met Asn Leu Ala Leu Ala Gly Asp
 65                  70                  75                  80
Ile Leu Ala Ala Gly Gln Asp Ala His Cys Gln Leu Leu Arg Phe Gln
                 85                  90                  95
Ala His Gln Gln Gln Gly Asn Lys Ala Glu Lys Ala Gly Ser Lys Glu
            100                 105                 110
Gln Gly Pro Arg Gln Arg Lys Gly Ala Ala Pro Ala Glu Lys Lys Cys
        115                 120                 125
Gly Ala Glu Thr Gln His Glu Gly Leu Glu Leu Arg Val Glu Asn Leu
    130                 135                 140
Gln Ala Val Gln Thr Asp Phe Ser Ser Asp Pro Leu Gln Lys Val Val
145                 150                 155                 160
Cys Phe Asn His Asp Asn Thr Leu Leu Ala Thr Gly Gly Thr Asp Gly
                165                 170                 175
Tyr Val Arg Val Trp Lys Val Pro Ser Leu Glu Lys Val Leu Glu Phe
            180                 185                 190
Lys Ala His Glu Gly Glu Ile Glu Asp Leu Ala Leu Gly Pro Asp Gly
        195                 200                 205
Lys Leu Val Thr Val Gly Arg Asp Leu Lys Ala Ser Val Trp Gln Lys
    210                 215                 220
Asp Gln Leu Val Thr Gln Leu His Trp Gln Glu Asn Gly Pro Thr Phe
225                 230                 235                 240
Ser Ser Thr Pro Tyr Arg Tyr Gln Ala Cys Arg Phe Gly Gln Val Pro
                245                 250                 255
Asp Gln Pro Ala Gly Leu Arg Leu Phe Thr Val Gln Ile Pro His Lys
            260                 265                 270
Arg Leu Arg Gln Pro Pro Pro Cys Tyr Leu Thr Ala Trp Asp Gly Ser
        275                 280                 285
Asn Phe Leu Pro Leu Arg Thr Lys Ser Cys Gly His Glu Val Val Ser
    290                 295                 300
Cys Leu Asp Val Ser Glu Ser Gly Thr Phe Leu Gly Leu Gly Thr Val
305                 310                 315                 320
Thr Gly Ser Val Ala Ile Tyr Ile Ala Phe Ser Leu Gln Gly Val Phe
                325                 330                 335
Leu Cys Gly Ser Cys Ser Cys Val Ser Gly Leu Leu Leu
            340                 345                 350

<210> SEQ ID NO 18
<211> LENGTH: 4521
<212> TYPE: DNA
<213> ORGANISM: Human
<220> FEATURE:
<221> NAME/KEY: promoter
<222> LOCATION: (1)...(714)
<221> NAME/KEY: exon
<222> LOCATION: (715)...(993)
<221> NAME/KEY: intron
<222> LOCATION: (994)...(1560)
<221> NAME/KEY: exon
<222> LOCATION: (1561)...(1750)
<221> NAME/KEY: intron
```

```
<222> LOCATION: (1751)...(1942)
<221> NAME/KEY: exon
<222> LOCATION: (1943)...(2163)
<221> NAME/KEY: intron
<222> LOCATION: (2164)...(2356)
<221> NAME/KEY: exon
<222> LOCATION: (2357)...(2437)
<221> NAME/KEY: intron
<222> LOCATION: (2438)...(2552)
<221> NAME/KEY: exon
<222> LOCATION: (2553)...(2677)
<221> NAME/KEY: intron
<222> LOCATION: (2678)...(2876)
<221> NAME/KEY: exon
<222> LOCATION: (2877)...(3050)
<221> NAME/KEY: intron
<222> LOCATION: (3051)...(3198)
<221> NAME/KEY: exon
<222> LOCATION: (3199)...(3271)
<221> NAME/KEY: intron
<222> LOCATION: (3272)...(3449)
<221> NAME/KEY: exon
<222> LOCATION: (3450)...(3609)
<221> NAME/KEY: intron
<222> LOCATION: (3610)...(3772)
<221> NAME/KEY: exon
<222> LOCATION: (3773)...(4521)
<221> NAME/KEY: unsure
<222> LOCATION: (1796)...(1796)
<221> NAME/KEY: unsure
<222> LOCATION: (2846)...(2846)

<400> SEQUENCE: 18
ggatccccat gttgcccagg ctgtctcgaa agcctgggct caagccatcc tcctctctcg      60
gactttccga aagtgttggg attacaggag gattacaggc atgaaccacc gtgcctggca     120
gaggattttt ttttttttg agacggagtt tcactcttgt tgcttgttgc ccaggctgaa     180
gagcaatggc aatggcgcga tctcggctca ctgcaacctc tacttcccag gttcaagtga     240
ttctcctgcc tcaggctccc gagtagctgg gattacaggc gcacgccacc acgcccttg     300 tattttggt agagacgggg tttctccatg ttggtcaggc tggtctcgaa ctcctgatcc     360
gcccgcctag gactcacaaa gtgctgggat tacaggcgcg agtcggattt ctttattaaa     420
ggttgacctt catcaacctc cattgggtcc acctcctccg cccgcgcccc gcgcccgca     480 caaaaatggc gaagtcggtg ctgggcgact ctgcctccgc gccaggggtg gagaaccgaa     540
gccccgcccc gggaaacgcc ccccgcggc cggctagtgc tgacgcgtgt cggcgctcct     600
gcgcctgcgc ggagggagcc gcgagacagg tgcgcatgcg caatgcgcgt ctgcgagaac     660
gacttggacg ggagccgacc tgaggctccg cttcctgctg atggtcaagg gttttggcaa     720
ctccccggtg tgagaggggt agggagtgct cccggcggcg acgggccga gttcaccagc      780 cgccggggca gtagtcgaag gcccggcgcg gcatgtcctg ggtgccgcgg tgcgggcagt     840
gaacgcgcgc cggcgggat gggccggcgc cgggcgccag agctgtaccg ggctccgttc      900
ccgttgtacg cgcttcaggt cgaccccagc actgggctgc tcatcgctgc gggcggagga     960
ggcgccgcca agacaggcat aaagaatggc gtggtgagag cgcagggcca ctggggctgg    1020
gtcttgctgc gggctggcgg cgattccaag gtggccgggg ggtcgcgggg cgggccacac    1080
tccagcttcg ggccctgccc acttctgttg ggaagacccg cttgcctgac gcccagggc     1140 gaatttcagt cgagaactca ggcgggcgga ggagaggctt ttaaggtaaa gtgaaaactg    1200
cacacagctg cagagtcgcg aggaacgctt cagctccgcc tcagaacagc tccagggtc     1260 ttatactggc cttttccggg aggtcttgcc tgccctctag cagcggcgag agtggtgcat    1320
ttgggtttaa gctaagttcc ttccctctcc tgagcttaac ctgttctgta aaataaaggt    1380
```

```
aataatccca atcctgctca ctgtgtatat ttgtgaggcc caaatgagaa aaaaaagact    1440
cgagaaaacc ttgtgaacta aaacgtgcaa aaaacaaaag gggtaaaaca tcagactctt    1500
ccctaaacgt gctctctggg gcacccctga aattgctcat ccgggttccc cctcccacag    1560
cactttctgc agctagagct gattaatggg cgcttgagtg cctccttgct gcactcccat    1620
gacacagaga cacgggccac catgaacttg gcactggctg gtgacatcct tgctgcaggg    1680
caggatgccc actgtcagct cctgcgcttc caggcacatc aacagcaggg caacaaggca    1740
gagaaggccg gttgaggact ccctttttac cccctttggg aaaggttgaa acgagnaagt    1800
cactctttgt gtctctaaag aagttggtct tgaagtaggt tttgtagcaa gctagaagtt    1860
gtttgggcac ctgccattgg agaggagggg ccagtactcc ttactgtaga agcttgaacc    1920
tggccaagtg tttgtgttac aggttccaag gagcagggc ctcgacaaag gaagggagca    1980
gccccagcag agaagaaatg tggagcggaa acccagcacg aggggctaga actcagggta    2040
gagaatttgc aggcggtgca gacagacttt agctccgatc cactgcagaa agttgtgtgc    2100
ttcaaccacg ataatccct gcttgccact ggaggaacag atggctacgt ccgtgtctgg    2160
aaggtgtggg tttgcagggt tagggagggt gaatgtcagt agcaacagga tcaaaattgt    2220
gagaagttga acgtggcatc tgggaaactt gtgaatgaag cttgcattga ggggccatta    2280 gaagggtgg cgtgggcatc agtcacagtg tacttgctgg acacctgagt taaccatggt    2340
ggttgtttgg ctacaggtgc ccagcctgga aaggttctg gagttcaaag cccacgaagg    2400
ggagattgaa gacctggctt tagggcctga tggcaaggtg aggggctggg ggtgggagga    2460
ggatggagaa aggagagagg aggtgcttat gctgcttgcc cagtaagtgg atcccctaac    2520
tgtccatcct tggaatcttt attcctaact agttggtaac cgtgggccgg gaccttaagg    2580
cctctgtgtg gcagaaggat cagctggtga cacagctgca ctggcaagaa aatggaccca    2640
ccttttccag cacaccttac cgctaccagg cctgcaggtg tgaagacttt ggggggtggc    2700
tgaaagaggc atagcccagc tgtggtgggg gagagggaaa agactgggga tgggagagct    2760
ggggaggaac ttgttgagtg ttaccccagg tctgaccagg gtgcaggtgg tgcacaaacc    2820
tctgaggagg gttgggcagg ccctangagc tgaataaccc ctcatccggc ccccaggttt    2880
gggcaggttc cagaccagcc tgctggcctg cgactcttca cagtgcaaat tccccacaag    2940
cgcctgcgcc agccccctcc ctgctacctc acagcctggg atggctccaa cttcttgccc    3000
cttcggacca agtcctgtgg ccatgaagtc gtctcctgcc tcgatgtcag gtgttagaca    3060
ttgctgcctt gggctaggta gggggtccct gagggagctt ggaaaggagt cctgcctggg    3120
tccctacgga ccggtattgg ggtatgaggg ttgctgcaca agcctccagg acaatgagct    3180
ctttattgtt tgttgcagtg aatccggcac cttcctaggc ctgggcacag tcactggctc    3240
tgttgccatc tacatagctt tctctctcca ggtaatgggt ggaggttggc atggccctgt    3300
gggtggactg taggcctgtc tctaccctga gtttgcagga aggagtctgg cccatcctat    3360
cgagggaaat cctgggggtg gggaacatgc tttccagaaa gagagttccc agctaggcct    3420
ttcctcactg gtattccttc tgcccacagt gcctctacta cgtgagggag gcccatggca    3480
ttgtggtgac ggatgtggcc tttctacctg agaaggtcg tggtccagag ctccttgggt    3540
cccatgaaac tgccctgttc tctgtggctg tggacagtcg ttgccagctg catctgttgc    3600
cctcacggcg tgagtcattg gggcagggca ggcaggcacc accccacgtt taatgaccag    3660
aaacgtgccc cccggaggct gggctctttg tgccactcct cctttgaagg gttctggttt    3720
```

-continued

```
tcaggctggg aagcccttttt gcccgctgac ctcctccctt tccctcctgc agggagtgtt      3780
cctgtgtggc tcctgctcct gctgtgtgtc gggcttatta ttgtgaccat cctgctgctc      3840
cagagtgcct ttccaggtttt cctttagctt ccctgcttcc tgggaatcag gagcctggac      3900
actgccatct ctagagcaga gtggaggcct ggactcactt tgctcactcc attcgggtcc      3960
acagctgagg ttgcctctga caagatgaat gggcactgcc tgcccttcta gtgaaaaggc      4020
ttggctatgg ccctgtgtga ctccaggtcc caggaacctt gccttcgtca tctgtggatc      4080
catccagaac agcggtatct gaagcccagg ccatactccc tgcctccttt cttctgccta      4140
ccagaggctc cagagttgag cttgtcctta tctagaaaca tgtgaagatg cccaagagcc      4200
tggaggcact gctgtccttc ctgcagaaac agtttctcct cctcccctca gccttgtggc      4260
cagttcctct tcacatgaag cccctggcat tgctgggga agggactggc ctggtacttg       4320
ctgttagggc aggaaggggc aaaaggaaga cttgggtagt aatctggggg ttcagatggg      4380
tagcactaag ccagctggcc taaagatgca ataagttcct aggtagtcta cccttacctt      4440
gaggaatggg aaaatgaacc tcagcccatt aggcaggaaa agttgatatt taataaacaa      4500
ggaaagagtg aacttgagac c                                                4521
```

```
<210> SEQ ID NO 19
<211> LENGTH: 20
<212> TYPE: DNA
<213> ORGANISM: Human

<400> SEQUENCE: 19
ctcggcttcc tgctgatggt                                                    20

<210> SEQ ID NO 20
<211> LENGTH: 19
<212> TYPE: DNA
<213> ORGANISM: Human

<400> SEQUENCE: 20
caagcgggtc ttcccaaca                                                     19

<210> SEQ ID NO 21
<211> LENGTH: 22
<212> TYPE: DNA
<213> ORGANISM: Human

<400> SEQUENCE: 21
cagactcttc cctaaacgtg ct                                                 22

<210> SEQ ID NO 22
<211> LENGTH: 21
<212> TYPE: DNA
<213> ORGANISM: Human

<400> SEQUENCE: 22
acttactggg caagcagcat a                                                  21

<210> SEQ ID NO 23
<211> LENGTH: 20
<212> TYPE: DNA
<213> ORGANISM: Human

<400> SEQUENCE: 23
cccacgaagg ggagattgaa                                                    20
```

```
<210> SEQ ID NO 24
<211> LENGTH: 20
<212> TYPE: DNA
<213> ORGANISM: Human

<400> SEQUENCE: 24
gggcacgttt ctggtcatta                                            20

<210> SEQ ID NO 25
<211> LENGTH: 22
<212> TYPE: DNA
<213> ORGANISM: Human

<400> SEQUENCE: 25
ctttgaaggg ttctggtttt ca                                         22

<210> SEQ ID NO 26
<211> LENGTH: 26
<212> TYPE: DNA
<213> ORGANISM: Human

<400> SEQUENCE: 26
ggtctcagtt cactctttcc ttgttt                                     26

<210> SEQ ID NO 27
<211> LENGTH: 18
<212> TYPE: DNA
<213> ORGANISM: Human

<400> SEQUENCE: 27
atgtcctggg tgccgcgg                                              18

<210> SEQ ID NO 28
<211> LENGTH: 19
<212> TYPE: DNA
<213> ORGANISM: Human

<400> SEQUENCE: 28
tgaaacgcgt acaacggga                                             19

<210> SEQ ID NO 29
<211> LENGTH: 18
<212> TYPE: DNA
<213> ORGANISM: Human

<400> SEQUENCE: 29
cagcagagaa gaaatgtg                                              18

<210> SEQ ID NO 30
<211> LENGTH: 22
<212> TYPE: DNA
<213> ORGANISM: Human

<400> SEQUENCE: 30
tggtagcggt aaggtgtgct gg                                         22
```

PROLACTIN REGULATORY ELEMENT BINDING PROTEIN AND USES THEREOF

Priority is claimed to U.S. Provisional Patent Application Ser. No. 60/125,728, filed Mar. 23, 1999.

The present invention involves subject matter developed under National Institute of Health Grants Numbered GM36847 and DA07859, so that the United States Government may have certain rights herein.

1. INTRODUCTION

The present invention relates to isolated nucleic acids encoding Prolactin Regulatory Element Binding (PREB) protein and recombinant proteins encoded thereby. The nucleic acid sequences are useful in the production of recombinant PREB, as probes, and in the control of prolactin gene expression. In particular embodiments of the invention, PREB nucleic acid sequences are used to detect transcripts of the gene in astrocytomas. The PREB protein is associated with the kinase-mediated hormonal regulation of prolactin gene expression, and may be used as a trans-acting control of transcription.

2. BACKGROUND OF THE INVENTION
2.1. FUNCTION OF THE PROLACTIN HORMONE

Prolactin (PRL) is an anterior pituitary hormone that is part of a family of hormones. Prolactin was discovered in 1928 based on the ability of pituitary extracts to cause lactation in pseudo-pregnant rabbits. Cooke, N. E., and Leibhaber, S. A., 1995, *Vitamins and Hormones* 50:385–459. Accumulated data now suggest a very broad spectrum of roles for PRL. PRL is linked to over three-hundred separate actions in vertebrates including effects on water and salt balance, growth and development, metabolism, brain behavior, reproduction, and immune regulation and protection. Bole-Feysot C. et al.,1998, *Endocr. Rev.* June; 19(3):225–268. Additionally, a number of disease states, including the growth of different forms of cancer as well as various autoimmune diseases, appear to be related to an overproduction of PRL. Bole-Feysot C. et al., 1998, *Endocr. Rev.* June; 19(3):225–268.

Studies have shown that female transgenic mice overexpressing the rat PRL gene all develop mammary carcinomas at 11–15 months of age and male transgenic mice over-expressing PRL develop dramatic enlargement of the prostate gland. Wennbo H. et al., 1997, *J. Clin. Invest.* December 1; 100 (11):2744–2751. The effect of PRL on cell proliferation was studied in a mouse mammary tumor cell line. The results of the study indicated that PRL antiserum is able to inhibit cell growth by 70% suggesting that PRL may be acting as a local growth factor that stimulates the proliferation of mammary tumors. Mersho, J. et al., 1995, *Endocrinology.* August; 136(8):3619–3623. Similarly, human breast cancer cells synthesize and secrete biologically active PRL and there is evidence to support that PRL may be involved in an autocrine/paracrine stimulatory loop within breast tissues that may play a role in the pathogenesis of breast cancer. Clevenger C. V. et al., 1995, *Am. J Pathol.* March; 146(3):695–705.

In addition, PRL is produced by leukocytes and fibroblasts and animal model studies suggest that increased levels of serum PRL may influence the course of arthritis, lupus, and autoimmune type I diabetes, indicating that PRL may play a role in autoimmune diseases and the regulation of immune responses. Neidhart, M., 1998, *Proc. Soc. Exp. Biol. Med.* April; 217(4):408–419. Ferrag, F. et al., 1997, *Cytokines Cell Mol Ther.* September; 3(3):197–213. There an important aspect of therapeutic approaches with respect to these diseases is the understanding of the regulation of PRL expression.

2.2. TISSUE SPECIFIC EXPRESSION OF PROLACTIN

The prolactin gene appears to function as an important element in tissue-specific and developmentally regulated gene expression. Cooke, N. E. and Liebhaber, S. A., 1995, *Vitamins and Hormones* 50:385–459. Prolactin is expressed in a cell-type specific fashion in pituitary lactotropic cells. Cooke, N. E. and Liebhaber, S. A., 1995, *Vitamins and Hormones* 50:385–459. In addition, prolactin expression has been found in human endometrial cells, human breast tissue, human mammary cell lines, human ovaries, human immune system cells and tissues (thymus, spleen, tonsil, lymph node, lymphocytes, and lymphoid tumors), epithelial cells, vascular endothelial cells, hypothalamic cells, and in human decidua-chorion. Tanaka, S. et al., 1996, *Eur. J Endocrinol.* 135(2):177–183; Shaw-Bruha, C. M., 1997, *Breast Cancer Res. Treat.* 44(3):243–253; Schwarzler, P. et al., 1997, *Fertil. Steril.* 68(4):696–701; Wu, H. et al., 1996, *Endocrinology* 137(1):349–353; Clapp, C. et al., 1994, *Proc. Natl. Acad. Sci. USA* 91(22):10384–10388; Clements, J., 1983, *Endocrinology* 112(3):1133–1134. Among human tissues which do not express prolactin are lung and kidney as well as many others. Schwarzler, P. et al., 1997, *Fertil. Steril* 68(4):696–701. Although it has been shown that prolactin is expressed in a tissue dependent manner, it is not clear which transcription factors are responsible. While Pit-1, the POU homeo-domain transcription factor (a variant of the helix-turn-helix type transcription factor), gene expression has been shown to follow levels of prolactin expression, Pit-1 is expressed in 3 cell types of the pituitary (thyrotropic cells, lactotropic cells, somoatotropic cells, somatolactortropic cells) while prolactin is primarily expressed in lactotropic cells. Crenshaw, E. B. et al., 1989, *Genes Dev.* 3(7):959–972. The mechanism of tissue specific expression of prolactin is still being investigated.

2.3. PRL REGULATION

Transcription factors are proteins that bind to regulatory elements in genes and have a critical role in gene regulation and protein expression during development, cellular growth and differentiation. Transcription factors generally can be categorized into four major groups according to the motif in their DNA-binding domains which include (1) the helix-turn-helix group, (2) the zinc finger group, (3) the leucine zipper group, and (4) the helix-loop-helix group. Lloyd, R. V. and Osamura, R. Y., 1997, *Microsc. Res. Tech.* 3 9(2):168–181.

The prolactin promoter contains multiple binding sites implicated in basal PRL expression and in kinase-mediated hormonal regulation of the gene. The pituitary-specific transcription factor Pit-1 has been shown to play an important role in the expression by the pituitary of the prolactin gene both in development and in the mature organism. Iverson, R. A. et al., 1990, *Mol. Endocrinol.* 4:1564–1571. Okimura, Y. et al., 1994, *Mol. Endocrinol.* 8:1559–1565. Although Pit-1 binds to many of the binding sites in the PRL promoter, it does not appear to be responsible for kinase-mediated hormonal regulation of PRL. Fischberg, D. J. et al., 1994, Mol. Endocrinol. 8:1566–1573; Okimura, Y. et al., 1994, Mol. Endocrinol. 8:1559–1565; Howard, P. W. and Maurer, R. A., 1994, *J Biol. Chem.* 269:28662–28669. This suggests that there are factors other than Pit-1 that are responsible for the regulation of PRL gene expression.

Oct-1 and TEF are two other transcription factors which can bind to the promoter of the PRL gene. Voss, J. W. et al., 1991, *Genes Dev.* 5:1309–1320; Drolet, D. W. et al., 1991,

*Genes Dev.* 5:1739–1753. Studies show that Oct-1 is unlikely to be involved in the kinase-mediated transcription of the prolactin gene since protein kinase A (PKA)-mediated phosphorylation of Oct-1 decreases its DNA binding activity. Segil, N. et al., 1991, *Science 254:1814–1816*. Additionally, TEF is not likely to be involved in the kinase-mediated transcription of the prolactin gene since its mode of action is apparently limited to thyrotroph development. Voss, J. W. et al., 1991, *Genes Dev.* 5:1309–1320.

Mutations in the Pit1 gene, observed in the naturally occurring Snell (dw) and Jackson (dwJ) mutant mice, result in a murine phenotype of severe growth retardation and a remarkably hypoplastic pituitary gland, due to a developmental failure of the three anterior pituitary cell types that specifically express the hormones regulated by Pit1. See Li et al., *Nature* 347:528–533 (1990). Mutations in the human homologue of Pit1 have also been shown to be responsible for deficiencies of these three pituitary hormones, and to result in a human phenotype of growth abnormalities, severe mental retardation, failure of lactation, congenital hypoparathyroidism, facial dysmorphism and hypoplastic pituitary. See Radovick et al, *Science* 57:1115–1118 (1992); Tatsumi et al., *Nat. Genet.* 1:56–58 (1992); de Zegher et al, *J Clin. Endocr. Metab.* 80:3127–3130 (1995).

Despite evidence that PRL gene expression is highly regulated and induced by the cAMP-protein kinase-A pathway, a transcription factor involved in the kinase-mediated transcription of the prolactin gene has been, prior to the present invention, elusive. Keech, C. A. et al., 1992, *Mol Endocrinol* 6(12):2059–2070. Evidence suggests that there is a ubiquitous transcription factor that is involved in the PKA-mediated transcriptional activation pathway of prolactin. Rajnarayan, S. et al., 1995, *Mol Endocrinol* 9(4) :502–512. A better understanding of the PKA-mediated transcriptional activation pathway, coupled to more effective means to control this pathway, could lead to the treatment of ailments that are related to the inappropriate expression of the prolactin gene.

2.4 TREATMENT OF DISEASE THROUGH PROLACTIN REGULATION

Since its discovery in 1928, PRL has been implicated in a broad spectrum of roles including regulation of reproductive function, control of metabolism, osmoregulation, and immune regulation, as well as growth and development in certain vertebrate species. Nicoll, C. S., 1991, *Perspect. Biol. Med.* 25:369–381. In addition to becoming well known as an important regulator of immune function, a number of disease states, including different forms of cancer, autoimmune diseases, developmental diseases and osteoporosis have been connected to the overproduction of PRL. Yu-Lee, L-y., 1997, *Proc. Soc. Exp. Biol. Med.* 215:35–52; Adler et al., *Metabolism*, 47:425–428 (1998).

PRL expression has been detected in human mammary tumors, and human mammary tumor cell lines can produce PRL, indicating a possible auto/paracrine function of PRL in mammary tumor growth. Wennbo, H. et al., 1997, *J. Clin. Invest.* 100:2744–2751. In addition, inhibitors of the proliferation of human breast cancer cells in vitro appear to inhibit endogenous prolactin action at the level of the prolactin receptor and antibodies to PRL inhibit the proliferation of rat mammary tumor cells in vitro. De Petrocellis, L. et al., 1998, *Proc Natl. Acad. Sci. USA* 95(14):8375–8380; Mersho, J. et al., 1995, *Endocrinology* 136(8):3619–3623. Furthermore, tamoxifen, an anti-estrogen which is known for its anti-tumoral action in vivo, inhibits PRL-induced activation of kinases as well as PRL binding and cell growth indicating the possible role of PRL inhibition in the treatment of breast cancer. Das, R. and Vonderhaar, B. K., 1997, *Cancer Letters* 116(1):41–46. Another study aimed at further characterizing the role of prolactin in breast cancer has focused on the creation of transgenic mice that over-express prolactin. Significantly, all of the female mice which over-expressed PRL developed mammary carcinomas at 11–15 months of age. Wennbo, H. et al., 1997, *J. Clin. Invest.* 100:2744–2751. In the same study, organ culture experiments were conducted which demonstrated an autocrine/paracrine effect of PRL.

The role of PRL in human breast cancer has been suggested in a study that reports two cases of breast cancer associated with prolactinoma. Strungs, I. et al., 1997, *Pathology* 29(3):320–323. Correspondingly, male mice which over-expressed PRL developed dramatic enlargement of the prostate gland, approximately 20 times the normal size. Wennbo, H. et al., 1997, *Endocrinology* 138(10) 4410–4415. It is interesting to note that the level of PRL increases with age, coinciding with development of prostate hyperplasia in humans. Hammond, G. L. et al., 1997, *Clin. Endocrinol.* 7:129–135. It appears therefore that PRL may be an important factor in the etiology of prostate diseases including cancer. All the aforementioned studies are in strong support of the notion that PRL may be an important target in the quest to control cancer.

PRL has also been implicated in autoimmune diseases. PRL, as well as growth hormone, is required for the development of mature lymphocytes and for the maintenance of immunocompetence. Berczi, I., 1997, *Acta Paediatr Suppl.* 423:70–75. It is suggested that hyperprolactinemia is a risk factor for the development of autoimmunity. There are many studies that support a role of PRL in modulating the immune response and altered PRL levels have been observed in animal models of autoimmune diseases such as lupus erythematosus, diabetes, rheumatoid arthritis, and collagen type II-induced arthritis. Berczi, I., 1983, et al. *Acta. Endocrinol.* 102:351–357; Jara, L. J. et al., 1992, *Am. J. Med. Sci.* 303:222–226; Neidhart, M., 1998, *Proc. Soc. Exp. Biol. Med.* 217(4):408–419. Since PRL constitutes a stimulatory link between the neuroendocrine and immune systems, increased serum levels may activate a hyperimmune response. Neidhart, M., 1998, *Proc. Soc. Exp. Biol. Med.* 217(4):408–419. In these diseases, it may be advantageous to reduce the serum levels of PRL by inhibiting its gene expression. Additionally, serum PRL levels were elevated in human bone transplantation patients which exhibited chronic graft-versus-host disease indicating that prolactin is a mediator of graft-versus-host disease. Hinterberger-Fischer, M. et al., 1994, *Bone Marrow Transplant* 14(3) :403–406. The inhibition of PRL after transplantation may decrease the rejection problems of transplantation patients.

In contrast, an increase in prolactin expression may be beneficial where the immune response is compromised, for example, in AIDS. Recombinant human PRL has been demonstrated to have the ability to stimulate proliferation of B-cell hybridomas in a dose-dependent manner, resulting in an overall increase of antibody production. Richards, S. M. et al., 1998, *Cell. Immunol.* 184(2):85–91. Additionally, PRL was able to overcome the growth inhibition of the hybridoma cells by transforming growth factor beta (TGF-beta), indicating a role for PRL in the treatment of diseases associated with over-expression of TGF-beta, or in AIDS where it may be advantageous to stimulate lymphoid cells. Hinterberger-Fischer, M. et al., 1994, *Bone Marrow Transplant* 14(3):403–406.

PRL may regulate bone marrow function as well. In rats which have their pituitary gland removed, treatments with PRL reversed the anemia, leucopenia, and thrombocytopenia in their bone marrow. Nagy, E. and Berczi, I., 1989, Br. J. Haematol. 71(4):457–462. Moreover, prolactin regulation of the growth of hematopoetic progenitors in a bone marrow stroma environment has been demonstrated in vitro by the addition of PRL antibodies to cultures resulting in a reduction of hematopoetic progenitor colonies. Bellone, G., 1997, et al. Blood 90(1):21–27. These findings suggest that over-expression of prolactin may be used to stimulate the growth of hematopoetic progenitor cells in vitro which may ultimately be transplanted into a patient.

Studies have also linked PRL overproduction with osteoporosis. Humans with prolactinoma are at risk for reproductive disorders and osteoporosis which may be due to PRL-induced hypogonadism. See Adler et al., *Metabolism* 47:425–428 (1998). In addition, anovulation condition (which is an estrogen deficiency due to high prolactin levels) is linked with premature bone mass loss. See Koloszar et al., *Orv. Hetil.* 138:71–73 (1997). It has been suggested that osteopathy in hyperprolactinemic hypogonadism is due to reduced bone formation and not reduced estradiol production, indicating a link of PRL levels with bone formation. See Rozhinskaia et al., *Probl. Endokrinol.* 38:17–19 (1992). Similarly, Ciccarelli et al. (*Clin. Enndocrinol.* 28:1–6 (1988)) have suggested that there is a direct effect of PRL on bone mass. The risk of developing osteoporosis due to increased levels of PRL has been seen in women as well as in men. See Jackson et al., *Ann Intern. Med.* 105:543–545 (1986).

3. SUMMARY OF THE INVENTION

The present invention relates to the discovery of a novel transcription factor, called PREB (Prolactin Regulatory Element Binding) protein which functions in the kinase-mediated hormonal regulation of prolactin gene expression. The invention is based, at least in part, on the discovery and characterization of the rat Preb gene and protein and the identification of a cloned human DNA containing the human PREB gene.

In a first series of embodiments, the present invention provides for a nucleic acid molecule encoding PREB, and a PREB protein having an amino acid sequence as encoded by that nucleic acid which binds to the 1P element of the PRL promoter.

In a second set of embodiments, the present invention provides for a method of inhibiting kinase-mediated transactivation of prolactin gene expression.

In a third set of embodiments, the present invention provides for an assay for distinguishing between different brain tumor types whereby PREB transcript levels are quantified. For example, but not by way of limitation, PREB transcript levels can be quantified using a PREB nucleic acid sequence as a probe, by RT-PCR analysis or by microarray analysis. The presence of PREB would indicate the presence of astrocytoma brain tumor cells but not neuroepithelioma or glioma brain tumor cells.

In a fourth set of embodiments, the present invention provides for methods for the treatment of cancers and autoimmune diseases through the inhibition of prolactin gene expression.

In a fifth set of embodiments, the present invention provides for methods for improving the immune response by increasing prolactin gene expression.

In a sixth set of embodiments, the present invention provides for a method for inhibiting Pit-1-mediated transactivation of prolactin gene expression and the transactivation of other genes whose transcriptional activation is controlled by Pit-1.

In a seventh set of embodiments, the present invention provides for methods for stimulating the growth of cells both in vitro and in vivo through the over-expression of genes by the use of promoter sequences which are regulated by the binding of the PREB transcription factor. This method is also useful in the culture of skin cells or bone marrow cells in vitro which will ultimately be transplanted into a patient.

In an eighth set of embodiments, the present invention provides for a method for inhibiting graft-versus-host disease in transplant patients through the inhibition of prolactin gene expression.

In a ninth set of embodiments, the present invention provides for a method for controlling development through the inhibition of PREB expression.

In a tenth set of embodiments, the present invention provides for a nucleic acid encoding human PREB, as contained in plasmid pCRScript (Stratagene) deposited with the American Type Culture Collection (10801 University Blvd., Manassas, Va. 20110–2209 USA) and assigned accession number PTA1259. The present invention also provides for two genomic fragments, which encompass the PREB gene minus 500 bp from the 3' UTR that is within the cDNA transcript, of 1.6 kb and 2.5 kb respectively, which were deposited with the American Type Culture Collection (10801 University Blvd., Manassas, Va. 20110–2209 USA) and assigned accession numbers PTA1258 and PT01260 respectively.

In an eleventh set of embodiments, the present invention provides for a method of detecting trisomy 2p whereby a PREB nucleic acid sequence is used as a probe. The presence of additional copies of PREB would indicate a trisomy 2p condition.

In a twelfth set of embodiments, the present invention provides for a method of detecting an increased propensity to develop osteoporosis whereby any change in the expression of PREB which results in activation or inactivation of the PREB protein would indicate a propensity to develop osteoporosis. For example, changes which could indicate an increased propensity to develop osteoporosis include, but are not limited to, (1) changes in the PREB gene, such as heterozygous or homozygous partial or total deletions of the PREB gene, insertions, base pair changes, mutations, etc.; (2) changes in the transcript levels; and/or (3) changes in the PREB protein levels and truncations of the PREB protein (which may be the result of a mutation in the PREB gene) which could result in an up-regulation of certain pathways.

In a thirteenth set of embodiments, the present invention provides for a method of treating osteoporosis, or lowering the likelihood of developing osteoporosis comprising administering the PREB gene or gene product, including, but not limited to antisense PREB mRNA, or the PREB protein, to a subject.

4. DESCRIPTION OF THE FIGURES

FIGS. 1A & B. (A) a map of the protein; (B) nucleic acid sequence of rat Preb cDNA (SEQ ID NO:1) and deduced amino acid sequence (SEQ ID NO:2).

FIG. 2. Nucleic acid sequence of Homo sapiens cDNA clone R12741 (SEQ ID NO:3).

FIGS. 3A–C. DNA target site for PREB. (A) Partially purified poly-His-tagged PREB (40 ng) protein was incubated with a $^{32}$[P]-site 1P probe, plus or minus excess (50–250 fold) of the indicated competitors, and analyzed on polyacrylamide gels. Lane 1 received no added protein, and lanes 1–11 and 12–23 were analyzed on separate gels. To improve resolution, the free probe was run off the end of the gel. The single major shifted band observed with PREB is indicated. (B) Structure of site 1P and sequences mutated in competitors *1P and 1P*, and region predicted to form part of the binding site for PREB. The bases shown by X-ray crystallography structure analysis to be contacted by Pit-1 POU domain dimers (Jacobson et al. *Genes Dev.* 11:198–212. 1997) are bracketed. (C) Schematic of nucleotide sequences of 1P, *1P, 1P*, *1P*, and 3P.

FIGS. 4A–D. Southern blot analysis of the PREB gene in various organisms (A) Rat, (B) Human, (C) Drosophila, and (D) Yeast. DNA isolated from the organisms was digested with the indicated restriction enzymes, and subjected to Southern blot analysis, employing a PREB cDNA probe. Hybridization was at reduced stringency (39° C.), except for rat DNA, where stringent conditions were employed. The sizes of internal DNA molecular weight markers are indicated.

FIGS. 5A–D. Size and nuclear accumulation of PREB in GH3 cells. (A) Nuclei and cytosol were prepared, and the nuclei extracted with 0.42 mM KCl. Nuclear and cytosolic proteins from an equal number of cells were then analyzed on a Western blot, employing anti-PREB antiserum. Sizes of marker proteins on the same gel are indicated. The same antiserum was employed for immunocytochemistry of (B) GH3 cells with Antibody, (C) GH3 cells with pre-immune serum or (D) C6 cells. Ab, anti-PREB antiserum; Pre, preimmune serum from the same animal.

Figure 6:
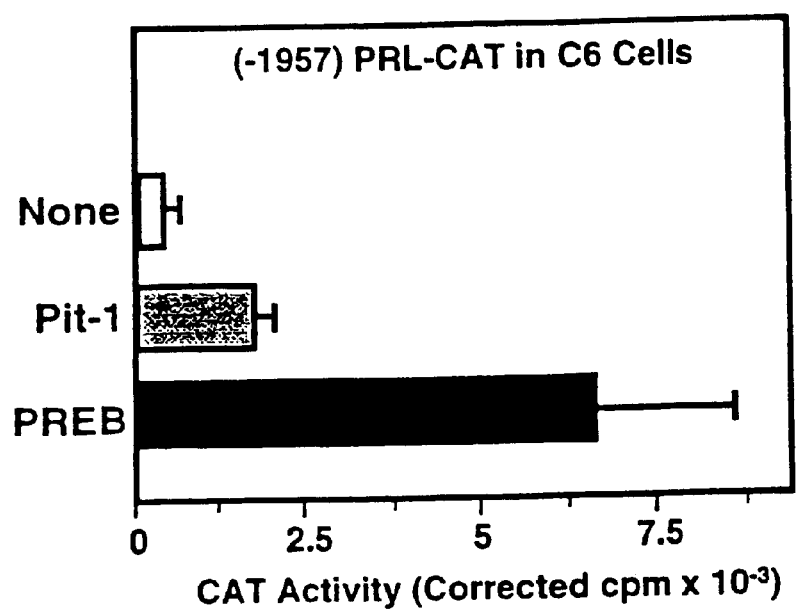

FIG. 6. PREB can transactivate expression directed by the prolactin promoter plus enhancer. C6 rat glial cells ($2.6 \times 10^6$) were electroporated with (–1957) PRL–CAT (10 µg) plus RSV-βgal (2 µg), plus 5 µg either RcRSV ("None"), or RSV-Pit-1 or RSV–PREB, divided into three 60 mm dishes, incubated two days, and then assayed for CAT and β-galactosidase activity. Shown is the mean ±standard deviation (SD) of CAT activity, corrected for β-galactosidase activity, observed with triplicate dishes.

Figure 7:
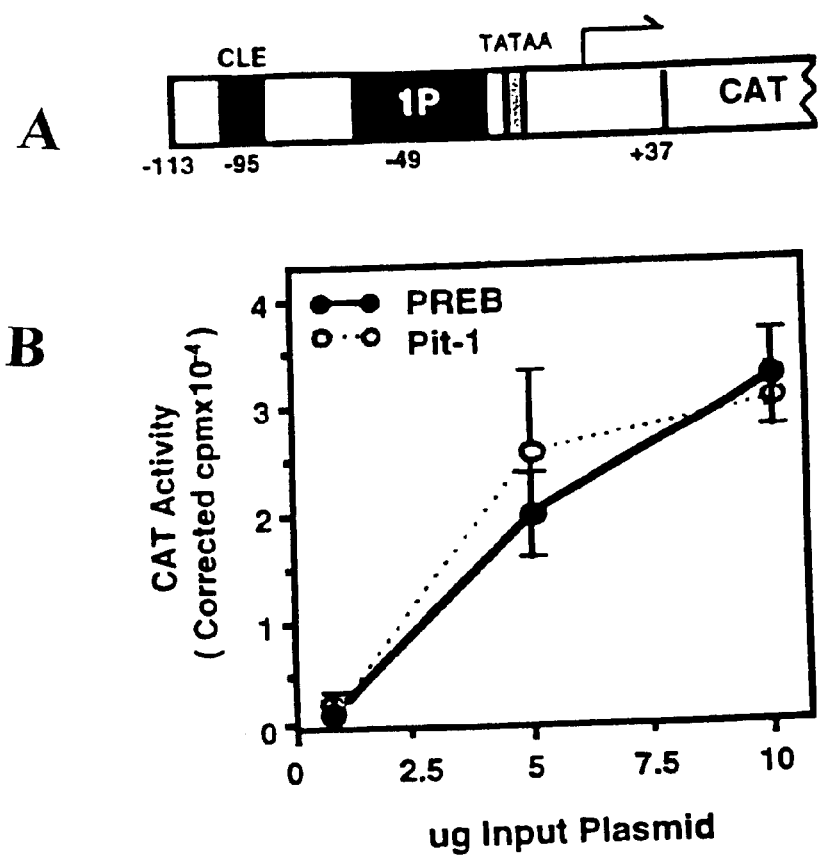

FIGS. 7A & B. PREB and Pit-1 yield equivalent activation of expression of prolactin promoter construct. (A) Structure of plasmid (–113)PRL–CAT, illustrating the positions of the known prolactin promoter elements. (B) C6 cells ($2.6 \times 10^6$) were electroporated with (–113)PRL–CAT (10 µg) and RSV-βgal (2 µg), plus the indicated amounts of either RSV-Pit-1 or RSV–PREB, and treated thereafter as in FIG. 6. Shown is the mean ±SD of corrected CAT activity observed with triplicate dishes.

Figure 8:
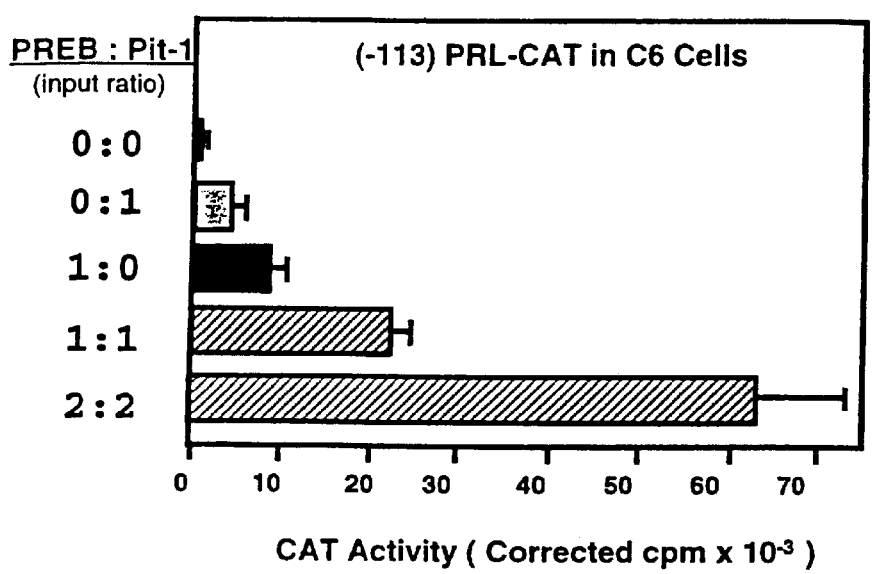

FIG. 8. PREB and Pit-1 exhibit additive stimulation of a prolactin promoter construct. C6 cells were electroporated with (–113)PRL–CAT and RSV-βgal as in FIG. 7, plus the indicated amounts of RSV–PREB and/or RSV-Pit-1 (1=2.5 µg plasmid), and treated thereafter as in FIG. 6. Shown is the mean ±SD of corrected CAT activity observed with triplicate dishes.

Figure 9:
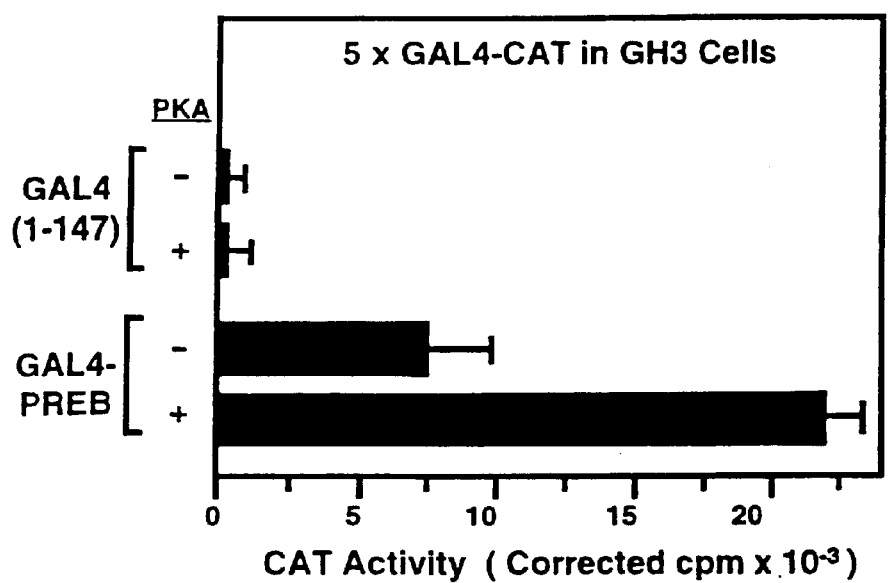

FIG. 9. PREB can support a PKA-mediated transcriptional response in pituitary cells. $GH_3$ rat pituitary cells were electroporated with 5XGAL4–CAT (10 µg) and RSV-βgal (2 µg), plus 5 µg either pGAL4 (1–147) or GAL4–PREB, plus 5 µg either RcRSV (PKA–) or RSV–PKA (PKA+) and treated thereafter as in FIG. 6. Shown is the mean ±SD of corrected CAT activity observed with triplicate dishes.

Figure 10:
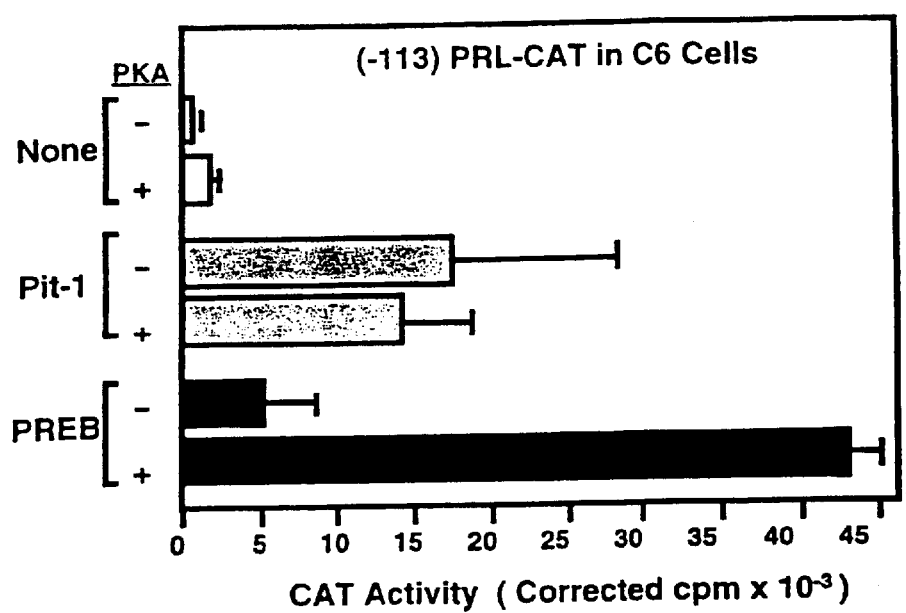

FIG. 10. PREB, but not Pit-1, can mediate regulation by PKA of expression of a prolactin promoter construct. C6 cells were electroporated with (–113)PRL–CAT and RSV-βgal as in FIG. 7, plus 2.5 µg either RcRSV (None), RSV-Pit-1 or RSV–PREB, plus 5 µg either RcRSV (PKA–) or RSV–PKA (PKA+), and treated thereafter as in FIG. 6. Shown is the mean ±SD of corrected CAT activity observed with triplicate dishes.

FIG. 11. Nucleic acid sequence of human PREB cDNA (SEQ ID NO:12) and deduced amino acid sequence (SEQ ID NO:13).

FIG. 12. Species conservation of the PREB WD-repeat Motifs. All amino acids that fall within the WD-repeat consensus are shaded.

Figure 13:
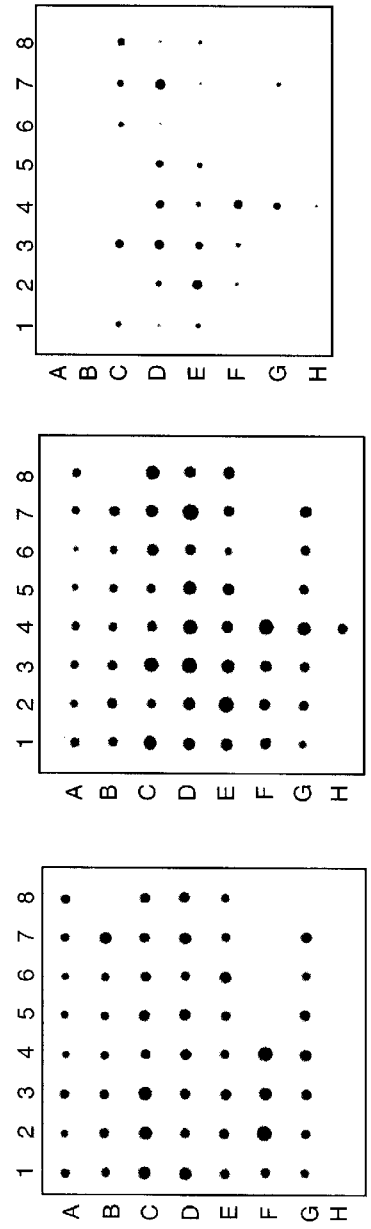
Figure 14:
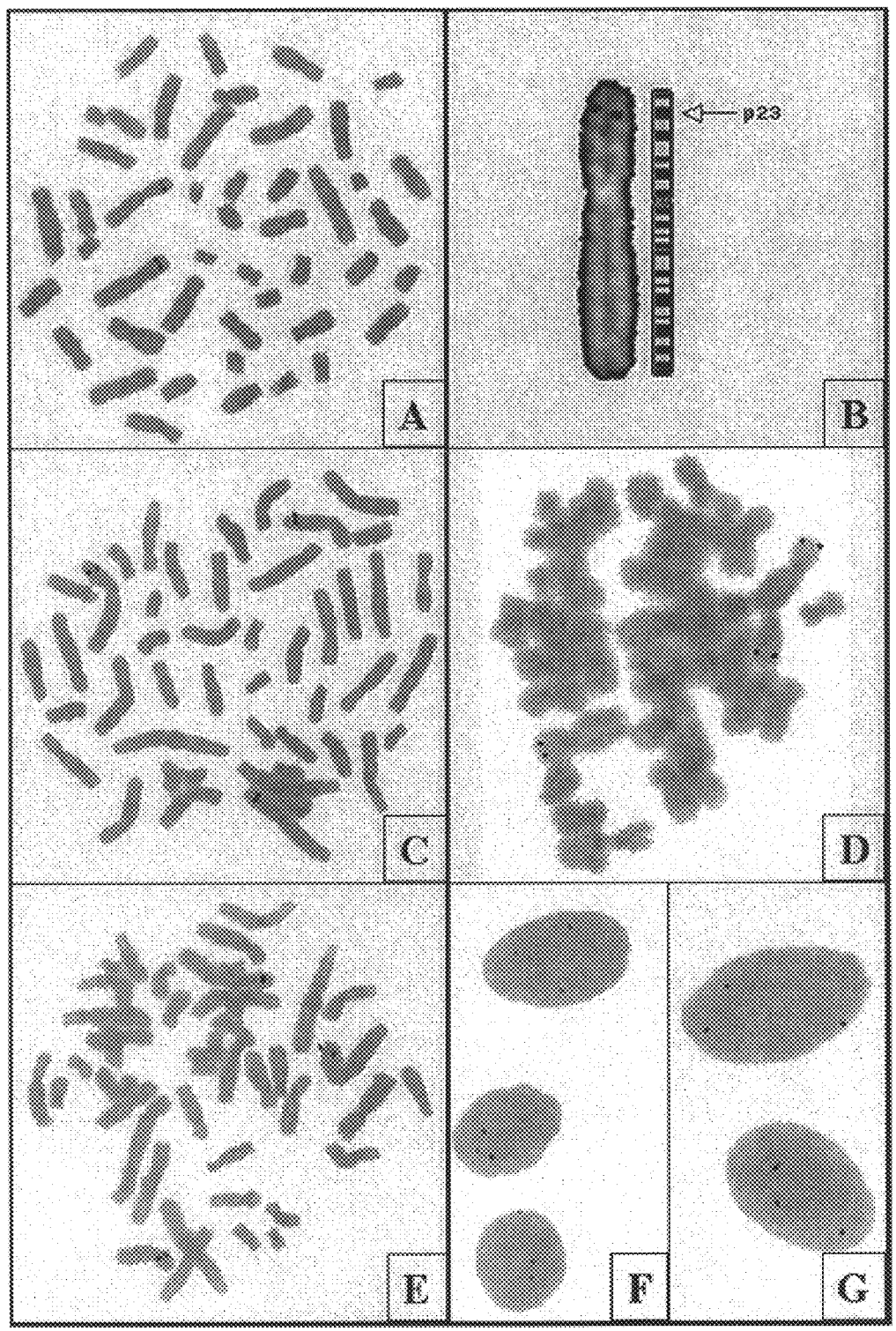

FIGS. 13 A–D. Human PREB gene expression. (A) Key to the human tissue sources represented on the RNA master blot (Clonetech). The mRNA samples in rows A–F originate from 43 adult tissues; samples in row G are derived from seven human fetal tissues; row H contains negative control RNA and DNA samples. (B) Control ubiquitin cDNA hybridization to the RNA filter. (C) Northern analysis with a 350 bp human PREB 3' UTR fragment probe. (D) A shorter exposure of the PREB probe hybridization shown in panel C showing variation among tissues in the levels of PREB expression in adult salivary gland, liver, pancreas and skeletal muscle, and fetal liver tissue.

FIGS. 14A–G. FISH mapping and dosage analysis of PREB. (A) Mapping of the human PREB gene to chromosome 2 by FISH using metaphase chromosomes from normal male lymphocytes. (B) Regional assignment of the FISH signals to 2p23. (C) Metaphase chromosomes from patient A with t(2,11)(p21; q23.3). (D) Metaphase chromosomes from the cell line GM04409 derived from a patient with t(2;14)(p23;q32). (E) Metaphase chromosomes from patient B with t(2;13)(p23;p11.2). (F) Interphase nuclei from the cell line GM04409. (G) Interphase nuclei from patient B.

FIG. 15A. Nucleic acid sequence of human PREB alternative splice variant cDNA (SEQ ID NO:16).

FIG. 15B. Deduced amino acid sequence of human PREB alternative splice variant cDNA (SEQ ID NO:17).

FIG. 16. Genomic nucleic acid sequence of the human PREB gene. Bold-face type indicates exons and nonbold-faced type indicates introns.

FIG. 17. Gene PCR amplification from a nuclear family with low BMD linkage to 2p23-14. Wthidium bromide-stained agarose gel of PCR amplified products using gene-specific primers for PREB (CB301/317; PREB PCR 4), ketohexokinase, osteopontin, and GAPDH. Arrows indicate PCR amplified products of the correct size, determined by a 1kb+DNA ladder. A=Affected mother; B=Unaffected father; C=Affected offspring; E=control DNA sample.

5. DETAILED DESCRIPTION OF THE INVENTION

For purposes of clarity of description, and not by way of limitation, the detailed description of the invention is divided into the following subsections:

(i) the PREB gene and its products;
(ii) diagnostic methods;
(iii) regulation of prolactin gene expression;
(iv) PREB and osteoporosis propensity;
(v) methods of treatment; and
(vi) expression of foreign genes.

5.1 PREB GENE AND ITS PRODUCTS

The present invention relates to nucleic acid molecules which encode a PREB protein capable of increasing expression of prolactin in a pituitary cell., including RNA, DNA, any cDNA or antisense counterparts thereof and any complementary nucleic acid sequences. In particular non-limiting embodiments, the present invention provides for (i) a nucleic acid molecule having a sequence as set forth in SEQ ID NO:1, SEQ ID NO:12, or SEQ ID NO:16; (ii) a nucleic acid molecule which encodes a protein having a sequence as set forth in SEQ ID NO:2, SEQ ID NO:13, or SEQ ID NO:17; (iii) and nucleic acid molecules which hybridize to a nucleic acid molecule of (i) or (ii) under stringent hybridization conditions as set forth below, and which encode a protein that binds to the 1P element of the PRL promoter such that binding results in transactivation of the PRL gene. Stringent hybridization conditions as defined herein include conditions for prehybridization and hybridization, performed at 39° C., according to the Basic Protocol described in Ausubel et al (*Short Protocols in Molecular Biology*, Third Edition, 1995, John Wiley and Sons, Publisher), Unit 2.10, employing a $^{32}$[p]random-primed rat Preb cDNA probe and the aqueous prehybridization/hybridization (APH) solution described in *Short Protocols in Molecular Biology* (Appendix 1), and washing of filters as described in *Short Protocols in Molecular Biology*, Unit 2.10, including the two optional 15 minute moderate-stringency washes described (42° C. 0.2×SSC/ 0.1% SDS).

The term "PREB gene", as used herein, collectively includes the rat Preb gene, its human counterpart (PREB) homologs thereof in other species which are at least ~85%, and preferably ~95%, homologous to the complete rat Preb gene (homology determined by Blast Search Algorithm; Netscape Navigator, 3.01), and alternatively spliced variants of PREB.

In one specific nonlimiting embodiment, the invention provides for a human PREB-encoding nucleic acid sequence as set forth in FIG. 2 (SEQ ID NO:3), which hybridizes to a nucleic acid sequence having SEQ ID NO:1 under stringent hybridization and wash conditions as set forth above, and which human PREB protein encoded thereby binds the human PRL promoter wherein such binding transactivates PRL gene transcription. In a further nonlimiting embodiment, the invention provides for human PREB-encoding nucleic acid sequences as set forth in FIG. 11A (SEQ ID NO:12) and FIG. 15A (SEQ ID NO:16) and the deduced amino acid sequence (SEQ ID NO:13 and SEQ ID NO:17, respectively). The PREB gene of the present invention is involved in PRL regulation and also functions as a DNA-binding transcription factor during mammalian development.

The present invention also provides for PCR primers which may be used to prepare cDNA or genomic DNA corresponding to all, or part of the PREB gene as set forth in the example section below. Such techniques may be used to identify and isolate a nucleic acid molecule encoding the entire PREB protein or mutants thereof.

In a specific, nonlimiting embodiment, the present invention provides for a substantially purified nucleic acid molecule containing a rat Preb encoding cDNA, which has a nucleic acid sequence designated as SEQ ID NO:1 and an amino acid sequence designated as SEQ ID NO:2. The invention also provides for a substantially purified nucleic acid molecule containing a human PREB-encoding cDNA, which has a nucleic acid sequence designated as SEQ ID NO:12 or SEQ ID NO:16 and an amino acid sequence designated as SEQ ID NO:13 or SEQ ID NO:17.

The PREB gene or corresponding cDNA or RNA or any corresponding complementary or anti-sense nucleic acid molecule may be incorporated into any suitable cloning or expression vector, operably linked to appropriate control elements (e.g. promoter elements, enhancer elements, ribosomal binding sites, polyadenylation sites, termination sites, etc.). Examples of such vectors include, but are not limited to, herpes simplex viral based vectors such as pHSV1 (Geller et al., 1990, *Proc. Natl. Acad. Sci.* U.S.A. 87:8950–8954); retroviral vectors such as MFG (Jaffee et al., 1993, *Cancer Res.* 53:2221–2226), and in particular Moloney retroviral vectors such as LN, LNSX, LNCX, LXSN (Miller and Rosman, 1989, *Biotechniques* 7:980–989); vaccinia viral vectors such as MVA (Sutter and Moss, 1992, *Proc. Natl. Acad. Sci.* U.S.A. 89:10847–10851); adenovirus vectors such as pJM17 (Ali et al., 1994, *Gene Therapy* 1:367–384; Berker, 1988, *Biotechniques* 6:616–624; Wand and Finer, 1996, *Nature Medicine* 2:714–716); adeno-associated virus vectors such as AAV/ neo (Mura-Cacho et al., 1992, *J Immunother*. 11:231–237); lentivirus vectors (Zufferey et al., 1997, *Nature Biotechnology* 15:871–875); and plasmid vectors such as pcDNA3 and pcDNA1 (InVitrogen), pET11a, pET3a, pET11d, pET3d, pET22d, pET12a and pET28a (Novagen); plasmid AH5 (which contains the SV40 origin and the adenovirus major late promoter), pRC/CMV (InVitrogen), pCMU II (Paabo et al., 1986, *EMBO J.* 5:1921–1927), pZipNeo SV (Cepko et al., 1984, *Cell* 37:1053–1062), pSRα (DNAX, Palo Alto, Calif.) and pBK-CMV, pSPTg.T2FpAXK and pSPTg.2FXK (Schaleger et al., 1997, *Proc. Natl. Acad. Sci.* U.S.A. 94:3058–3063).

In specific non-limiting embodiments of the invention, a PREB gene or a corresponding cDNA or RNA may be comprised in an expression vector in frame with a second nucleic acid molecule encoding a second protein sequence so as to encode for a fusion protein in which PREB is positioned either C-terminal or N-terminal to the other gene. For example, the second nucleic acid molecule may encode a protein which, when fused with PREB, does not effect the DNA binding activity of PREB but inhibits the DNA binding of other transcription factors which bind to PRL promoter elements in close proximity to PREB (e.g. glutathione-s-transferase, maltose-binding protein, etc). A dominant-negative fusion protein consisting of a transcriptionally defunct PREB fused to the POU DNA binding domain of Pit-1 is also within the scope of the invention. This PREB-Pit-1 fusion may be capable of binding cooperatively to the 1P element with an increased binding affinity as compared to either PREB or Pit-1 alone and may be capable of inhibiting the transactivation of PRL by endogenous PREB and Pit-1. The PREB protein sequence contains two putative transactivation domains (residues 86–134 and 223–279) whose amino acid sequences are rich in proline and glutamine. Proline-rich and glutamine-rich transactivation motifs have been identified in transcription factors. Mitchell, P. J. and R. Tjian, 1989, *Science* 245:371–378. Mutations in these regions, especially deletions of 10 to 20 amino acid residues, may result in a transactivationally defunct PREB protein which may be fused to another protein as described above.

The human PREB-encoding nucleic acids of the present invention were deposited with the American Type Culture Collection (ATCC), 10801 University Blvd., Manassas, Va. 20110–2209, on Feb. 1, 2000 and given accession numbers PTA-1258, PTA-1259 and PTA-1260. The human cDNA, as contained in plasmid pCRScript (Stratagene), was assigned accession number PTA1259. The present invention also provides for two genomic fragments, which encompass the PREB gene minus 500 bp from the 3'UTR that is within the cDNA transcript, of 1.6 kb and 2.5 kb respectively, which were assigned accession numbers PTA1258 and PTO1260 respectively.

In other specific, nonlimiting embodiments of the invention, an expression vector may incorporate a PREB gene (or a corresponding cDNA or RNA) as part of a polycistronic expression cassette together with a second gene whereby the second gene is operably linked to the 1P element of the PRL promoter and hence transactivated by PREB. For example, the second gene may encode for a protein capable of promoting cell growth, or capable of inhibiting the progression of cancer.

In further nonlimiting embodiments of the invention, the PREB gene may be co-expressed with another gene whereby the second gene is operably liked to the 1P element of the PRL promoter and hence transactivated by PREB and whereby the PREB gene and the second gene are not part of the same expression vector.

In yet further, nonlimiting embodiments of the invention, an expression vector may comprise a PREB gene (or corresponding cDNA or RNA) operably linked to a heterologous promoter (i.e. a promoter other than the naturally occurring PREB promoter), wherein such heterologous promoter may be an inducible promoter (e.g. the metallothionine promoter).

The PREB protein encoded by the PREB gene of the present invention has significant sequence similarity with the yeast TUP1 transcriptional repressor protein (Accession No:p16649) and Pfam database screening has identified PREB as a WD-repeat family member.

Sequencing of the cDNA of PREB revealed that it encodes a protein with significant homology to several previously identified ESTs (AA538253 mouse clone from pooled mouse organs =98% identity over 627 bp of 1919 bp, AI012746 rat placenta clone =97% identity over 450 bp of 1919 bp, AA688602 mouse myotube clone =96% identity over 476 bp of 1919 bp, AA647012 mouse mammary gland clone =94% identity over 385 bp of 1919 bp, AA892136 rat kidney clone =98% identity over 400 bp of 1919 bp, AA250620 mouse NML clone =96% identity over 412 bp of 1919 bp, AA646576 mouse mammary gland clone =96% over 399 bp of 1919 bp, AA967116 mouse mammary gland =94% identity over 484 bp of 1919 bp, AA925797 rat kidney clone =100% identity over 324 bp of 1919 bp, W30204 mouse clone =95% identity over 424 bp of 1919 bp, AA792848 mouse myotube clone =96% identity over 325 bp of 1919 bp, AA066564 mouse diaphragm clone =100% identity over 293 bp of 1919 bp, AA111707 mouse clone =90% identity over 497 bp of 1919 bp, H34594 rat clone =95% identity over 276 bp of 1919 bp, AA351639 infant brain *Homo sapiens* clone =88% identity over 386 bp of 1919 bp, AA300144 uterus tumor in *Homo sapiens* clone =90% identity over 285 bp of 1919 bp, W04666 fetal lung *Homo sapiens* clone =90% identity over 393 bp of 1919 bp, AA324676 cerebellum II *Homo sapiens* clone =87% identity over 328 bp of 1919 bp, AA687138 *Homo sapiens* clone =89% identity over 409 bp of 1919 bp, AA889019 parathyroid tumor *Homo sapiens* clone =89% identity over 407 bp of 1919 bp, H83961 *Homo sapiens* clone =89% identity over 400 bp of 1919 bp, N75291 *Homo sapiens* clone =89% identity over 400 bp of 1919 bp, AI089337 pregnant uterus *Homo sapiens* clone =89% identity over 381 bp of 1919 bp, AA629936 Stratagene lung carcinoma *Homo sapiens* clone =89% identity over 292 bp of 1919 bp, AA580861 *Homo sapiens* clone =89% identity over 281 bp of 1919 bp, Z17827 Stratagene cDNA human heart library =89% identity over 224 bp of 1919 bp, R39793 *Homo sapiens* clone =89% identity over 450 bp of 1919 bp).

The ESTs show that PREB DNA is present in a number of organisms and in a number of tissues. Additionally, PREB DNA sequences are significantly conserved (>85% homology overall). Although the ESTs span a significant portion of the PREB sequence as disclosed here, they have not been functionally defined and they do not represent a full length equivalent of PREB, with the largest EST spanning only 32.7% of the PREB sequence. In the absence of the full length clone and a functional characterization of the ESTs, these sequences have not disclosed the transcription factor which is responsible for the kinase-mediated transcriptional activation of prolactin and which has been elusive prior to the current invention.

The human PREB gene (Genbank Accession #AF203687) has been described (Dec. 21, 1999). The human PREB protein and PREB gene with Accession Number AF203687 differ from the present invention by the following:

13 additional nucleotides at the 5'UTR (TGG CAA CTC CCC G)

Nucleic acid 408 C to A;

Nucleic acid 943 C to G;

Nucleic acid 949 C to G.

Nucleic acid 2045, insertion of T.

The present invention still further provides for purified and isolated PREB proteins, or analogs thereof including the rat and the human protein, having an amino acid sequence as set forth in FIG. 1B (SEQ ID NO:2) and FIG. 11B (SEQ ID NO:13), respectively. In addition, the present invention provides proteins encoded by the nucleic acids provided herein, including nucleic acids which hybridize to a nucleic acid having SEQ ID NO:1, SEQ ID NO:12, and/or SEQ ID NO:16 under stringent conditions, and proteins which are at least 85%, and preferably 90% homologous to the complete rat or human PREB protein as determined by the Blast Search Algorithm and BESTFIT, through the program GCG (at HGMP, Cambridge, UK) using a Gap Weight of 8 and a Length Weight of 2. Correspondingly, human PREB, SEQ ID NO:12 encodes a 417 amino acid peptide and human PREB alternatively spliced variant, SEQ ID NO:16 encodes a 351 amino acid peptide.

In specific, non-limiting embodiments, the aforementioned peptides include the PREB gene's encoded protein including a start site at position 1 or a start site at position 217 as set forth in FIG. 1B (SEQ ID NO:1) for the Rat PREB gene and position 144 and 272 (SEQ ID NO:12) for the Human PREB gene, giving rise to a 345 amino acid and a 417 amino acid peptides respectively.

The present invention further provides for PREB protein and peptides having altered sequences which do not affect the DNA binding activity and/or the transactivation activity of the protein. Also included within the scope of the invention are PREB protein or derivatives thereof which are modified pre- or post-translation, for example by glycosylation, RNA splicing, proteolytic cleavage, adenylation, phosphorylation, acetylation, linkage to a ligand or an antibody, etc.

The present invention also provides for PREB protein and peptides having altered sequences that do not effect the DNA binding activity of the protein to the 1P promoter but do effect the transactivation activity, either by inhibiting or stimulating the transactivation activity. Also within the scope of the invention are alterations of the amino acid sequences which improve DNA binding affinity.

The present invention further provides for PREB protein and peptides having altered sequences which abolish its transactivation activity and such protein and peptides being fused to another protein (e.g. see above) which can act to block nearby promoter sequences from binding other trans-activating proteins. Such fusion proteins may block the binding of Pit-1 to the 1P element and nearby sequences thereby inhibiting Pit-1 transcriptional activation.

The present invention further provides for antibody molecules which specifically bind to a PREB protein, or portion thereof. According to the invention, a PREB protein, its fragments or other derivatives (e.g. histidine tagged protein), or analogs thereof, may be used as an immunogen to generate antibodies. Such antibodies include, but are not limited to, polyclonal, monoclonal, chimeric, single chain, Fab fragments, and a Fab expression library. In specific embodiments, antibodies which recognize rat PREB or a human homolog are produced. In nonlimiting specific embodiments, the antibodies which bind to PREB include, but are not limited to, a rabbit polyclonal antisera whereby a PREB peptide fragment (PREB amino acids 175–417, preceded by six histidines) is utilized as the immunogen to generate the antisera as described in the Examples section below.

Various procedures known in the art may be used for the production of polyclonal antibodies which specifically bind to a PREB protein. In a particular embodiment, rabbit polyclonal antibodies to an epitope of a PREB protein having an amino acid sequence set forth in FIG. 1B (SEQ ID NO:2) or FIG. 11B (SEQ ID NO:13) may be obtained. For the production of antibody, various host animals can be immunized by injection with the native PREB protein, or a synthetic version, or derivative (e.g., fragment) thereof, including but not limited to rabbits, mice, rats, goats, etc. Various adjuvants may be used to increase the immunological response, depending on the host species, and including but not limited to Freund's (complete or incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies directed toward a PREB protein, any technique which provides for the production of antibody molecules by continuous cell lines in culture may be used. Examples of such techniques include the hybridoma technique originally developed by Kohler and Milstein (1975, *Nature* 256:495–497), as well as the trioma technique, the human B-cell hybridoma technique (Kozbor et al., 1983, *Immunology Today* 4:72), and the EBV hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, *Proc. Natl. Acad. Sci.* U.S.A. 80:2026–2030) or by transforming human B cells with EBV virus in vitro (Cole et al., 1985, in *Monoclonal Antibodies and Cancer Therapy*, Alan R. Liss, pp. 77–96). Further, according to the invention, techniques developed for the production of "chimeric antibodies" (Morrison et al., 1984, *Proc. Natl. Acad. Sci.* U.S.A. 81:6851–6855; Neuberger et al., 1984, *Nature* 312:604–608; Takeda et al., 1985, *Nature* 314:452–454) by splicing the genes from a mouse antibody molecule specific for PREB together with genes from a human antibody molecule of appropriate biological activity may be used; such antibodies are within the scope of this invention.

According to the invention, techniques described for the production of single chain antibodies (U.S. Pat. No. 4,946,778) may be adapted to produce PREB-specific single chain antibodies. An additional embodiment of the invention utilizes the techniques described for the construction of Fab expression libraries (Huse et al., 1989, *Science* 246:12751281) to allow rapid and easy identification of monoclonal Fab fragments with the desired specificity for PREB protein derivatives, or analogs.

Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, the Fab fragments which can be generated by treating the antibody molecule with papain and a reducing agent.

In the production of antibodies, screening for the desired antibody can be accomplished by techniques known in the art, e.g. ELISA (enzyme-linked immunosorbent assay). For example, to select antibodies which recognize a specific domain of a PREB protein, one may assay generated hybridomas for a product which binds to a PREB fragment containing such domain. For selection of an antibody that specifically binds a first PREB homolog but which does not specifically bind a different PREB homolog, one can select on the basis of positive binding to the first PREB homolog and a lack of binding to the second PREB homolog.

5.2 DIAGNOSTIC METHODS

The present invention provides for a method of diagnosing the presence of an astrocytoma brain tumor in a subject as opposed to neuroepithelioma or glioma brain tumor, whereby the presence, amount, and/or molecular characteristics of the PREB gene, its corresponding mRNA or a cDNA thereof, or its gene product are determined. The presence of PREB RNA transcripts or protein would indicate the presence of astrocytoma brain tumor cells but not neuroepithelioma or glioma brain tumor cells and would possibly determine a course of treatment for the subject. Also included within the scope of the invention is the diagnosis of astrocytoma metastasis to the spinal fluid of the subject by the presence of PREB RNA transcripts or protein. As the metastatic potential of a malignant tumor may correlate with its presence in spinal fluid, a determination of the level of PREB mRNA or protein expression in a spinal fluid sample may have prognostic value, where high levels may bear a positive correlation with increased metastatic potential. The present invention also provides for a method of diagnosing trisomy 2p whereby the presence, amount, and/or characteristics of the PREB gene, its corresponding mRNA or a cDNA thereof, or its gene product are determined. Additional copies of the region of chromosome 2p encoding for PREB would indicate the trisomy 2p condition. The trisomy 2p condition is characterized by a syndromic phenotype that includes facial dysmorhism, mental and growth retardation, skeletal defects of the trunk and limbs and abnormalities of the genitalia. See Lurie et al., *Am. J. Med. Genet.* 55:229–236 (1995); Winsor et al., *Prenatal Diagnosis* 17:665–669 (1997).

In addition to being linked with trisomy 2p, the 2p23 chromosome region has also been significantly linked with hereditary low-bone mineral density, an identifying trait of osteoporosis. See Devoto et al., *Eur. J. Hum. Genet.* 6:151 (1998); Niu et al., *Hum. Genet.* 104:226 (1999). Subjects with familial osteoporosis contain homozygous deletions incorporating all, or nearly all of the PREB gene (see Example 14 and FIG. 17). Subjects with familial osteoporosis or subjects having general propensity for developing osteoporosis may also contain homozygous or heterozygous deletions incorporating part or all of the PREB gene. The administration of the PREB gene and/or its products to a subject with familial osteoporosis or a subject having a propensity for developing osteoporosis can correct or prevent bone mass loss in said subject.

Accordingly, the present invention provides a method for detecting a propensity to develop osteoporosis in a subject comprising detecting a deletion of all or part of the PREB gene. A deletion may be detected using portions of the PREB gene sequence as primers and using the Polymerase Chain Reaction to determine whether the full length PREB gene is present. A shorter product than expected would indicate a deletion, and no product could indicate a total deletion. Alternatively, primers could be made which flank the PREB gene, so that a total deletion in the PREB gene may still produce a signal. A deletion may also be detected by using the PREB gene as a probe for hybridization. If the PREB gene is deleted in full or nearly in full, no signal will be produced. If the PREB gene is partially deleted, a band of a smaller size than expected for the fill length would be detected. In addition, subjects having a propensity to develop osteoporosis may also have nucleotide variations, substitutions, disruptions of the PREB open reading frame, removal of regulatory regions of the PREB gene by chromosomal rearrangements or intro/exon shuffling/splicing defects.

In addition, the present invention provides a method for correcting or preventing bone mass loss in a subject comprising administering to said subject the PREB gene or its products. The PREB gene can be administered to a subject via a viral or non-viral vector comprising a nucleic acid encoding PREB by techniques known in the art. For example, the PREB gene may be contained in a plasmid, an adenoviral vector, an AAV vector, a retroviral vector or in a liposome. Alternatively, the PREB protein may be administered directly to a subject by techniques known in the art. Administration of PREB for the control or prevention of bone mass loss is useful where the loss of bone mass is correlated with a change in the PREB gene and gene products.

In specific, nonlimiting examples, the presence of PREB RNA transcript or protein in a subject may be evaluated by analyzing the RNA of the subject. In a specific, nonlimiting example, a sample of RNA obtained from the subject may be prepared, denatured, annealed with oligo(dT), and subjected to first strand synthesis in the presence of reverse transcriptase to generate cDNA from the subject's RNA sample. Using specific primers for the PREB gene, (e.g. but not limited to, a primer corresponding to positions 1081–1097, SEQ ID NO:4 or 1776–1761, SEQ ID NO:5 and a primer corresponding to positions 1300–1318, SEQ ID NO:6 or 1654–1636, SEQ ID NO:7, as shown in FIG. 1B, SEQ ID NO:1, or a primer corresponding to SEQ ID NO:14 and SEQ ID NO:15, or any primers designed from the PREB gene, including the Human PREB gene), nested PCR may be employed to detect the presence of PREB mRNA. In addition, methods such as, but not limited to, SSCP, entire gene sequencing or any methods known in the art which can detect nucleotide variations in either genomic DNA or cDNA from a subject.

Similarly, in a nonlimiting embodiment of the invention, the expression of PREB RNA in a subject may be evaluated in a cell or tissue sample, for example, by using Northern blot analysis, wherein RNA prepared from the sample is electrophoretically separated in the presence of formamide, transferred to a membrane (e.g. nitrocellulose), baked, prehybridized, and then hybridized to a $^{32}$[P]-labeled PREB probe for 15 hours, and autoradiographed to detect the presence of PREB RNA. In humans, three transcript sizes of the PREB mRNA are found corresponding to 2.2, 1.9, and 1.5 kilobases (as determined by a commercial Northern blot (Clonetech)). Alternatively, in situ hybridization techniques, RT-PCR, microarray technology and other methods known in the art which can identify and quantify PREB transcripts may be used to identify PREB RNA transcripts in cells and tissue sections.

Further, the expression of PREB protein in a subject may be evaluated. The PREB protein in a cell or tissue sample of a subject may be determined, for example, by Western blot analysis, wherein protein prepared from the sample is electrophoretically separated (e.g., in a polyacrylamide gel), transferred to a membrane (e.g., nitrocellulose) and then bound to anti-PREB antibody, which is either itself detectably labeled, or which is detected by a labeled secondary antibody.

The human PREB nucleic acid sequences of the present invention may also be useful in diagnostic methods to detect trisomy 2p. The presence of additional copies of PREB can be detected by Southern blot analysis or flourescent in situ hybridization (FISH) using nucleic acids corresponding to SEQ ID NO:1, SEQ ID NO:12, or SEQ ID NO:16, and fragments thereof, including SED ID NO:13 or SEQ ID NO:15.

5.3 MODEL SYSTEMS

The present invention provides for non-human animal model systems and in vitro cell systems which may be used to evaluate the effects of increasing, decreasing, or altering the temporal expression pattern of PREB expression and may be used to evaluate the effects of modified PREB nucleic acid sequences which encode for mutant PREB protein and/or fusion proteins containing PREB. Such animals, or cells grown in culture, may carry, as a transgene, an exogenously introduced PREB gene or a PREB cDNA, in some or all of their cells.

In specific, nonlimiting embodiments of the invention, a PREB encoding nucleic acid molecule, as described above, may be exogenously introduced into a non-human animal or a cell line. The PREB-encoding nucleic acid molecule may be operatively linked to a promoter, which may be a PREB promoter, a promoter selectively active in target cells, or an inducible promoter (such as the metallothionine or tetracycline promoter) or a promoter which directs widespread or ubiquitous expression (such as a human cytomegalovirus promoter or a retroviral LTR promoter).

Transgenic animals carrying an exogenous PREB-encoding nucleic acid molecule may be produced by standard techniques, including, but not limited to, techniques described in U.S. Pat. No. 4,736,866, PCT publication WO82/04443 and PCT publication WO88/00239. Such animals may also be produced by infection with vectors carrying a PREB encoding nucleic acid molecule in expressible form, or by inoculation with naked PREB-encoding DNA. Animals in which the endogenous PREB gene or its control elements have been altered by homologous recombination may be produced using techniques as set forth in U.S. Pat. No. 5,464,764 or Bradley, 1991, *Current Op. Biotechnol.* 2:823–829. The present invention also contemplates animals in which one or more endogenous gene has been "knocked out" and an exogenous PREB gene or cDNA has been introduced.

Cell lines carrying an exogenous PREB-encoding nucleic acid molecule may be produced by standard techniques, including, but not limited to, techniques described in *Cur-* rent Protocols in Molecular Biology, 1998, John Wiley and Sons, Publishers. Such cell lines may also be produced by infection with vectors carrying a PREB encoding nucleic acid molecule in expressible form, or by transfection with a naked PREB-encoding nucleic acid. Cell lines in which the endogenous PREB gene or its control elements have been altered by homologous recombination may be produced using techniques as set forth in Current Protocols in Molecular Biology, 1998, John Wiley and Sons, Publishers. The present invention also contemplates cell lines in which one or more endogenous gene has been "knocked out" and an exogenous PREB gene or cDNA has been introduced.

Non-limiting examples of animals which may serve as non-human animal model systems include mice, rats, rabbits, chickens, sheep, goats, cows, pigs, and non-human primates.

Non-limiting examples of cell lines which may serve as model systems include cell lines which do not express PREB (e.g. C6 rat glial cells or the human equivalent glial cell line e.g. DBTRG-O5MG).

For example, non-human animals, or human and non-human cell lines, may be produced in which extra copies of the PREB gene or cDNA have been introduced, or a PREB gene under a strong promoter has been created or introduced into the animal, or cell lines, such that the level of PREB protein, or mutant PREB protein, in the animal, or in a subset of cells of the animal, or in cell lines, has been increased relative to normal levels. Preferably the increase is by at least 25 percent. Such animals, or cell lines, may be used to study the effects of increased PREB levels, or to study the effect of the introduction of a mutant PREB protein, or a PREB protein made as a fusion with another protein so as to inhibit Pit-1 transcriptional activity and prolactin expression as described above. Such model systems are useful in studying the effects of PREB on the development of non-human animals and for studying osteoporosis.

Alternatively, non-human animals, or human and non-human cell lines may be produced which have lower than normal levels of PREB expression in some or all cells, by virtue of a defect introduced in one or more alleles of the endogenous PREB gene and/or its control elements. For example, but not by way of limitation, one or both alleles of the endogenous PREB gene in the animal, or cell line, may be eliminated or mutated by gene targeting techniques. Alternatively, an additional PREB gene with altered structure may be introduced which competes with endogenous PREB and thereby inhibits native PREB activity. The effects of PREB on bone mass may be studied in such model systems.

In other nonlimiting examples, non-human animals which have been engineered to have autoimmune disease (e.g. arthritis, diabetes, lupus), osteoporosis, a reproductive disorder, or AIDS related syndromes, such as, but not limited to, those animal model systems described in U.S. Pat. Nos. 5,777,193, 5,718,883, 5,489,742, 5,530,179, 5,675,060; 5,663,482 and 5,489,742, may be produced to over-express PREB either by the introduction of extra copies of the PREB gene or cDNA or engineered by the introduction of a PREB gene under a strong promoter. Such animals may be used to study the effect of increased prolactin levels on non-human animals with autoimmune disease, osteoporosis, a reproductive disorder or AIDS.

In other specific nonlimiting examples a PREB-encoding nucleic acid molecule of the invention, which has been mutated such that it can bind to the 1P element of the Pit-1 promoter, but cannot transactivate, may be introduced into a transgenic non-human animal which has a propensity for developing cancer (e.g. animal model systems described in U.S. Pat. Nos. 5,777,193, 5,811,634, 5,709,844, 5,698,764, and 5,550,316). Because the mutated PREB would be expected to compete with endogenous PREB for 1P binding, such an animal may be used as a model system to study the effect on the development of cancer after a reduction in the expression of the prolactin gene.

In further nonlimiting examples, transgenic non-human animals may be produced in which a mutated PREB gene which cannot transactivate but can bind the 1P element of the PRL promoter and/or which contains other nucleic acid sequences forming a fusion protein which cannot transactivate but can bind the 1P element of the PRL promoter and block Pit-1 binding, and such mutant PREB genes may be over-expressed by the introduction of multiple copies of the gene or by the use of a strong promoter, as discussed above. Such animals may be used as a model system to study the effects of the levels of serum prolactin on the development and control of graft-versus-host disease where transplantations (e.g. skin grafts, kidney, heart, liver, brain tissue, etc) are performed on the animal. Within the scope of the invention, is the same study where there are increased levels of PREB, creating a model system for studying the propensity for graft-versus-host disease in subjects with increased serum prolactin.

5.4 PREB AND OSTEOPOROSIS PROPENSITY

Osteoporosis is a skeletal disease characterized by low bone mineral density and microarchitectural deterioration of the bone structure, which leads to impaired skeletal strength and increased susceptibility to fracture (Consensus Development Conference, 1993). Bone mineral density (BMD), determined by dual energy x-ray absorptiometery (DEXA), is currently used to determine the risk of fracture.

Women over 50 years of age are at the greatest risk for developing osteoporosis (Melton et al., J. Bone Miner. Res. 7:1005 (1992)), which is thought to arise from the loss of estrogen post menopause (Riggs et al., J. Bone Miner. Res. 13:763 (1998)). Other well known risk factors include diet, premature or surgical menopause, late onset or irregular menstruation, extended lactation and endocrinopathies, such as hyperprolactinemia and gondal dysgenesis. Previous studies have shown that individuals with a family history of bone fracture are twice as likely to suffer fractures than the general population, and it has been suggested that genetic factors account for 70–80% of all variance in bone phenotype. For these reasons, much recent research has focused on the identification of genes and allelic variants predisposing, or conferring susceptibility to osteoporosis, with the majority of studies analyzing BMD measurements as the determining factor. Although, for example, allelic variations in the vitamin D receptor, the estrogen receptor, TGF beta receptor, interleukin 4 and 6, apolipoprotein E, collagen types 1a1 and 1a2, and the PTH receptors, have all been reported in association with reduced BMD, much further work is necessary to elucidate the genetic complexity of osteoporosis (reviewed in Eisman J. A. 1999).

While genome-wide scans for loci with linkage to BMD have recently been performed (Niu et al., Hum. Genet. 104:226 (1999)). Linkage analysis on seven families previously reported with a recurrence of low spine and hip BMD has been previously performed. Loci on chromosome 11q, 1p36, and chromosome 4qter were identified. The region 2p23-24 was also found to have significant linkage with both low hip and spine BMD. A more recent study using families of Asian origin showed evidence of linkage with distal forearm BMD to chromosome 13q34, and both proximal and distal forearm BMD to two individual loci on chromosome 2 (2p21.1-p21.3 and 2p23-p24) (Niu et al., *Hum. Genet.* 104:226 (1999)).

The human PREB gene has been mapped to a region on chromosome 2p23 previously linked to low bone mineral density (BMD) (FIG. 17 and Example 14). Low BMD is the most common risk factor for developing osteoporosis, a disease that has been associated with abnormal hormone levels, as well as defects in bone growth and remodeling processes. Chromosome 2p23 has also been associated with a trisomy syndrome manifesting various skeletal abnormalities. Therefore, disruption of the PREB gene will result in low BMD, leading to osteoporosis.

This invention has shown the existence of allelic variations of the PREB gene in one nuclear family within a large pedigree exhibiting BMD linkage to the PREB locus. Two children within this family, both of whom manifest low spine and hip BMD, were homozygously deleted for exons 2–9 of the PREB gene (containing nine exons in total) (see Example 14 and FIG. 17).

The role for PREB in osteoporosis can be determined by an investigation of the biochemical function of this protein, involving an analysis of the molecular pathways in cellular development and differentiation that PREB protein may interact with and/or regulate. The yeast-two hybrid system to can identify proteins, particularly expressed at murine embryonic day 14.5 in murine embryonic stem (ES) cells, that interact with PREB.

Stable murine ES cell lines containing targeted mutations of the Preb gene can be generated. These lines can be differentiated in vitro into mature cell lineages. DNA microarray technology can also be employed to investigate gene expression in cells of skeletal lineages expressing abnormal levels of the Preb gene transcript. A mouse model can then be generated with a targeted disruption of the Preb gene since murine models have been shown to be very powerful in elucidating the role of genes in both development and the mature organism.

The rat PREB protein of the present invention is a novel transcription factor, that exhibits binding to the prolactin promoter, and can upregulate prolactin and growth hormone gene expression in vitro (Fliss et al., *Mol. Endocrinol.* 13:644 (1999)).

Analysis of the expression of the human PREB gene of the present invention has shown that PREB is ubiquitously expressed in both adult (Fliss et al., 1999), and fetal tissue (Clelland et al., Genomics, In Press, incorporated herein by reference). However, the expression level differs among tissues, with the highest levels detected in adult salivary gland, liver, pancreas and skeletal muscle, and fetal liver (Clelland et al., Genomics, In Press, incorporated herein by reference). Analysis of Preb gene expression during murine embryogenesis detected transcripts in the perichondrial region of all major subdivisions of the fetal skeleton. In early staged embryos this corresponds to mesenchyme cells located in the future cervical region and thus the first branchial arch and immediately adjacent caudal tissue; while at later stages expression is detected in Meckel's cartilage, the basicranium, the developing rib shafts and the long bones of the forelimbs and hindlimbs. The most extensive expression of Preb is observed in the perichondrium of the craniofacial, axial and appendicular skeleton. Preb transcripts are also observed in the inferior wall of the genital tubercle, and the precursor of the developing pituitary gland. The PREB gene is highly conserved in mammals and invertebrates. Analysis of Drosophila melanogaster Preb gene expression shows the presence of transcripts in the salivary gland of early embryos (Clelland and Lo, in preparation).

The murine Preb gene of the present invention has been mapped to proximal chromosome 5 (Clelland et al, Genomics, In Press), and to the syntenic region on human chromosome 2p23. This region has been commonly associated with a chromosome re-arrangement syndrome known as Trisomy 2p syndrome. Although variable, the common duplication phenotype includes facial abnormalities, skeletal defects, growth and mental retardation, congenital heart and neural tube defects, and abnormalities of the genitalia. The skeletal abnormalities commonly include dolichostenomelia (long tapering fingers and fan-like position of the toes), polydactyly, and long bone abnormalities. Deformities of the rib cage and vertebrae, and delayed bone age have also been reported. Abnormal dosage of the PREB gene may result in some of the abnormalities observed in this syndrome.

PREB gene expression is important during skeletal development. Murine Preb is co-expressed with genes in the perichondrium of the developing skeleton, known to finction in the feedback signaling pathways controlling chondrocyte differentiation and osteoblast formation. The abnormal dosage of PREB may result in skeletal abnormalities, and the mapping of human PREB to a region linked to low BMD, are all consistent with the hypothesis that PREB may function in both bone development and adult bone re-modeling. The role for PREB in the recurrence of low BMD in families with linkage to chromosome 2p23-24, can be analyzed as well as the biochemical role of PREB in cells of skeletal lineages.

The PREB gene has been mapped to chromosome 2p23-24 and an EST clone of the PREB gene has been made that has been positioned on the radiation hybrid map (WICGR) at position 158.27cR from the top of the chromosome 2 linkage group. This locus falls within the YAC contig WC2.2 (Whitehead Institute) to which the marker D2S170 has also been mapped. Consistent with this mapping data, the PREB EST has also been mapped to the NCBI GeneMap, between the markers D2S165–D2S352 (~5 cM distance), which overlaps distally with the area of linkage within the low BMD pedigree.

An allelic variation of the PREB gene segregates in members of the family with low BMD. This was shown with primers designed to amplify the entire PREB gene in each individual, including all intron/exon boundaries, for direct sequence analysis. PCR experiments of one nuclear family, in which the mother and two children had low hip and spine BMD yielded no amplification of the PREB gene downstream of exon 1 in either of the two children, although flanking sequences on chromosome 2p23 did amplify, along with experimental control genes that map to chromosome 12 and 4. This result strongly suggests the presence in these two individuals, of a homozygous deletion of the PREB gene downstream of exon 1.

Exon 1 of the PREB gene PCR amplifies when using a primer pair designed from sequence within this exon. Amplification is totally lost when the primers map within intron 1, suggesting that, at least for one chromosome, a breakpoint of this deletion maps within intron 1. This data is consistent with the a small, microscopic, interstitial deletion. Analysis of the microscopic deletion can be carried out by Southern blot hybridization to determine dosage of the PREB gene, using DNA isolated from each individual in the nuclear family and all other members of the large pedigree. The Southern analysis can be used to search for abnormal restriction enzyme patterns within the genomic region including and flanking PREB. Restriction patterns can be compared to genomic sequence of the region. Using the results of sequence data obtained above, primers can be designed for PCR amplification to amplify across the deletion boundaries on both chromosomes in each individual. Cloning and sequence analysis of all deletions can thus be achieved.

G-banding and FISH analysis (using the two genomic PACs that incorporate the PREB gene), on metaphase chromosomes (derived from lympoblastoid cell lines of blood) from each individual in the nuclear family can also be performed to determine whether large structural rearrangements occur in the PREB gene. This information can be used to design PCR primers that flank large deletions to identify deletion boundaries. Cloning and sequencing of large deletions can be performed by PCR, using the Expand long PCR system (Boehringer Mannheim) for large product amplification.

Northern analysis of human PREB transcript size, using the full length rat cDNA as a hybridization probe, has identified three possible alternatively spliced PREB transcripts of sizes 2.2kb, 1.9kb, and 1.5kb in the six human adult tissues examined (Fliss et al., 1999). Although the pattern of transcripts is tissue specific, the 2.2kb PREB transcript was expressed in all tissues examined. The 1.9kb transcript from a human cDNA library derived from a embryonic lung fibroblast cell line, M42 has been obtained. This transcript (SEQ ID NO:16; FIG. 15A) arises from alternative splicing of the PREB gene primary transcript, yielding an mRNA in which exon seven is deleted, and a frameshift occurs (see FIG. 16 and SEQ ID NO:18 for a complete genomic sequence representation of the human PREB gene). The resultant encoded protein loses 84 amino acids from the C-terminus of PREB, and has an additional 17 novel residues at this terminus, followed by a stop codon (SEQ ID NO:17. FIG. 15B).

In situ hybridization has demonstrated that murine Preb is expressed in the perichondrium of the developing bone (Taylor Clelland et al., 2000), and it is mesenchyme cells within this distinct element that differentiate into osteoblasts. The PREB protein isoforms involved in bone development and remodeling can be determined by analyzing which murine and human transcripts are expressed in particular skeletal lineages.

The yeast-two hybrid system involves an experimental procedure that, with new advances in vector technology, yeast strains, and the addition of interaction reporter genes, has become a reliable technique to look for interactions between proteins. Using the MatchMaker system, version 3 (Clontech, Palo Alto, Calif.), to minimize the number of false positives, both the 417 amino acid, and 350 amino acid PREB isoforms described above have been cloned into a GAL4/binding domain vector, and expressed in the yeast strain AH109. This transformed strain can be used in a co-transformation with a murine embryonic day 14.5/GAL4 activation fused cDNA library. Interacting clones can be sequenced, and the interaction with PREB confirmed by experiments involving GST pull-down assays, and or immunoprecipitation assays using a PREB antibody. The identification of PREB-interaction proteins, expressed during murine development can provide information regarding both upstream and downstream molecular pathways in which PREB plays a role. An example of the use of this system to characterize a WD-motif protein and provide evidence that the protein has a major role in a human development syndrome has been previously reported (Magnaghi et al., 1997).

Mouse embryonic stem cells (ES), derived from the inner cell mass of the early blastocyst, are used for the generation of genetically altered mice. Furthermore, studies have been performed which utilize the ability of totipotent ES cells to differentiate into lineages derived from each of the primary germ layers, following induction with specific growth stimuli (Keller, 1995). This ES cell property has resulted in their use as an in vitro model to characterize developmental gene expression at the cellular and molecular level. Stable ES cell lines that are either homozygously or heterozygously deleted for Preb, or trisomic for the Preb gene can be generated using these techniques. These lines can be generated using the loxP/cre recombinase gene targeting system. A murine 129/SvevTACfBr whole genomic PAC library (HGMP) has been screened and eleven PACs that hybridize to the murine Preb have been isolated. The intron/exon boundaries of Preb can be determined from these PACs and the sequence data can be used to design a construct for homologous recombination with an ES cell strain compatible with the PAC genomic sequence (as described in Lindsay et al., 1999).

The ES cell lines can be induced to differentiate into mature osteoblasts, employing BMP-2 as the growth stimulant (Katagiri et al., 2000), through an intermediate differentiation into myoblast cells using conditions described previously (Rohwedel et al., 1994). At each stage of differentiation, cell types can be characterized by RT-PCR analysis of known tissue specific transcripts. Microarray technology can then be employed to examine simultaneously the expression levels of thousands of murine genes in response to an abnormal dosage of the PREB gene. Following probe hybridization, expression levels of transcripts can be analyzed. This approach can determine molecular pathways involving Preb gene expression.

The overall physiological role(s) of PREB can be determined using the stable ES cell lines described above to generate a mouse with a targeted disruption of Preb which can be used as a model system to study osteoporosis and BMD.

5.5 REGULATION OF PROLACTIN EXPRESSION AND TREATMENT OF DISEASE

The present invention provides for methods of treating cancer, autoimmune disease, developmental defects, reproductive disorders and osteoporosis through the regulation of prolactin expression via the alteration of PREB gene products, mutants, fusions and derivatives thereof or through the regulation of PREB itself.

In certain embodiments of the invention, the cancer, autoimmune disease, developmental defects, reproductive disorders or osteoporosis is associated with elevated levels of prolactin expression, in which case it is desirable to decrease PREB transactivation activity and/or Pit-1 transactivation activity accordingly to reduce prolactin expression in a subject or in a particular tissue or cell population of the subject. Such a decrease in PREB expression may be achieved by either inhibiting the expression of the endogenous PREB gene, for example, by the administration of an antisense RNA or ribozyme or an inhibitor of the PREB promoter, or inhibiting the action of PREB protein, for example, by over-expressing a transactivation negative-DNA-binding-positive mutant of a PREB fusion protein which may also be capable of inhibiting Pit-1 transactivation activity (as described above) or by administering an anti-PREB antibody (or a fragment or derivative thereof) which is capable of inhibiting the PREB transactivation activity and/or its DNA binding activity. Conditions which may benefit from such treatment include, but are not limited to, breast cancer, ovarian cancer, prostate cancer, pituitary tumors (where the inhibition of the expression of PRL may inhibit or reduce tumor growth), rheumatoid arthritis, systemic lupus erythematosus, autoimmune type I diabetes, adjuvant-induced arthritis, collagen type II-induced arthritis (where reduced serum levels of prolactin may favorably influence the prognosis of the disease), and graft-versus-host disease (where reduced serum levels of PRL may eliminate the host reaction to the transplanted graft). As PREB may also be a ubiquitous transcription factor, defects in PREB alone may result in adverse conditions. In such a case, it is desirable to control the levels of PREB to effectuate a down-regulation or up-regulation of transcription generally.

Similarly, cellular proliferation may be inhibited by a decrease in PREB expression which may be achieved by either inhibiting the expression of endogenous PREB genes as described above (i.e. by the administration of PREB antisense RNA, over-expression of a PREB inhibitor protein, or over-expression of a transactivation-negative-DNA-binding-positive PREB mutant).

In other embodiments of the invention, the cancer, autoimmune disease, developmental defect, reproductive disorder or osteoporosis is associated with decreased levels of prolactin expression, in which case it is desirable to increase PREB transactivation activity accordingly in a subject or in a particular tissue or cell population of the subject. Such an increase may be achieved by the over-expression of PREB protein in a manner that stimulates prolactin expression either through the introduction of multiple copies of the PREB gene or cDNA, and/or through the introduction of a PREB gene or cDNA operatively linked to a strong promoter. Conditions which may benefit from such treatment include, but are not limited to, AIDS, immunosuppression, and some cancers. Additionally, where over-expression of TGF-beta is implicated in disease development, over-expression of PRL may overcome the undesirable effects of TGF-beta.

In particular embodiments, the present invention provides for a method of increasing PRL expression in a tissue of a subject in need of such treatment, comprising increasing the amount of PREB transactivation activity in the tissue using methods as set forth above. Nonlimiting examples of such tissues include tissues of the immune system, bone marrow, and skin.

In alternative embodiments, the present invention provides for a method of decreasing the expression of prolactin in a tissue of a subject in need of such treatment, comprising decreasing the amount of PREB activity in the tissue using methods as set forth above. In a specific nonlimiting embodiment, the tissue is a breast carcinoma, prolactinoma, or prostate carcinoma.

Administration of the foregoing agents may be local or systemic, using a suitable pharmaceutical carrier. Other compounds which aid in the uptake or stability of these agents, or which have beneficial pharmaceutical activity, may also be included in the formulations of the invention.

5.6 EXPRESSION OF FOREIGN GENES

The present invention provides for methods for the expression of exogenous genes, in vivo or in vitro, comprising the administration of a polycistronic vector which may incorporate a PREB gene (or a corresponding cDNA or RNA) as part of a polycistronic expression cassette together with a second gene, or multiple genes (or corresponding cDNA or RNA) whereby the second gene (or multiple genes), is operably linked to the 1P element of the PRL promoter and hence transactivated by PREB. The PREB gene (or a corresponding cDNA or RNA) may be operatively linked to a constitutive promoter or an inducible promoter (e.g. the constitutive major intermediate early promoter of cytomegalovirus or the metallothionine promoter). Also within the scope of the invention, are multiple vectors whereby the PREB gene (or corresponding cDNA or RNA) is incorporated into a vector and whereby another vector contains other heterologous genes operably linked to the 1P element of the PRL promoter.

In certain embodiments of the invention, in the vector described above, the second gene may encode for a growth factor, or multiple growth factors (e.g. of growth factors; Epidermal Growth Factor (EGF), Fibroblast Growth Factor (FGF), Platelet Derived Growth Factor (PDGF), Nerve Growth Factor (NGF)) and may be introduced into skin cells, brain cells, immune cells (B-cell hybridomas), or bone marrow cells grown in vitro in order to stimulate the growth of such cells which could ultimately be transplanted to a subject but is not limited to the enumerated cells. Such cells could be used therapeutically to treat burns or other wounds, Alzheimer's disease, Parkinson's disease, AIDS, or leukemia. Additionally, such cells may be autologous to the intended host.

In other, nonlimiting embodiments of the invention, the vector described above may be administered to a subject in vivo to result in its introduction into skin cells, bone marrow cells, brain cells, immune cells. Such a vector may stimulate the growth of the subject's cells.

In further, nonlimiting embodiments of the invention, the vector described above may stimulate the growth of primary cell lines in vitro which otherwise would divide a finite number of times in culture. Such cell lines may be useful for long term studies of primary cell lines.

In alternative, nonlimiting embodiments of the invention, in the polycistronic vector described above, the second gene may encode for a heterologous protein or peptide. Such a vector may be stably transfected into an immortalized eukaryotic cell line which lacks endogenous PREB expression (e.g. a cell line with a "knock-out" mutation of the endogenous PREB gene) to result in the enhanced expression of the heterologous gene of interest for subsequent in vitro studies and/or for mass production. In such embodiments, the PREB gene may be optionally operably linked to an inducible promoter.

In related embodiments rather than a single vector comprising PREB and a second gene of interest, a first vector comprising PREB operably linked to a first promoter element, and a second vector comprising the second gene of interest operably linked to a second promoter which comprises a 1P element, may both be introduced into an immortalized eukaryotic cell line.

It is noted hereby that certain experimental results obtained by the inventors have not supported those described in the working Examples below regarding the role of PREB in PRL expression.

6. EXAMPLE

IDENTIFICATION OF THE PREB CODING SEQUENCE 6.1. MATERIALS AND METHODS

"Southwestern" screening. A filter-bound, denatured-renatured expression library was screened with a concatenated probe as described in Singh et al., 1988, *Cell* 52:415–423 and Vinson et al., 1988, *Genes Dev.* 2:801–806.

[$^{32}$P]-labeling of DNA. Prolactin promoter element 1P DNA was [$^{32}$P]-labeled as described in *Current Protocols in Molecular Biology*, John Wiley and Sons, publishers (1996).

Preparation of cDNA library. A bacteriophage cDNA library was prepared from the GC rat pituitary cell line as described in Bancroft, 1981, *Functionally Differentiated Cell Lines* 47–59 Alan R. Liss, New York, publishers.

6.2 RESULTS

To search for factors that might play a role in regulation of prolactin gene expression via the proximal Pit-1 DNA binding site 1P, this DNA element was employed as a probe to screen a bacteriophage cDNA library prepared from the GC rat pituitary cell line λZAPII cDNA library (Stratagene, La Jolla, Calif.). Screening of $1.5 \times 10^6$ plaques yielded several presumptive positive clones that bound to labeled site 1P. However, only one of these clones exhibited DNA-sequence specificity: binding to element 1P, but not to either a mutated element 1P or a canonical CRE. The properties of this clone, designated PREB, were further investigated. The pBLUESCRIPT vector containing PREB cDNA was excised in vivo, and the cloned cDNA was sequenced, yielding a 1.28 kilobase sequence containing a large (240 amino acid) open reading frame, but lacking a putative initiator methionine. Successive applications of 5'-RACE (rapid amplification of DNA ends) of GH3 cell RNA yielded an additional 636 bases, resulting in the PREB cDNA sequence shown in FIG. 1B (SEQ ID NO:1), containing in-frame methionine codons at positions 1 and 217. The ATG at position 217 is preceded by ACC, matching well the Kozak consensus (SEQ ID NO:8), while the ATG at base 1 is preceded by the poorly matching sequence GGG (SEQ ID NO:9). The sequence following each methionine encodes PREB containing, respectively, either 345 amino acids (~38kD) or 417 amino acids (~46kD). Putative polyadenylation and AU-rich mRNA shortened half-life elements in the cDNA 3'UT were also noted.

7. EXAMPLE

SEQUENCE SPECIFIC BINDING TO THE 1P ELEMENT

7.1. MATERIALS AND METHODS

Electrophoretic mobility shift assay. Partially purified recombinant his-tagged PREB (PREB amino acids 175–417, preceded by six histidines) was prepared from transformed *E. coli* by solubilization of an insoluble pellet in binding buffer (5 mm imidizole, 0.8 M NaCl, 10 mM Tris {pH 7.9}, 8 M urea), application to a nickel affinity column, gradual refolding on the column by progressive dilution of the urea (as described in Vinson et al., 1988, *Genes Dev.* 2:801–806), elution in buffer containing 0.5–1.0 M imidizole, followed by desalting and concentration in an Amicon (Beverly, Mass.) spin column. Double-stranded oligonucleotides corresponding to prolactin promoter sites 1P, *1P, 1P*, and 3P, (FIG. 3C) and the CLE have been previously described in Yan et al., 1991, *Mol. Endocrinol.* 5:535–54 and Yan et al., 1994, *Mol. Cell Endocrinol.* 101:R25–R30. The sequence of the double-stranded SP1 binding site oligonucleotide probe (containing a 5' Sal In site) is 5'-TCGACGGGGCGGGGCC-3' (SEQ ID NO:10), and of the double-stranded rat GH pGHF-1 site is 5'-TCGACTGGCTCCAGCCATGAATAAATGTATAGGG AAAG-3' (SEQ ID NO:11). All procedures were performed at 4° C. in the presence of protease inhibitors (1 mM PMSF, 1 µg/ml aprotinin, and 5 µg/ml leupeptin). The partially purified his-tagged PREB was then incubated 10 minutes at room temperature in 9 µl containing 10 mM Tris (pH 7.9), 60 mM KCL, 1 mM EDTA, 0.03% NP40, 4% Ficoll, 1 mM DTT, 5 µg poly(dI-dC), 1 µg BSA, with or without unlabeled DNA competitors, then an additional 10 minutes following addition of 1 ng $^{32}$P-end-labeled site 1P probe, followed by analysis on a 5% polyacrylamide gel in 0.25=TBE at 4° C. The dried gel was then autoradiographed 1–3 hours at −70° C. with intensifying screens.

Imaging of gels. Autoradiograms of gel blots or photographs of gels were recorded electronically using an AGFA (ARCUS II) Scanner (Leverkusen, Germany).

7.2. RESULTS

PREB exhibits DNA sequence-specific binding to prolactin promoter element 1P. Electrophoretic mobility shift was employed to examine the DNA sequence binding specificity of recombinant PREB (FIG. 3A). PREB plus the element 1P probe that was employed to clone PREB yielded a single shifted band (lane 2), which was competed by excess cold element 1P (lanes 3–5). Use of element 1P mutants (illustrated in FIG. 3B) showed that PREB binding to element 1P was also inhibited by an excess of the 1P* mutant (lanes 9–11), but not the *1P mutant (lanes 6–8). The inability of *1P to compete implied that the PREB site in element 1P is located at least partially on the 5' side of this element (FIG. 3C). Since X-ray analysis has recently shown that the Pit-1POU domain binds to element 1P as a dimer by contacting the bases bracketed in FIG. 3B as described in Jacobson et al., 1997, *Genes Dev.* 11:198–212, the ability of 1P* to compete PREB binding implied that Pit-1 and PREB possess different, but possibly overlapping, binding sites within element 1P. The observation (FIG. 3A) that PREB binding was not competed by excess amounts of oligonucleotides corresponding either to the Pit-1 binding site, PRL-3P (lanes 12–14) or GH-GHF1 (lanes 15–17), or to two unrelated DNA sequences, an SP1 binding site (lanes 18–20) or the PRL promoter CLE sequence as described in Coleman et al., 1996, *Endocrinology* 137:1276–1285 (lanes 21–23), further confirmed the DNA binding specificity of PREB. Since no known DNA-binding motif can be detected in the PREB amino acid sequence shown in FIG. 1B (SEQ ID NO:2), this specificity is likely to be conferred by a novel DNA-binding motif. These results are consistent with the use of the 1P element as the promoter sequence for any gene which can then be expressed by the co-expression of PREB.

8. EXAMPLE

PREB IS A SINGLE COPY GENE AND IS REVOLUTIONARILY CONSERVED

8.1. MATERIALS AND METHODS

Southern Blot Analysis. Restriction enzyme-digested DNA was transferred to nitrocellulose filters according to the Basic Protocol described in Ausubel et al. (*Short Protocols in Molecular Biology*, Third Edition, 1995, John Wiley and Sons, Publisher), Unit 2.9 A. Prehybridization and hybridization were then performed at 39° C. according to the Basic Protocol described in *Short Protocols in Molecular Biology*, Unit 2.10 (Appendix 1), employing a $^{32}$P random-primed rat PREB cDNA probe and the aqueous prehybridization/hybridization (APH) solution. Filters were washed as described in *Short Protocols in Molecular Biology*, Unit 2.10, including the two optional 15 minute moderate-stringency washes described (42° C.; 0.2×SSC/ 0.1% SDS).

8.2. RESULTS

Figure 4:
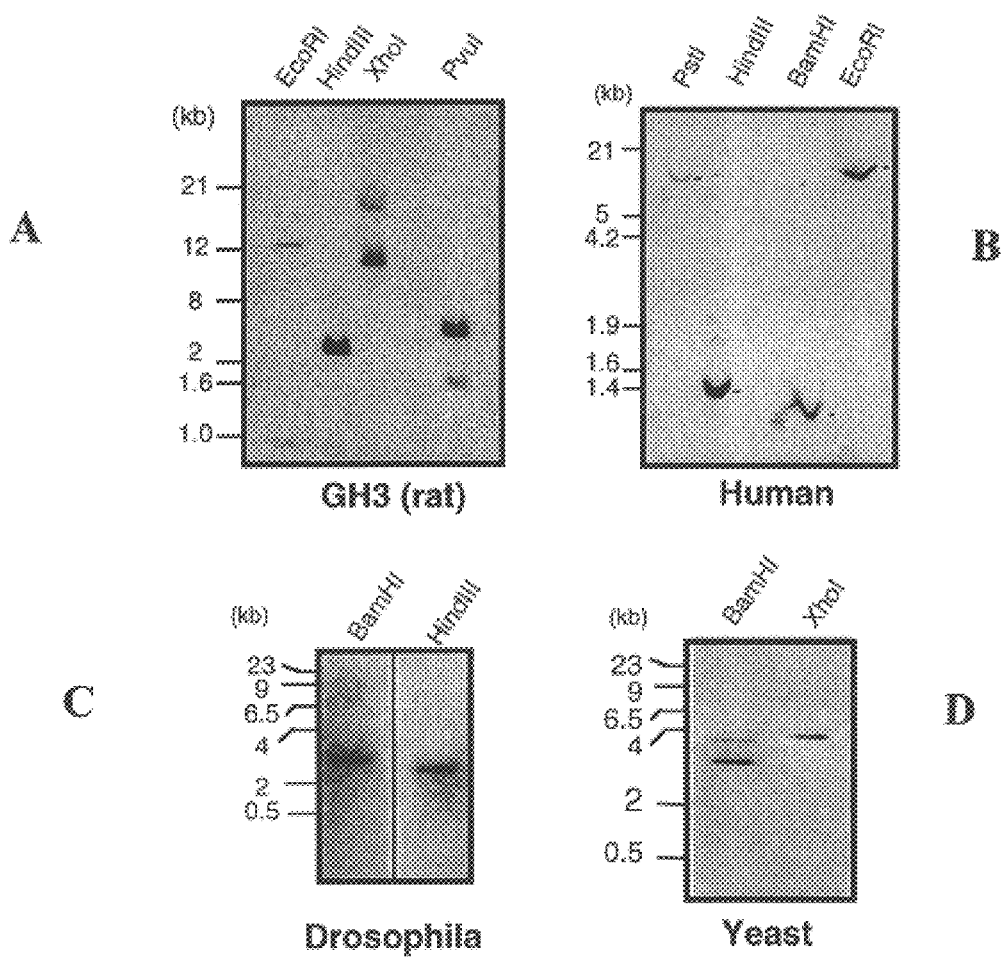

Southern blot analysis was employed to determine the structure and number of PREB genes in various organisms (FIGS. 4A–D). Digestion of rat DNA with the DNA restriction enzymes EcoRI and HindIII, XhoI and PvuI yielded, respectively single or double bands on an agarose gel. The double bands detected with the latter two enzymes probably correspond to cleavage with an intron, since the PREB cDNA sequence contains neither recognition site. Single bands were detected upon digestion of human DNA with any of four enzymes (FIG. 4B). Thus PREB is apparently a single copy gene that is well-conserved between rat and human (FIG. 4A and FIG. 4B respectively). Restriction enzyme digestion of either Drosophila or Yeast DNA also yielded one or two bands that hybridized with rat Preb cDNA, implying that the PREB gene (or a related gene) has been highly conserved during evolution (FIG. 4C and FIG. 4D). The ability of rat Preb to hybridize to the DNA of other organisms was the basis for the determination that the gene is well conserved among various species.

9. EXAMPLE

PREB CAN FUNCTION AS A TRANSCRIPTIONAL ACTIVATOR 9.1. MATERIALS AND METHODS

Preparation of anti-PREB antiserum. Inclusion bodies were prepared from *E. coli* expressing recombinant histagged PREB (PREB amino acids 175–417, preceded by six histidines), (as described by Sambrook et al., 1989, *Molecular Cloning: A Laboratory Manual*. Cold Spring Harbor Press, Cold Spring Harbor, publishers). Cells were lysed with lysozyme and deoxycholic acid in the presence of 50 mM PMSF, treated with DNAse (1 mg/ml) at room temperature for 15 to 30 minutes, and subjected to centrifugation. The pellet was then suspended, washed with 6.5 M urea in 0.1 mM Tris, pH 8.5, then PREB was extracted with elution buffer (8 M urea, 50 mM Tris, pH 8.0, 1 mM EDTA, 100 mM NaCl, 0.1 mM PMSF), and subjected to SDS-PAGE gel electrophoresis. A gel fragment containing the major PREB band was excised, frozen, ground with a mortar and pestle, and supplied frozen to Cocalico Biologicals, Inc. (Reamstown, Pa.) for preparation of antiserum in rabbits according to their standard protocol. Prior to use in Western Blot analysis and immunocytochemistry, either anti-PREB antiserum or preimmune serum from the same animal was preadsorbed with extracts of host *E. coli*. An equal volume of 2×SDS sample buffer was added to a pelleted 50 ml bacterial culture, mixed thoroughly, incubated at 65–70° C. for 10 minutes, fractionated on a 4.5% SDS-PAGE mini-gel employing a 1.5 mm preparative comb, and transferred to nitrocellulose. After soaking the filter in a 5% solution of Carnation brand non-fat milk, the filter was incubated on a rocking platform either one hour at room temperature or 4° C. overnight, with anti-PREB antiserum diluted 1:250 into TBST buffer (20 mM Tris, pH 7.6; 137 mM NaCl, 0.1% Tween-20) containing 3% bovine serum albumin, and the adsorbed antiserum employed for analysis of PREB.

Western blot analysis. Nuclei and cytosol (i.e. the soluble fraction of the post-nuclear supernatant) were prepared from GH3 cells as described by Lee et al. *Gene Anal. Tech.* 15:22–31 (1988), in the presence of the protease cocktail containing 1 mM PMSF, 1 µg/ml aprotinin, and 5 µg/ml leupeptin. Preliminary SDS-PAGE electrophoresis analysis revealed no gross degradation of proteins in either fraction, and that on a per cell basis, the cytosol contained a considerably higher protein content than the nucleus. Samples were subjected to SDS-PAGE, transferred to nitrocellulose on a semi-dry transfer apparatus (Hoeffer Scientific Instruments, San Francisco. Calif.), employing Towbin buffer (25 mM Tris, 192 mM glycine, 0.0372% SDS, 20% methanol) for 30 to 60 minutes at 100 mAmps. Filters were blocked for 1 hour with 5% Carnation non-fat dry milk in TBST, incubated with anti-PREB antibody (1:250), followed by washing with TBST. The filter was then exposed to secondary antibody (conjugated to horseradish peroxidase and diluted 1:5000) in TBST containing 3% bovine serum albumin for 30 to 60 minutes. Following washing with TBST (4 times 10 minutes), immunoreactive proteins were visualized by enhanced chemiluminescence according to the directions of the manufacturer (Amersham Corporation, Arlington Heights, Ill.).

Immunocytochemistry of Cultured Cells. Cells were plated on glass cover slips in serum containing media the night before use (C6 cells, DMEM plus 5% fetal calf serum; GH3 cells in Ham's F10 plus 15% horse serum plus 2.5% fetal calf serum). For use with GH3 cells, the cover slips were first coated with CellTak (14 µg/25 mm cover slip) (Collaborative Biomedical Products, Bedford, Mass.). The cells were washed twice with phosphate buffered saline (PBS), fixed 20 minutes at room temperature in 2% paraformaldehyde, incubated 20 minutes in blocking buffer (0.6% Tween 20 in DMEM containing 5% fetal calf serum) and then incubated overnight at 4° C. with either 1:250 dilutions of preimmune serum or anti-PREB, each preadsorbed as described above. The dishes were then washed three times with PBS, and incubated 30 minutes with rhodamine-labeled goat anti-rabbit IgG (American Qualex, LaMiranda, Calif.) at 1:500 in blocking buffer, rinsed three times, and mounted in Mowiol. Images were captured using a 40× oil objective on a Nikon inverted microscope with a Cohu CCD4910 camera in conjunction with a Colorado video integrator unit. Digital data were processed with Metamorph software from Universal Imaging, Media, PA.

Transient co-transfection assays. For each treatment group, approximately $0.5 \times 10^8$ or $2 \times 10^6$ C6 cells were subjected to electroporation. Preliminary experiments were performed with PRL–CAT constructs and a known prolactin promoter regulator, Pit-1, to optimize transfection efficiency for each cell line. For transfection, cells were resuspended in 0.75 ml DMEM containing 10% fetal bovine serum plus the indicated plasmids, and subjected to electroporation at 960 µF and either 300 volts (C6 cells) or 240 volts (GH3 cells), divided among three 60 mm tissue culture dishes, and incubated 48 hours as described above for each cell line. One day following transfection, each dish was examined microscopically, and any experiment that exhibited gross differences in cell survival among different treatment groups was discarded. Cells were then harvested with a rubber policeman, lysed by sonication (2 minutes×4) in 0.25 M Tris, pH 7.8, 10 mM EDTA, and heated to 65° C. for 10 minutes to inactivate deacetylases. Half of each cell extract was assayed for CAT activity as described previously (Fischberg et al. *Mol. Endocrinol.* 8:1566–1573. 1994), employing [$^3$H]chloramphenicol (0.01 µCi/µl) and butyryl CoA (5 mg/ml) and a 4 hour incubation, which yielded results in the linear range of the assay. The remainder of the cell extract was employed for assay of β-galactosidase activity as described (Ausubel et al., 1996 *Current Protocols in Molecular Biology*. John Wiley and Sons, publishers). For each experimental condition, the average CAT assay result was divided by the average β-galactosidase activity under that condition, relative to a value of 1 assigned to the average β-galactosidase activity in the controls. It may be noted that this procedure always yielded a correction of $\leq 2\%$. Each experiment reported here has been repeated a total of at least three times, with results similar to those shown in the figures.

Plasmids. The construction of plasmids (−1957) PRL–CAT and (−113) PRL–CAT was described previously. Jackson et al. Mol. Endocrinol. 2:1139–1144 1988 and Lufkin et al. Science 237:283–286 1987. RSV–PKA was prepared by employing PCR primers to amplify the murine PKA catalytic subunit described in Uhler et al. *J. Biol. Chem.* 262:15202–15207 (1987), followed by Hind III/Xba In restriction endonuclease digestion of the amplified product, and ligation into the corresponding site in plasmid RcRSV (InVitrogen). RSV-Pit-1 (Fox et al., 1990, *Mol. Endocrinol.* 4:1069–1080.) and RSV-β-gal were kindly supplied by Dr. H. Samuels (New York University). GAL4 constructs pSG424 (Sadowski et al, 1989,. *Nucleic. Acids. Res.*

17:7539 referred to in the present paper as pGAL4(1–147)) and 5×GAL4-CAT (Carey et al., 1990, Nature 345:361–364) were kindly supplied by Dr. M. Ptashne (Sloan-Kettering Institute). GAL4-PREB was constructed by cloning the PREB coding sequence (amino acids 1–417) upstream of and in register with the GAL4(1–147) sequence in pSG424. RSV-PREB was constructed by cloning the PREB coding sequence into the HindIII/XbaI site of RcRSV.

9.2. RESULTS

Figure 5:
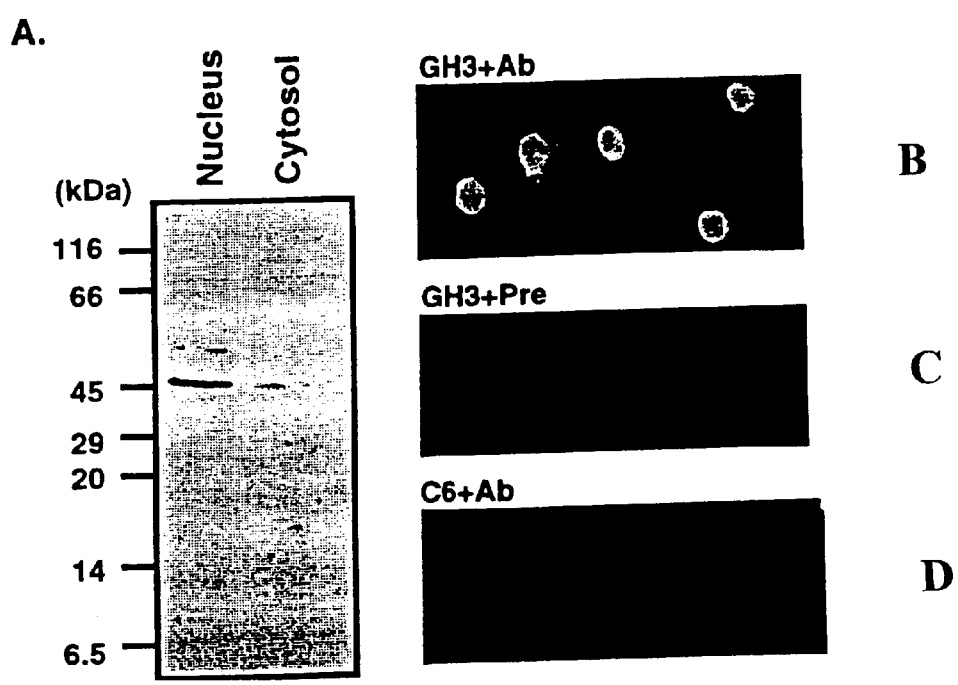

PREB can function as a transcriptional activator. To determine whether PREB might serve as a pituitary cell transcription factor, the expression and intracellular location of PREB protein in the GH3 rat pituitary cells was investigated. Nuclear or cytosolic proteins isolated from an equal number of cells were subjected to Western blot analysis (FIG. 5A). Anti-PREB antiserum, but not control preimmune serum, detected a major 45 kD band that accumulates preferentially in nuclei. This observation implies that PREB is a nuclear protein in pituitary cells. In addition, the size of the protein detected suggests both that synthesis of this protein was initiated by the more N-terminal methionine encoded by the PREB cDNA sequence (i.e., amino acid 1 in FIG. 1B; SEQ ID NO:2) and that the entire PREB cDNA coding sequence had been cloned.

The intracellular location of PREB was examined further by immunocytochemical analysis (FIGS. 5B–D). With anti-PREB antiserum, the pituitary GH3 cells yielded a strong signal that was located specifically over the nuclei (FIG. 5B), while control rat glial C6 cells yielded only a faint diffuse background signal (FIG. 5D). Preimmune serum also yielded only a background signal with either cell line (FIG. 5C). The observation that PREB cross-reacting material exhibited a substantial nuclear accumulation in pituitary cells was consistent with a role for PREB as a cellular transcription factor.

To investigate directly the possible role for PREB as a PRL gene transcription factor, the ability of this protein to transactivate prolactin promoter activity in rat glial C6 cells was examined. The ability of PREB to regulate expression of a construct, (−1957)PRL-CAT, that contains the first 1957 base pairs upstream of the prolactin gene body, and thus covers both the promoter and enhancer regions (Nelson et al., 1988, Science 239:1400–1405) was first investigated. As expected from previous studies (Yan et al., 1994, Mol. Cell. Endocrinol. 101:R25–R30), this PRL-CAT construct alone was inactive in the C6 cells, but was activated by co-expression of Pit-1 (FIG. 6). Co-expression of PREB was also observed to activate (−1957)PRL-CAT expression, showing that this protein exhibited equivalent activation of (−1957)PRL-CAT expression (FIG. 6). This result demonstrated that PREB can transactivate PRL promoter/enhancer activity. This region of the PRL regulatory region contains at least seven Pit-1 binding sites. Nelson et al., 1988, Science 239:1400–1405. The similar levels of activity observed for Pit-1 and PREB on this construct thus suggested that the PRL promoter/enhancer region may contain multiple functional PREB binding sites.

Since element 1P is the only presently known PREB site in the PRL promoter (FIG. 3B), this site was utilized in further functional studies of PREB. In order to study element 1P in its natural context within the PRL promoter, the ability of exogenously expressed PREB to trans-regulate construct (−113)PRL-CAT was investigated. As illustrated in FIG. 7A, the only known prolactin promoter elements in this construct are the CRE-like element (CLE), element 1P, and a TATA box. The observation that the CLE did not bind PREB (FIG. 3) implied that any effects of PREB (and/or Pit-1) on this PRL-CAT construct were mediated via element 1P. These results are consistent with the expression of heterologous genes which are operably linked to the 1P element of the PRL promoter by the over-expression of PREB.

A comparison of the abilities of various inputs of RSV-based vectors for Pit-1 and PREB to trans-regulate (−113) PRL-CAT (FIG. 7A) expression yielded equivalent stimulation by the two proteins (FIG. 7B). This result again demonstrates that PREB can act as a transcriptional activator of a PRL promoter regulatory element. Furthermore, since Pit-1 is known to be a powerful transactivator of PRL gene expression (Fox et al., 1990, Mol. Endocrinol. 4:1069–1080; and Mangalam et al., 1989, Genes Dev. 3:946–958), the observation of equivalent activities for Pit-1 and PREB on two prolactin regulatory region constructs (see FIG. 6 and FIG. 7B) implied that PREB can strongly regulated expression of this gene.

PREB and Pit-1 transactivation activity of prolactin gene expression are additive. The results of electrophoretic shift mobility analysis described above implied that the PREB and Pit-1 binding sites within element 1P are centered over different regions. We thus investigated the ability of PREB to regulate PRL promoter activity in the presence of Pit-1 (FIG. 8). As before, transfection of equal amounts (2.5 μg) of an expression construct for either protein alone yielded transactivation of (−113)PRL-CAT. Co-transfection of 2.5 μg of expression vectors for each protein yielded a level of transactivation that was approximately additive over that yielded by either expression vector alone, suggesting that these two proteins exert additive actions on element 1P. Doubling the input of each expression vector, to close to maximal activity levels (see FIG. 8), increased expression three-fold, again consistent with an approximately additive action of PREB and Pit-1. These observations suggested that, at least in the basal cellular state, these two proteins may exert actions on element 1P that are of approximately equal strength, but largely independent. This coupled with the DNA binding data suggested that the PREB and Pit-1 occupy proximal sites on the PRL promoter and is consistent with the ability of PREB fusion proteins to inhibit the binding of Pit-1 and block Pit-1 transactivation of PRL.

PREB can mediate transcriptional stimulation by PKA in either GH3 pituitary cells or heterologous C6 cells. As described above, previous studies have implied that Pit-1 is not the direct functional target of PKA action on the PRL promoter. Inspection of the predicted PREB amino acid sequence revealed a number of potential PKA phosphorylation sites. This, together with the observations described above that PREB can bind specifically to PRL element 1P and exhibited transcriptional activity, suggested that PREB may represent the cellular protein that directly mediates PKA action on the PRL promoter via element 1P. To begin to investigate this possibility in GH3 cells, under conditions that are independent of both endogenous PREB and PREB binding sites, the ability of a GAL4-PREB to transmit PKA action to a co-transfected GAL4 indicator construct was investigated (FIG. 9). As expected, control GAL(1–147) was unable to transactivate 5×GAL4-CAT expression, in either the presence or absence of an RSV-PKA expression vector. In the absence of RSV-PKA, GAL4-PREB alone strongly transactivated 5XGAL4-CAT, which demonstrated again that PREB contains a transcriptional activator domain. Co-transfection of RSV-PKA yielded a three-fold increase in the ability of GAL4-PREB to transactivate 5×GAL4-CAT. This observation demonstrated that PREB can support a PKA-mediated transcriptional response in pituitary cells, possibly in the absence of any change in its ability to bind DNA.

The ability of PREB to transmit a PKA transcriptional signal to the PRL promoter, in the absence of other pituitary cell signals was also investigated. To do this, the effect of expression of RSV-PKA in C6 glial cells on trans-activation by either Pit-1 or PREB of indicator construct (−113)PRL-CAT (FIG. 10) was examined. As before, (−113)PRL-CAT alone exhibited minimal activity, which was only slightly increased by co-expression of PKA. Co-expression of Pit-1 strongly transactivated CAT activity. However, this activity was not further increased by co-expression of PKA, in agreement with previous observations (Okimura et al. Mol. Endocrinol. 8:1559–1565. 1994). In contrast, the trans-activation of CAT activity by PREB was strongly increased by co-expression of PKA. Thus, PREB (but not Pit-1) can support a PKA-mediated transcriptional response directed by element 1P in the context of the PRL promoter.

10. EXAMPLE

ISOLATION AND SEQUENCE ANALYSIS OF THE HUMAN PREB cDNA 10.1 MATERIALS AND METHODS cDNA Library Screening, Sequence and Analysis. A Clontech (Palo Alto, Calif.) fetal brain cDNA library was plated and screened according to the manufacturer's instructions. All hybridization washes were performed in 1×SSC with 0.1%SDS at 65° C. The cDNA inserts were isolated from positive phage clones according to standard methods (see Chisholm, *Biotechs* 7:21–23 (1989), incorporated herein by reference), and subcloned into the plasmid pBS (Stratagene, La Jolla, Calif.) Double-stranded plasmid sequencing was performed using an ABI 377 sequencer (PE Bioscience, Foster City, Calif.) and PRISM Dye-terminators Cycle Sequencing Ready Reaction Kit (PE Bioscience, Foster City, Calif.), with FS enzyme kit (PE Bioscience, Foster City, Calif.). The primer ATGTCCTGGGTGC-CGCGG (SEQ ID NO:14) was used to sequence across the 5' end of the open reading frame (ORF) in the 2.5 kb BamHI genomic pBS subclone. Both BamHI genomic subclones were sequenced entirely by primer walking, and all pBS clones were sequenced in both directions. cDNA sequence was translated using the GCG package (Human Genome Mapping Project (HGMP), Cambridge, UK).

PAC Library Screening. A human chromosome 2 specific PAC library was obtained from the Human Genome Mapping Project (HGMP) resource center (Cambridge, UK). A SacII-BamHI fragment of the rat PREB cDNA was labeled with $^{32}$P-dCTP and hybridized overnight at 65° C. in a hybridization solution containing:6×SSC, 0.3% SDS, 50 mM NaH2PO4 (pH6.2), 5×Denhart's solution and 50 μg/ml denatured salmon sperm. The filter was washed to a stringency of 1×SSC/0.1% SDS, at 65° C., and exposed to x-ray film (Kodak, Rochester, N.Y.). A PstI fragment, incorporating exon two of the murine Sax2 cDNA, was labeled and hybridized to the genomic PAC filter as described above, except that washes were performed in 6×SCC/0.1% SDS solution, and an additional hybridization and wash at 42° C. was also performed. Each experimental condition was repeated using the Sax2 probe after competition for one hour, at 65° C., with human genomic DNA. Positive clones were requested and received from HGMP.

10.2 RESULTS

A SacII/BamHI fragment of rat PREB cDNA (which encompasses the entire open reading frame (ORF), was used to screen a human fetal brain cDNA library (Clontech, Palo Alto, Calif.). Two positive clones (FB6 and FB8) were identified, isolated and sequenced and found to be identical in size except for the absence from FB6 of 49 bases of the 5' sequence. The sequence of the 1.9 kb FB8 clone was shown to be >83% identical with the rat PREB cDNA over the entire length of the cDNA clone, including the 3' untranslated region (UTR). A long ORF, encoding 412 amino acids was observed in FB8, possessing >89% identity and 91% similarity to rat PREB, implying that it encodes the human PREB homologue. However, comparison between the predicted human and rodent PREB proteins showed that five amino acid residues, including the initiating methionine residue, were absent from the human protein. In contrast, an ATG that encodes a second methionine residue, located downstream in both rat and mouse PREB transcripts, was conserved in the human transcript.

A primer was designed to determine the initiation site of human PREB translation which was used to sequence across the 5' end of the ORF in a 2.5 kb BamHII genomic fragment from a human PAC (14K14) that incorporates the PREB gene. Translation of the resultant nucleotide sequence predicted an additional five residues possessing 100% identity with the N-terminus of the rodent PREB proteins, including the initiating methionine. BESTFIT analysis (GCG at HGMP) showed a further sequence from PAC 14K14 with nucleotide homology to the 5'UTR of the cloned PREB transcripts, indicating a possible human 5'UTR of 144bp. This sequence data implies that FB8 represents a partial cDNA clone, and that the full length human PREB transcript encodes a protein of 417 residues in length. The sequence of the full length FB8 transcript, the predicted amino acid sequence including the amino acid residues (SEQ ID NO:13) predicted from the SEQ ID NO:12, and the 5'UTR are all shown in FIG. 11A.

BLAST analysis showed that the PREB protein has significant sequence similarity with the yeast TUP1 transcriptional repressor protein (Genbank Accession Number p16649; Williams and Trumbly, *Mol. Cell. Biol.* 10:6500–11 (1990) incorporated herein by reference), and Pfam database screening identified PREB as a WD-repeat family member. Three potential WD repeats are conserved among all PREB homologues characterized to date (see FIG. 12). FIG. 12 shows that the three WD-repeats in human PREB are conserved with rat and mouse PREB repeats 1, 2 and 3 respectively and with regions of the yeast TUP1 protein (accession number p16649; Williams and Trumbly, *Mol. Cell. Biol.* 10:6500–6511 (1990). PREB repeat 3, although highly similar to the WD consensus sequence, does not share amino acid sequence with any of the yeast TUP1 repeats, and instead is most similar to a WD-repeat within a hypothetical yeast protein (accession number p53877). The two proline-glutamine rich amino acid regions, which have been noted by Fliss et al., *Mol. Endocrinol.* 13:644–657 (1999), incorporated herein by reference, are also highly conserved among rat, mouse and human PREB proteins.

11. EXAMPLE

ANALYSIS OF PREB GENE EXPRESSION 11.1 MATERIALS AND METHODS

Northern Analysis. A human RNA master blot, containing standardized mRNA levels from 43 human adult and seven fetal tissues were hybridized and washed according to the manufacturer's instructions (Clontech, Palo Alto, Calif.). All PREB probes were prepared for hybridization to the RNA filter according to the manufacturer's instructions (Clonetech). A 55 bp fragment was PCR amplified from the PAC 14K14, using the following primers: Forward: ATGTC-CTGGGTGCCGCGG (SEQ ID NO:14); Reverse: TGAAACGAGTACAACGGGA (SEQ ID NO:15). Genomic DNA (100 ng) was denatured for 5 minutes and then subjected to 30 cycles of denaturing at 94° C., annealing at 61° C., and extension at 72° C., each for 30 seconds.

11.2. RESULTS

Northern analysis showed the presence of a three possible alternatively spliced transcripts of 2.2 kb, 1.9 kb and 1.5 kb in six human adult tissues examined. Although these transcripts are apparently produced in tissue specific patterns, at least one PREB transcript was expressed in all tissues examined, with largest 2.2 kb transcript being present in every tissue.

A human RNA "master blot" (Clonetech) was hybridized to a 350 bp PstI fragment derived from the 3'UTR of the human transcript. Following stringent washing, PREB transcripts were detected in all 43 adult tissues and seven fetal tissues represented on the blot (see FIGS. 13A–D). The same filter was used in all experiments, the signal being stripped and filters checked by autoradiography before each re-hybridization. Ubiquitin cDNA hybridization to the RNA filter was used as a control (FIG. 13B). The filter was washed at 0.1×SSC/1% SDS at 50° C., and exposed to x-ray for 16 hours. Before hybridization, the $^{32}$P-labeled probe was denatured and then competed with human Cot-1 DNA for one hour at 68° C., according to the manufacturer's instructions (Clontech). Although PREB was ubiquitously expressed (FIG. 13C), after a 16 hour exposure to x-ray film, the levels of expression varied greatly among tissues, with very high levels detected in adult salivary gland, liver, pancreas and skeletal muscle, and fetal liver tissue. In FIG. 13C, the hybridization and washing conditions, and probe preparation were identical to the control probe experiments. In contrast, the lowest levels of expression were notably in the adult aorta and lung (see FIG. 13D). The expression patterns detected may be indicative of a major function in tissues exhibiting very high expression levels. The signal observed in H4 (13C and 13D) is due to the presence of contaminating E. coli DNA within the PREB clone DNA preparation from which the probe was made.

To investigate whether PREB transcripts extend further 5' than the sequence contained in the FB8 clone, and thus might contain the more upstream methionine codon identified previously in rat PREB (see Fliss et al, Mol. Endocrinol. 13:644–657 (1999)), PCR primers were designed to amplify a 55 bp fragment of the human PREB gene between the two putative methionine codons from the genomic PAC 14K14. The amplified product was $^{32}$P-labeled and then hybridized to the RNA blot described above. The hybridization pattern in all tissues, including brain tissues, was identical to that described above using the 3'UTR region of PREB as a probe. This result suggests that the full length PREB transcript extends further than the FB6 and FB8 clones isolated from the fetal brain cDNA library, and that this predicted human transcript corresponds to the 2.2 kb PREB transcript.

The 1.9 kb FB8 cDNA may correspond to a PREB transcript splice variant described by Fliss et al, Mol. Endocrinol. 13:644–657 (1999). The FB8 transcript would encode an N-terminally truncated protein. Preliminary studies have identified two putative splice variants of a Drosophila cDNA that encode proteins with high similarity to the mammalian PREB proteins. It is possible that the multiple bands observed (see Fliss et al, Mol. Endocrinol. 13:644–657 (1999)) arise from cross-hybridization between related mRNA transcripts. The 2.2 kb transcript would then represent the sole human PREB mRNA species.

12. FISH MAPPING TO HUMAN CHROMOSOME 2P23 AND GENOMIC ORGANIZATION OF THE PREB GENE

12.1 MATERIALS AND METHODS

FISH. Metaphase spreads were prepared from EBV-transformed cell lines and peripheral whole blood by standard techniques. See Barch et al., The AGT Cytogenics Laboratory Manual, Lippincott-Raven, New York (1997), incorporated herein by reference. Maxiprep PAC cDNA (prepared using Maxiprep, Qiagen, Valencia, Calif., according to the manufacturer's instructions) was labeled by nick translation with Digoxigenin-11-dUTP (Boehringer Mannhein). In situ hybridization was carried out as follows: The hybridization mixture [150 ng probe DNA, 4 μg Cot-I DNA, and 7 μg Herring Sperm DNA (Gibco/BRL, Rockville, Md.) in Hybrisol VII (Oncor, Gaithersburg, Md.) was applied to heat denatured normal metaphase spreads and hybridized overnight in a humid chamber at 37° C. Unbound DNA fragments were removed by washing in 2×SSC at 72° C. for 5 minutes and 1×PBD (phosphate buffered detergent) for 3 minutes at room temperature. Slides were then incubated with 60 μl anti-Digoxigenin rhodamine (Oncor), for 15 minutes at 37° C. This was followed by three-3 minute washes in 1×PBD at room temperature. FISH images were captured with an ImagePoint cooled CCD video camera (Photometrics, Tuscan, Ariz.), through a Labophot-2A fluorescence microscope (Nikon, Melville, N.Y.). Chromosome identification was facilitated by counterstaining with 0.1 μg/μl DAPI in Vectashield (Vector Latoratories, Burlingame, Calif.). See Florijn et al., Cytometry 19:177–182 (1995).

12.2 RESULTS

Preliminary somatic cell hybrid mapping, using a human oligo-dT primed EST (ATCC 125415, Manassa, Va.) with homology to the 3'UTR of the rat PREB cDNA, localized the human gene to chromosome 2. A human chromosome 2 specific PAC library (HGMP) was screened with the SacII/BamHI rat PREB fragment described above, and two positive PACS were identified:14K14, and 14I02. Each was used as a probe in FISH analysis of normal metaphase chromosome spreads and each yielded identical specific signals on human chromosome 2, within the G-band 2p23 (see FIGS. 14A and 14B).

The two PREB positive PACs described above were employed to investigate the genomic organization of the PREB gene. BamHI digestion of each PAC yielded two fragments, about 2.5 kb and 1.6 kb in size, that specifically hybridized to a probe of the full length human PREB transcript. These fragments were subcloned into the plasmid pBS and sequenced. The entire PREB gene was localized within these two BamHI fragments and shown to span 3.7 kb. PREB contains eight exons, varying in size between 81 bp and the largest 769 bp exon at the 3' end of the gene. All intronic 5' acceptor and 3' donor sites are consistent with consensus sequences.

The murine Preb gene has previously been mapped to proximal murine chromosome 5; a region sytenic to both human chromosome 4p16 and 2p23 (see Clelland et al, Genomics, In Press (2000), incorporated herein by reference). The murine Sax2 gene, a member of the small group of homeobox genes related to the Drosophila NKI homoedomain (see Chen and Lufkin, Mamm. Genome 8:697–8 (1997), incorporated herein by reference), co-segregates with murine Preb in the progeny of a BSS2 specific backcross panel (Clelland, et al, Genomics, In Press (2000)). Although the human Sax2 gene has not been cloned, the above results imply that a human homologue of this gene will map either to 4p16 or 2p23. Further in support of this, a 3.0 kb genomic fragment containing the entire homeodomain (exon 2), of the murine Sax2 gene was hybridized to a human chromosome 2 specific library (HGMP), using varying hybridization and wash conditions as well as probe competition with human total genomic DNA. No positive genomic PAC clones were detected in any of the hybridization experiments, suggesting that the human Sax2 gene will likely map to human chromosome 4p16.

13. MAPPING OF PREB WITHIN A REGION ASSOCIATED WITH HUMAN TRISOMY 2P SYNDROME

13.1. RESULTS

The FISH mapping described above localized the human PREB gene to a region associated with a partial trisomy syndrome in humans. Of the sixty cases reported of trisomy 2p, 43 encompass the chromosome band 2p23. See Clelland et al, Genomics, In Press (2000); Magarbane et al., *J. Med. Genet.* 34:783–786 (1997); Patel et al., *J. Med. Genet.* 34:949–951 (1997); Winsor et al., *Prenatal Diagnosis* 17:665–669 (1997); Al-Saffar et al, *Am. J. Med. Genet.* 87:45–48 (1999), all incorporated herein by reference. In over one third of these individuals, the proximal breakpoint within chromosome 2 maps to 2p23, which may be indicative of a repetitive region within this genomic DNA that pre-disposes to structural rearrangements, as observed elsewhere within the human genome. See Halford et al., *Hum. Mol. Genet.* 2:191–196 (1993); Phimister, *Nat. Genet.* 16:11 (1997); Small et al., *Nat. Genet.* 16:96–99 (1997), incorporated herein by reference. A role for PREB in the trisomy phenotype would imply that PREB maps to the commonly duplicated region of 2p23. The dosage of PREB was analyzed in the individuals described above. PAC 14K14 was hybridized to metaphase chromosome spreads and interphase nuclei obtained from the individuals with duplication breakpoints within 2p23 (11 and Coriell Cell repositories, Al-Saffar et al., *Am. J. Hum. Genet.* 65Supp(4):850 (1999), incorporated herein by reference), and two individuals whose region of duplication extends from 2p21-pter (Scola, *Am. J. Human. Genet.* 31:110A (1979); Lurie et al, *Am. J. Med. Genet.* 55:229–236 (1995), both incorporated herein by reference). In all four cases, three signals were detected in each interphase nuclei examined, and all metaphase chromosomes clearly showed the presence of three copies of the PREB gene (see FIGS. 14C, 14D, 14E, 14F, and 14G).

14. ROLE OF PREB IN OSTEOPOROSIS

Four human DNA samples were obtained from a nuclear family with the mother and two sons diagnosed with osteoporosis (supplied by Dr. Loretta Spotilla, Thomas Jefferson University, Philadelphia, Pa.) and analyzed for mutations of the PREB gene. The DNA from the two sons contained large homozygous deletions, incorporating all, or nearly all of the PREB gene, suggesting a correlation between familial osteoporosis and mutations in the PREB gene.

Initial experiments were performed to PCR amplify the entire human PREB gene, including intron and exon boundaries, using the following four primer pairs (which all map to intronic or untranslated sequence of the PREB gene):

Forward 1: CTCGGCTTCCTGCTGATGGT (SEQ ID NO:19)

Reverse 1: CAAGCGGGTCTTCCCAACA (SEQ ID NO:20)

Forward 2: CAGACTCTTCCCTAAACGTGCT )SEQ ID NO:21)

Reverse 2; ACTTACTGGGCAAGCAGCATA (SEQ ID NO:22)

Forward 3: CCCACGAAGGGGAGATTGAA (SEQ ID NO:23)

Reverse 3: GGGCACGTTTCTGGTCATTA (SEQ ID NO:24)

Forward 4: CTTTGAAGGGTTCTGGTTTTCA (SEQ ID NO:25)

Reverse 4 GGTCTCAGTTCACTCTTTCCTTGTTT (SEQ ID NO:26)

Denaturation was performed at 95° C. for 1 min. Followed by an annealing step (specific temp for each primer pair; 1.5 mM MgCl2 added and annealed at 52° C. for Forward 1 and Reverse 1; 2.0 mM MgCl2/anneal 51° C. for Forward 2 and Reverse 2; 2.5 mM MgCl2/anneal 50° C. for Forward 3 and Reverse 3; and 1.5 mM MgCl2/anneal 49° C. for Forward 4 and Reverse 4) for 1 min. Extension was carried out at 72° C. for 1 min.

All PCRs were performed using commercial enzyme, buffers and dNTPs (Qiagen), and all PCR conditions were determined using control DNA.

One nuclear family was used for the initial experiment. The mother and one child have both low hip and spine bone mineral density (BMD), the second child has low hip BMD. The father is unaffected. The four PCR amplifications (using the primer pairs above) failed to amplify any products in either of the two children., however products were amplified in both parents and a control individual (FIG. 17). To test the quality of DNA, primers were then designed to amplify the GAPDH pseudogene on chromosome 12, the osteopontin gene on chromosome 4, and the keteohexokinase gene that also maps to 2p23 (FIG. 17). In all cases a product was obtained in each individual examined. Further primers were designed, in both intronic and exonic sequences of the PREB gene, to ensure the failure of PCR amplification in the children was not due to experimental problems, such as shearing of genomic DNA, etc. In each case no amplifiable product was obtained (FIG. 17), except when the primer pair CB306 (forward)/CB305 (reverse) (see primers below) were used. This primer pair amplifies a 105bp fragment in exon 1 of the PREB gene. However, in a further experiment using the primers CB306/Reverse 1, again no product was detectable.

CB306: ATGTCCTGGGTGCCGCGG (SEQ ID NO:27)

CB305: TGAAACGCGTACAACGGGA (SEQ ID NO:28)

(2.5 mM MgCl2/Anneal 52° C.)

CB301: CAGCAGAGAAGAAATGTG (SEQ ID NO:29)

CB317: TGGTAGCGGTAAGGTGTGCTGG (SEQ ID NO:30)

(1.5 mM MgCl2/Anneal 53° C.)

Various references are cited herein, the contents of which are hereby incorporated by reference in their entireties.

What is claimed is:

1. A purified and isolated PREB protein-encoding nucleic acid molecule, having the sequence set forth in SEQ ID NO:1.

2. The PREB protein-encoding nucleic acid molecule of claim 1, as contained in a vector molecule.

3. A purified and isolated PREB-encoding nucleic acid molecule having the sequence set forth in SEQ ID NO:12.

4. The PREB-encoding nucleic acid molecule of claim 3, as contained in a vector molecule.

5. A purified and isolated PREB-encoding nucleic acid molecule having the sequence set forth in SEQ ID NO:16.

6. A purified and isolated nucleic acid molecule encoding a PREB protein, wherein the PREB protein has an amino acid sequence as set forth in SEQ ID NO:17.

* * * * *

UNITED STATES PATENT AND TRADEMARK OFFICE
CERTIFICATE OF CORRECTION

PATENT NO. : 6,586,581 B1  
APPLICATION NO. : 09/533494  
DATED : July 1, 2003  
INVENTOR(S) : F. Carter Bancroft, Maikiko Fliss and Catherine L. Clelland Page 1 of 1

It is certified that error appears in the above-identified patent and that said Letters Patent is hereby corrected as shown below:

Please replace the paragraph beginning at Col. 1, line 6 and ending at Col. 1, line 9 with the following paragraph:

--This invention was made with government support under NIH grant numbers GM36847 and DA07859 awarded by the National Institute of Health. The United States Government has certain rights in the invention.--

Signed and Sealed this

Twenty-second Day of September, 2009

David J. Kappos  
*Director of the United States Patent and Trademark Office*